US 10,835,593 B2

(12) United States Patent
Liu et al.

(10) Patent No.: US 10,835,593 B2
(45) Date of Patent: Nov. 17, 2020

(54) MODIFIED ANTHRAX TOXIN PROTECTIVE ANTIGEN

(71) Applicant: The United States of America, as represented by the Secretary, Department of Health and Human Services, Bethesda, MD (US)

(72) Inventors: Shi-Hui Liu, Gaithersburg, MD (US); Stephen H. Leppla, Bethesda, MD (US); Thomas H. Bugge, Bethesda, MD (US); Alexander N. Wein, Decatur, GA (US); Diane E. Peters, Grafton, MA (US); Jie Liu, Gaithersburg, MD (US); Kuang-Hua Chen, Gaithersburg, MD (US)

(73) Assignee: The United States of America as represented by the Secretary Department of Health and Human Services, Bethesda, MD (US)

( * ) Notice: Subject to any disclaimer, the term of this patent is extended or adjusted under 35 U.S.C. 154(b) by 0 days.

(21) Appl. No.: 15/755,341

(22) PCT Filed: Aug. 25, 2016

(86) PCT No.: PCT/US2016/048706
§ 371 (c)(1),
(2) Date: Feb. 26, 2018

(87) PCT Pub. No.: WO2017/035359
PCT Pub. Date: Mar. 2, 2017

(65) Prior Publication Data
US 2018/0250376 A1 Sep. 6, 2018

Related U.S. Application Data

(60) Provisional application No. 62/323,218, filed on Apr. 15, 2016, provisional application No. 62/210,771, filed on Aug. 27, 2015.

(51) Int. Cl.
| | |
|---|---|
| *A61K 39/07* | (2006.01) |
| *A61P 35/00* | (2006.01) |
| *A61K 39/00* | (2006.01) |
| *A61K 45/06* | (2006.01) |
| *C07K 14/325* | (2006.01) |

(52) U.S. Cl.
CPC .......... *A61K 39/07* (2013.01); *A61K 39/0011* (2013.01); *A61K 45/06* (2013.01); *A61P 35/00* (2018.01); *C07K 14/325* (2013.01); *A61K 2039/5158* (2013.01); *A61K 2039/55522* (2013.01)

(58) Field of Classification Search
None
See application file for complete search history.

(56) References Cited

U.S. PATENT DOCUMENTS

| 7,601,351 B1 * | 10/2009 | Rosen .................... C07K 16/00 424/139.1 |
| 7,947,289 B2 | 5/2011 | Leppla et al. |
| 8,388,933 B2 | 3/2013 | Leppla et al. |
| 2009/0142794 A1 | 6/2009 | Leppla et al. |
| 2010/0168012 A1 | 7/2010 | Leppla et al. |
| 2011/0280908 A1 | 11/2011 | Leppla et al. |

FOREIGN PATENT DOCUMENTS

| CN | 101215568 B | 6/2010 |
| WO | WO 2001/21656 A2 | 3/2001 |
| WO | WO 2005/090393 A2 | 9/2005 |
| WO | WO 2014/134187 A1 | 9/2014 |
| WO | WO 2014/205187 A1 | 12/2014 |
| WO | WO 2015/048332 A2 | 4/2015 |
| WO | WO 2017/035359 | 3/2017 |

OTHER PUBLICATIONS

Peters et al. Toxicity and Applied Pharmacology 279 (2014) 220-229.*
Mourez et al. PNAS Nov. 25, 2003 100(24) 13803-13808.*
Martin, Erik William. Engineered Membrane-Anchored Serine Protease-Activated Anthrax Toxins as a Potential Treatment Approach for Ovarian Cancer. Order No. 3746126 University of Maryland, Baltimore, 2015 Ann Arbor ProQuest. Sep. 12, 2019.*
Rosovitz et al. The Journal of Biological Chemistry vol. 278, No. 33, issue Aug. 15, pp. 30936-30944, 2003.*
UniprotKB Accession # S5M0J7 Oct. 16, 2013.*
Chauhan et al. Infect. Immun. 70:4477-4484 (2002).*
Abi-Habib, RJ et al., 'BRAF status and mitogen-activated protein/extracellular signal-regulated kinase kinase 1/2 activity indicate sensitivity of melanoma cells to anthrax lethal toxin', *Mol. Cancer Ther.*, 4: 1303-1310 (2005).
Arora, N et al., 'Residues 1-254 of Anthrax Toxin Lethal Factor Are Sufficient to Cause Cellular Uptake of Fused Polypeptides', *J. Biol. Chem.*, 268:3334-3341 (1993).
Arora, N et al., 'Fusions of Anthrax Toxin Lethal Factor with Shiga Toxin and Diphtheria Toxin Enzymatic Domains Are Toxic to Mammalian Cells', *Infect. Immun.*, 62: 4955-4961 (1994).
Chen, KH et al., 'Selection of Anthrax Toxin Protective Antigen Variants That Discriminate between the Cellular Receptors TEM8 and CMG2 and Achieve Targeting of Tumor Cells', *J. Biol. Chem.*, 282: 9834-9846 (2007).

(Continued)

*Primary Examiner* — Oluwatosin A Ogunbiyi
(74) *Attorney, Agent, or Firm* — Leydig Voit and Mayer Ltd

(57) ABSTRACT

Disclosed is a *Bacillus anthracis* protective antigen (PA) comprising a PA amino acid sequence, wherein one or more of amino acid residues I207, I210, E654, I656, R659, M662, Y681, and L687, as defined by reference to SEQ ID NO: 1, are, independently, substituted, with the proviso that amino acid residue I207 is not substituted with alanine and amino acid residue I210 is not substituted with alanine. Related compositions, nucleic acids, recombinant expression vectors, host cells, populations of cells, methods of treating or preventing cancer in a mammal, and methods of inhibiting the growth of a target cell are also disclosed.

5 Claims, 27 Drawing Sheets
Specification includes a Sequence Listing.

(56) References Cited

OTHER PUBLICATIONS

Chen, KH et al., 'Anthrax Toxin Protective Antigen Variants That Selectively Utilize either the CMG2 or TEM8 Receptors for Cellular Uptake and Tumor Targeting', *J. Biol. Chem.*, 291: 22021-22029 (2016).
Dano, K et al., 'Cancer invasion and tissue remodeling--cooperation of protease systems and cell types', *APMIS*, 107: 120-127 (1999).
Genbank Accession No. NP_052806 'pXO1-110 (plasmid) [*Bacillus anthracis*]' (2014).
Geran, RI et al., 'Protocols for screening chemical agents and natural products against animal tumors and other biological systems', *Cancer Chemother. Rep.*, 3(2): 1-103 (1972).
Gupta, PK et al., 'Role of N-Terminal Amino Acids in the Potency of Anthrax Lethal Factor', *PLoS ONE*, 3: e3130 (2008).
Hassan, R et al., 'Major cancer regressions in mesothelioma after treatment with an anti-mesothelin immunotoxin and immune suppression', *Sci. Transl. Med.*, 5(208): 208ra147 (2013).
International Search Report of International Application No. PCT/US2016/048706, dated Nov. 25, 2016.
Ittelson, TR et al., 'Diphtheria toxin: specific competition for cell receptors', *Nature*, 242: 330-332 (1973).
Li, Y et al, 'Direct labeling and visualization of blood vessels with lipophilic carbocyanine dye DiI', *Nat. Protoc.*, 3: 1703-1708 (2008).
Liu, S et al., 'Tumor cell-selective cytotoxicity of matrix metalloproteinase-activated anthrax toxin', *Cancer Res.*, 60: 6061-6067 (2000).
Liu, S et al., 'Targeting of Tumor Cells by Cell Surface Urokinase Plasminogen Activator-dependent Anthrax Toxin', *J. Biol. Chem.*, 276: 17976-17984 (2001).
Liu, S et al., 'Cell Surface Tumor Endothelium Marker 8 Cytoplasmic Tail-independent Anthrax Toxin Binding, Proteolytic Processing, Oligomer Formation, and Internalization', *J. Biol. Chem.*, 278: 5227-5234 (2003).
Liu, S et al., 'Intermolecular complementation achieves high specificity tumor targeting by anthrax toxin', *Nat. Biotechnol.*, 23: 725-730 (2005).
Liu, S et al., 'Characterization of the interaction between anthrax toxin and its cellular receptors', *Cell Microbiol.*, 9: 977-987 (2007).
Liu, S et al., 'Capillary morphogenesis protein-2 is the major receptor mediating lethality of anthrax toxin in vivo', *Proc. Natl. Acad. Sci. USA*, 106: 12424-12429 (2009).
Liu, S et al., 'Anthrax toxin targeting of myeloid cells through the CMG2 receptor is essential for establishment of Bacillus anthracis infections in mice', *Cell Host Microbe*, 8: 455-462 (2010).
Liu, S et al., 'The Receptors that Mediate the Direct Lethality of Anthrax Toxin', *Toxins (Basel)*, 5: 1-8 (2012).
Liu, S et al., 'Key tissue targets responsible for anthrax-toxin-induced lethality', *Nature*, 501: 63-68 (2013).
Liu, S, 'Solid tumor therapy by selectively targeting stromal endothelial cells', *Proc. Natl. Acad. Sci. USA*, 113(28): E4079-E4087 (2016).
Mossoba, Me et al., 'Pentostatin Plus Cyclophosphamide Safely and Effectively Prevents Immunotoxin Immunogenicity in Murine Hosts', *Clin. Cancer Res.*, 17: 3697-3705 (2011).
Onda, M et al., 'Tofacitinib suppresses antibody responses to protein therapeutics in murine hosts', *J. Immunol.*, 193(1): 48-55 (2014).
Park, S et al., 'Optimized production and purification of Bacillus anthracis lethal factor', *Protein Expr. Purif.*, 18: 293-302 (2000).
Pomerantsev, AP et al., 'A Bacillus anthracis strain deleted for six proteases serves as an effective host for production of recombinant proteins', *Protein Expr. Purif.*, 80: 80-90 (2011).
Reynolds, Le et al., 'Primary mouse endothelial cell culture for assays of angiogenesis', *Methods Mol. Med.*, 120:503-509 (2006).
Santelli, E et al., 'Crystal structure of a complex between anthrax toxin and its host cell receptor', *Nature*, 430: 905-908 (2004).
Singh, Y et al., 'A Deleted Variant of Bacillus anthracis Protective Antigen is Non-toxic and Blocks Anthrax Toxin Action in Vivo', *J. Biol. Chem.*, 264: 19103-19107 (1989).
Wein, AN et al., 'An anthrax toxin variant with an improved activity in tumor targeting', *Sci. Rep.*, 5: 16267 (2015).
Weiss, MA et al., 'Pentostatin and Cyclophosphamide: An Effective New Regimen in Previously Treated Patients With Chronic Lymphocytic Leukemia', *J. Clin. Oncol.*, 21(7): 1278-1284 (2003).
Written Opinion of the International Searching Authority of International Application No. PCT/US2016/048706, dated Nov. 25, 2016.
Ye, L et al., 'Capillary morphogenesis gene 2 regulates adhesion and invasiveness of prostate cancer cells', *Oneal. Lett.*, 7(6): 2149-2153 (2014).
Zaccolo, M et al., 'An approach to random mutagenesis of DNA using mixtures of triphosphate derivatives of nucleoside analogues', *J. Mol. Biol.*, 255: 589-603 (1996).
European Patent Office Communication pursuant to Article 94(3) EPC, Application No. 16767062.2, dated Jul. 30, 2019, 5 pages.

\* cited by examiner

FIG. 3

MODIFIED ANTHRAX TOXIN PROTECTIVE ANTIGEN

CROSS-REFERENCE TO RELATED APPLICATIONS

This patent application is the U.S. National Stage of Patent Application No. PCT/US2016/048706, filed Aug. 25, 2016, which claims the benefit of U.S. Provisional Patent Application No. 62/323,218, filed Apr. 15, 2016, and U.S. Provisional Patent Application No. 62/210,771, filed Aug. 27, 2015, each of which is incorporated by reference in its entirety herein.

STATEMENT REGARDING FEDERALLY SPONSORED RESEARCH AND DEVELOPMENT

This invention was made with Government support under project numbers HL006185-01, ZIA A10009829-12, 1 ZIA AI000929-12, and Z01DE0699 by the National Institutes of Health, National Institute of Allergy and Infectious Diseases. The Government has certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 49,054 Byte ASCII (Text) file named "737922_ST.TXT," dated Feb. 26, 2018.

BACKGROUND OF THE INVENTION

*Bacillus anthracis* anthrax toxin is a bacterial toxin with cytotoxic activity that may be effective for destroying or inhibiting the growth of undesirable cells, e.g., cancer cells. Accordingly, one or more components of the anthrax toxin may be useful for treating or preventing diseases such as, e.g., cancer. However, anthrax toxin or components thereof may be toxic to normal cells. Accordingly, there exists a need for improved anthrax toxins.

BRIEF SUMMARY OF THE INVENTION

An embodiment of the invention provides a *Bacillus anthracis* protective antigen (PA) comprising a PA amino acid sequence, wherein one or more of amino acid residues I207, I210, E654, I656, R659, M662, Y681, and L687, as defined by reference to SEQ ID NO: 1, are, independently, substituted, with the proviso that amino acid residue I207 is not substituted with alanine and amino acid residue I210 is not substituted with alanine.

Another embodiment of the invention provides a *Bacillus anthracis* PA comprising a PA amino acid sequence, wherein one or both of amino acid residues I207 and I210, as defined by reference to SEQ ID NO: 1, are, independently, substituted, with the proviso that amino acid residue I207 is not substituted with alanine and amino acid residue I210 is not substituted with alanine.

Another embodiment of the invention provides a *Bacillus anthracis* PA comprising a PA amino acid sequence, wherein one or more of amino acid residues I656, Y681, and L687, as defined by reference to SEQ ID NO: 1, are, independently, substituted.

Another embodiment of the invention provides a *Bacillus anthracis* PA comprising a PA amino acid sequence, wherein one or more of amino acid residues E654, R659, and M662, as defined by reference to SEQ ID NO: 1, are, independently, substituted.

Another embodiment of the invention provides a method of treating or preventing a solid tumor in a mammal, the method comprising administering to the mammal pentostatin and cyclophosphamide in an amount effective to treat or prevent the solid tumor in the mammal.

Further embodiments of the invention provide related compositions, nucleic acids, recombinant expression vectors, host cells, and methods of treating or preventing cancer.

BRIEF DESCRIPTION OF THE SEVERAL VIEWS OF THE DRAWING(S)

FIG. 3A is a schematic representation of intermolecular complementation of the PA variants.

FIG. 3B is a graph showing the cell viability (%) of RAW264.7 macrophage cells treated with the indicated PA variants at 500 ng/mL in the presence of 100 ng/mL LF (single protein, unshaded bars) or at 250 ng/mL plus 250 ng/mL PA-R200A (shaded bars) or PA-R200C (striped bars) in the presence of 100 ng/mL LF for 6 h.

Figure 4:
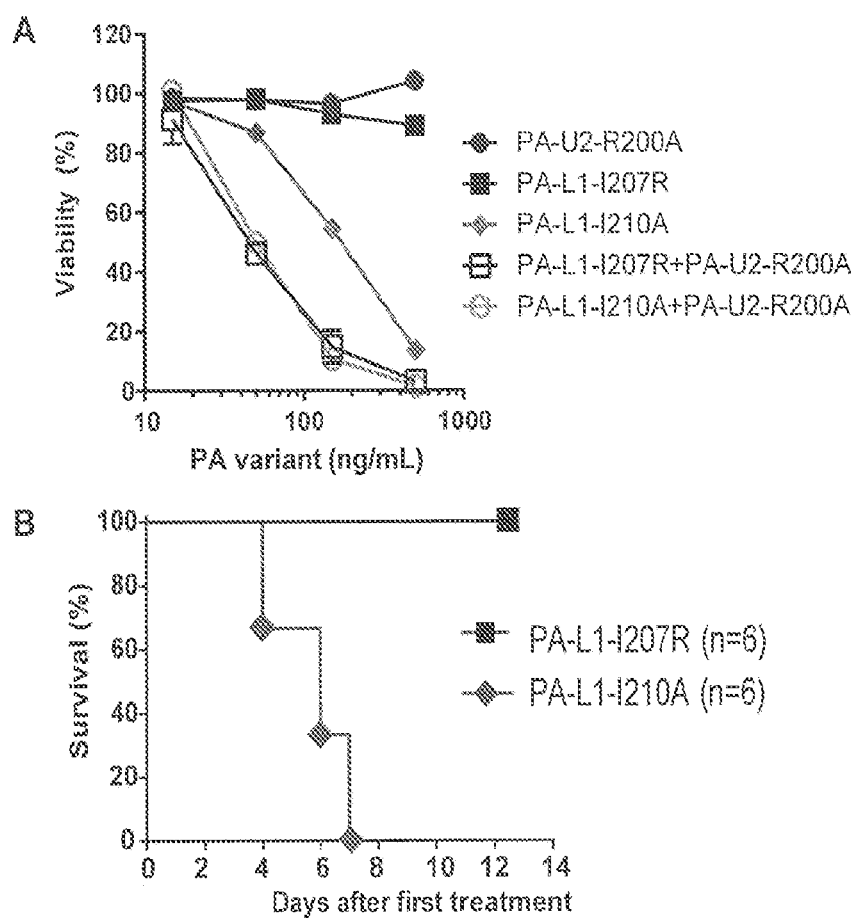
FIG. 4A is a graph showing the viability (%) of B16-BL6 cells treated with various concentrations (ng/mL) of PA variants PA-U2-R200A (closed circles), PA-L1-I207R (closed squares), PA-L1-I210 OA (diamonds), PA-L1-I207R+PA-U2-R200A (open squares), PA-L1-I210A+PA-U2-R200A (open circles).

FIG. 4B is a graph showing the survival of C57BL/6J mice injected intraperitoneally with three doses of 20 µg PA-L1-I207R (squares) or PA-L1-I210A (diamonds) plus 10 gig FP59 at days 0, 1 and 2.

Figure 5:
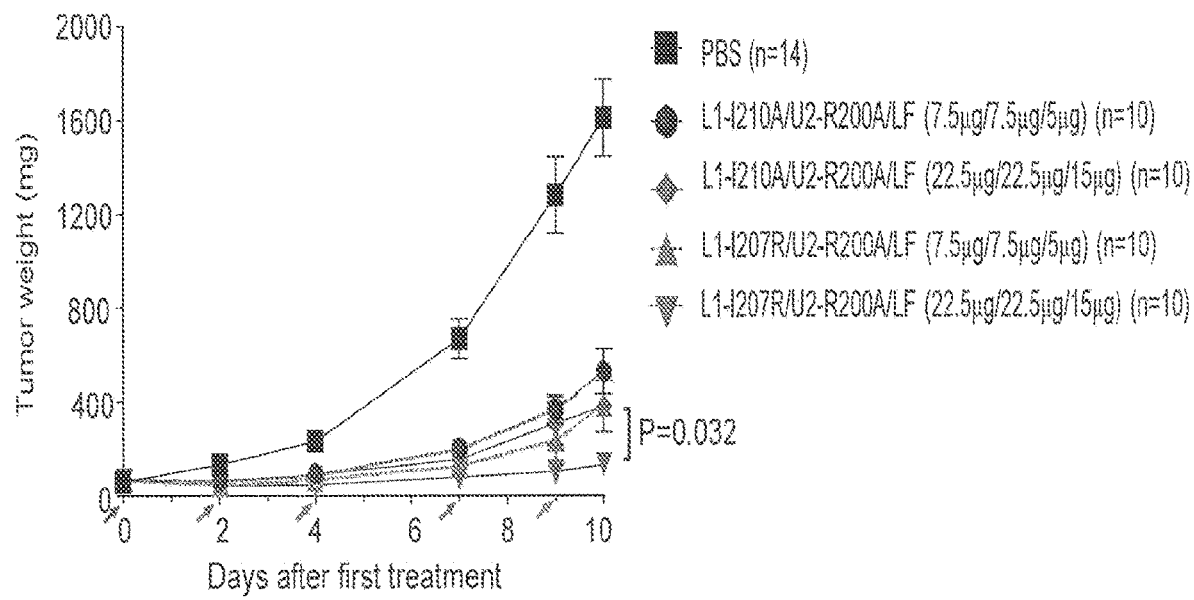

FIG. 5 is a graph showing the tumor weight (mg) in B16-BL6 tumor-bearing mice treated intraperitoneally with phosphate buffered saline (PBS) (squares), L1-I210A/U2-R200A/LF (7.5 µg/7.5 µg/5 µg) (circles), L1-I210A/U2-R200A/LF (22.5 µg/22.5 µg/15 µg) (diamonds), L1-I207R/U2-R200A/LF (7.5 µg/7.5 µg/5 µg) (▲), or L1-I207R/U2-R200A/LF (22.5 µg/22.5 µg/15 µg) (▼). Doses were administered on each of the five days shown by the arrows.

Figure 6:
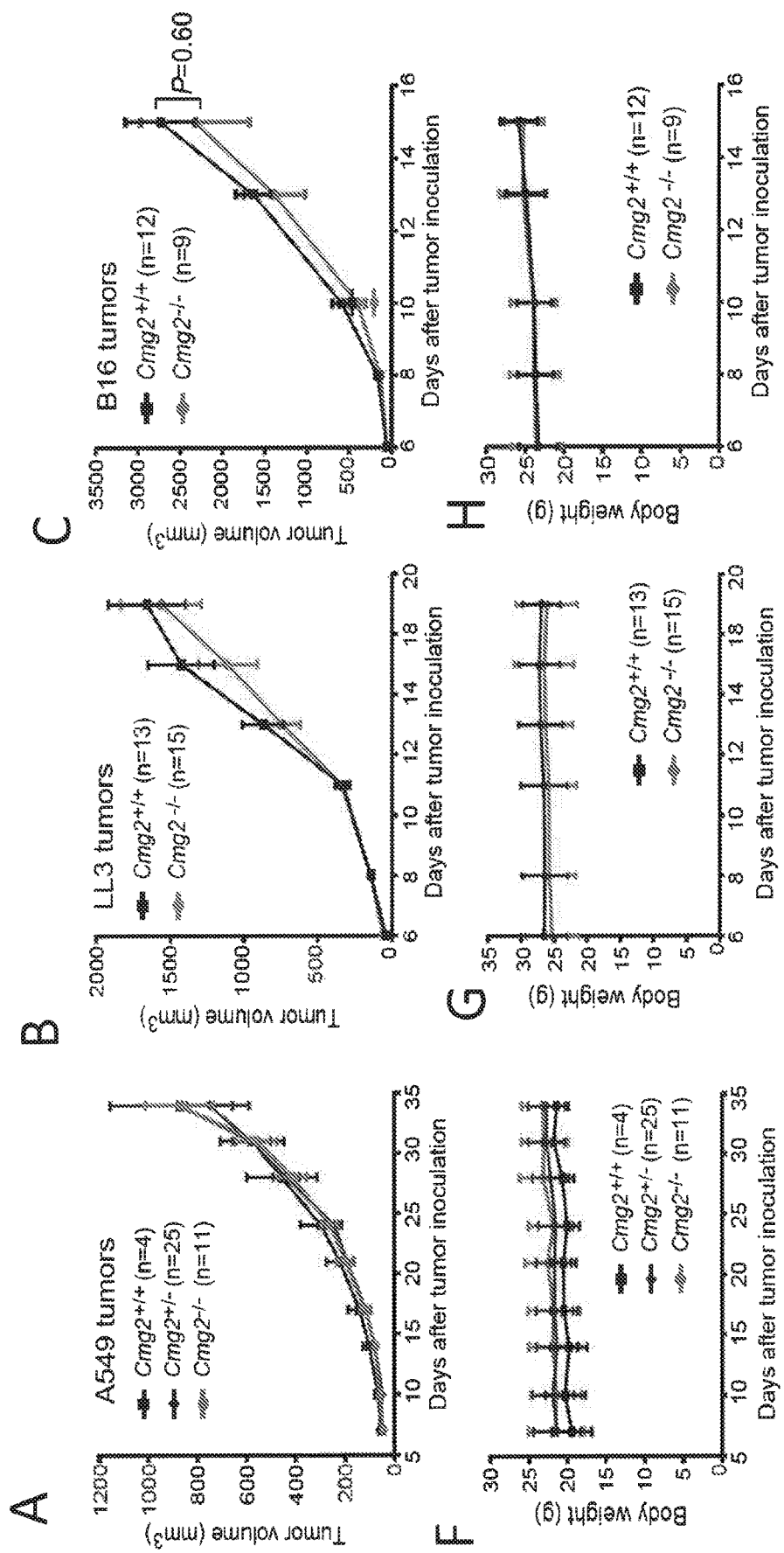
Figure 6:
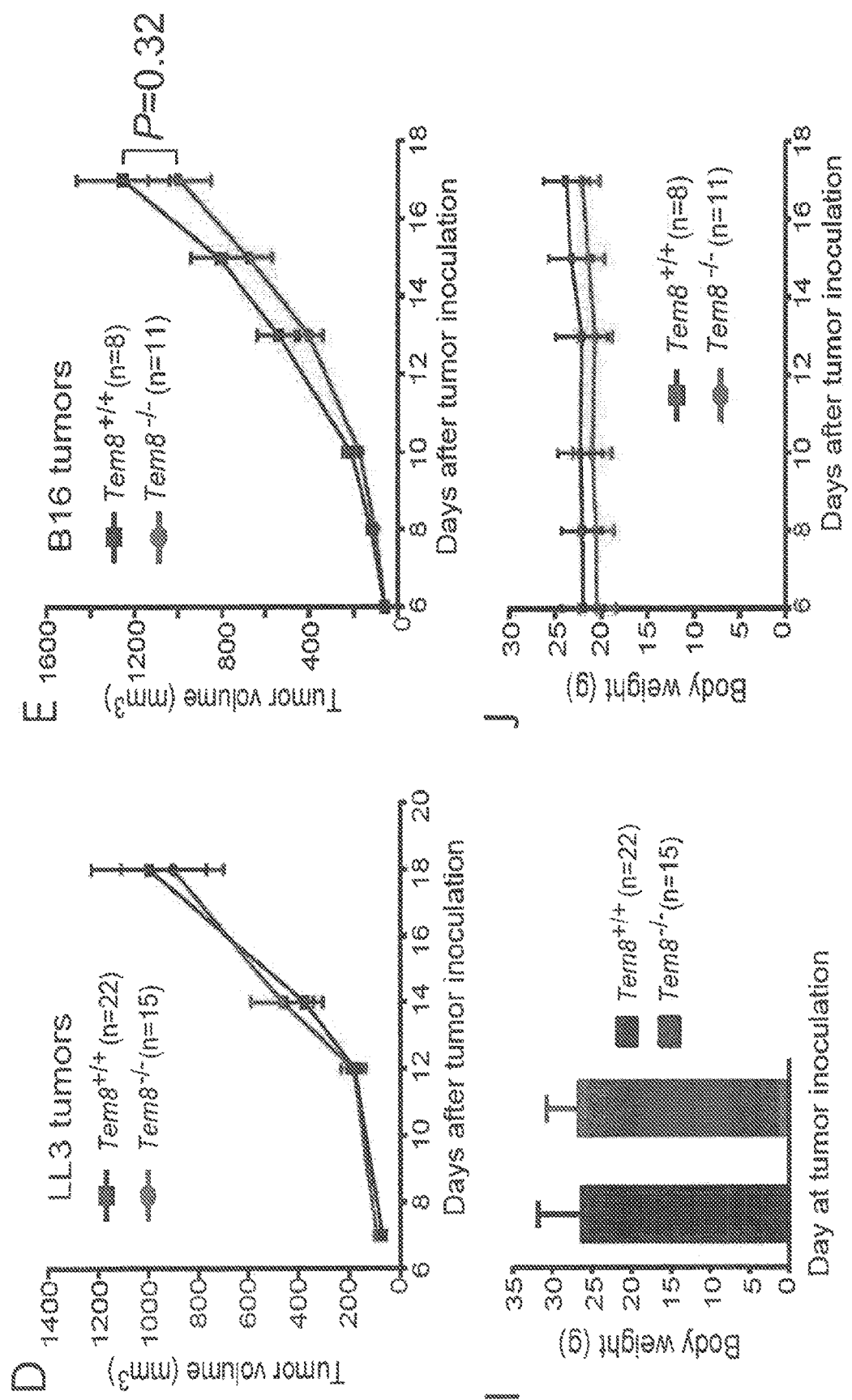

FIGS. 6A-6C are graphs showing the tumor volume ($mm^3$) (mean±SE) in $Cmg2^{+/+}$ (squares), $Cmg2^{+/-}$ (diamonds), or $Cmg2^{-/-}$ (circles) mice bearing A549 (A), LL3 (B), or B16 (C) tumors at various time points (days) after inoculation.

FIGS. 6D-6E are graphs showing the tumor volume ($mm^3$) (mean±SE) of $Tem8^{-/-}$ mice (circles) and littermate $Tem8^{+/+}$ mice (squares) bearing LL3 (D) or B16 (E) tumors at various time points (days) after inoculation.

FIGS. 6F-6H are graphs showing the body weight (g) (mean±SD) in $Cmg2^{+/+}$ (squares), $Cmg2^{+/-}$ (diamonds), or $Cmg2^{-/-}$ (circles) mice bearing A549 (F), LL3 (G), or B16 (H) tumors at various time points (days) after inoculation.

FIG. 6I is a graph showing the body weight (g) (mean±SD) of Tem8$^{-/-}$ mice (grey bars) and littermate Tem8$^{+/+}$ mice (black bars) bearing LL3 tumors the day when tumor cells were inoculated.

FIG. 6J is a graph showing the body weight (g) (mean±SD) of Tem8$^{-/-}$ mice (circles) and littermate Tem8$^{+/+}$ mice (squares) bearing B16 tumors at various time points (days) after inoculation.

Figure 7:
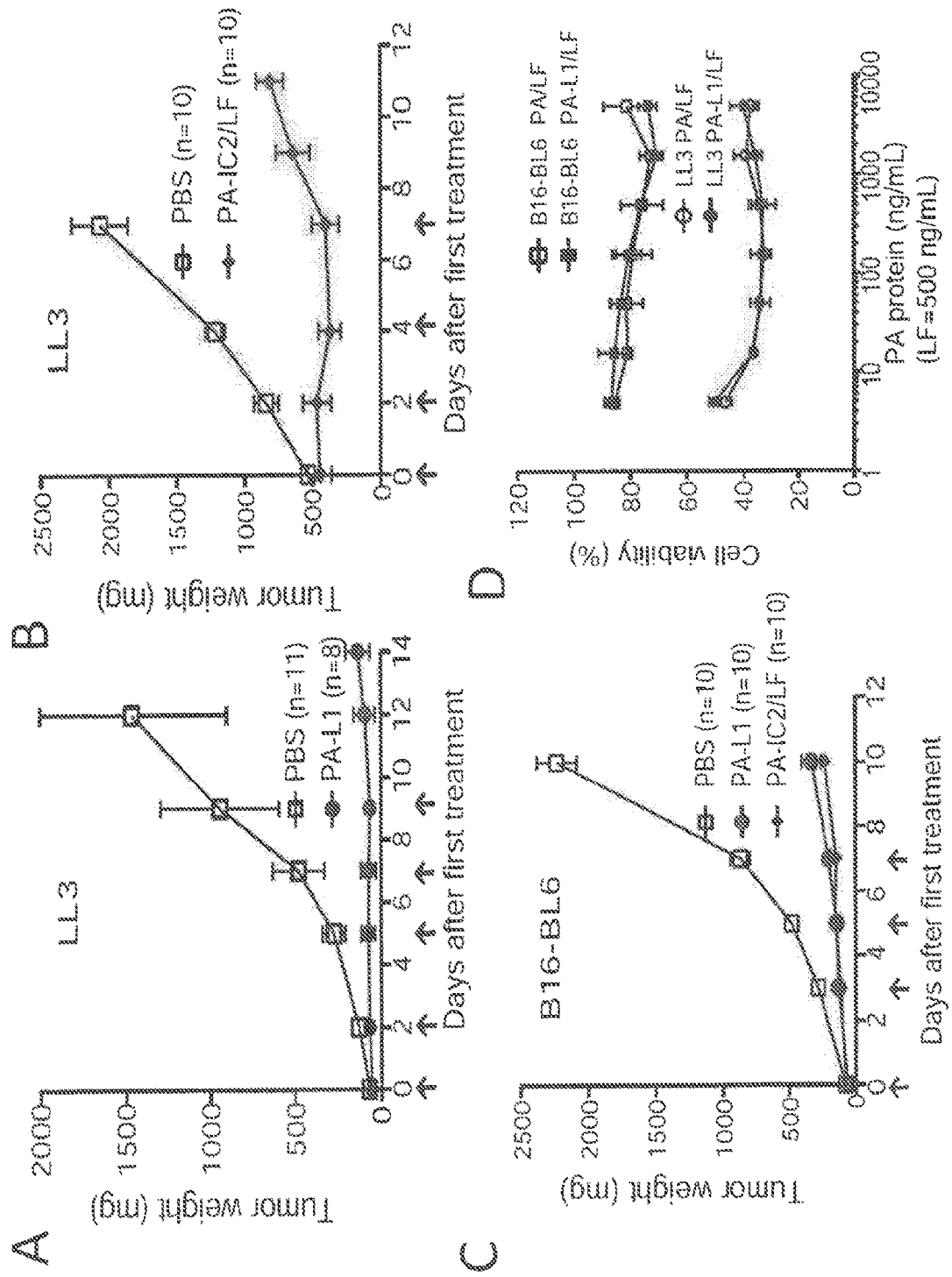
Figure 7:
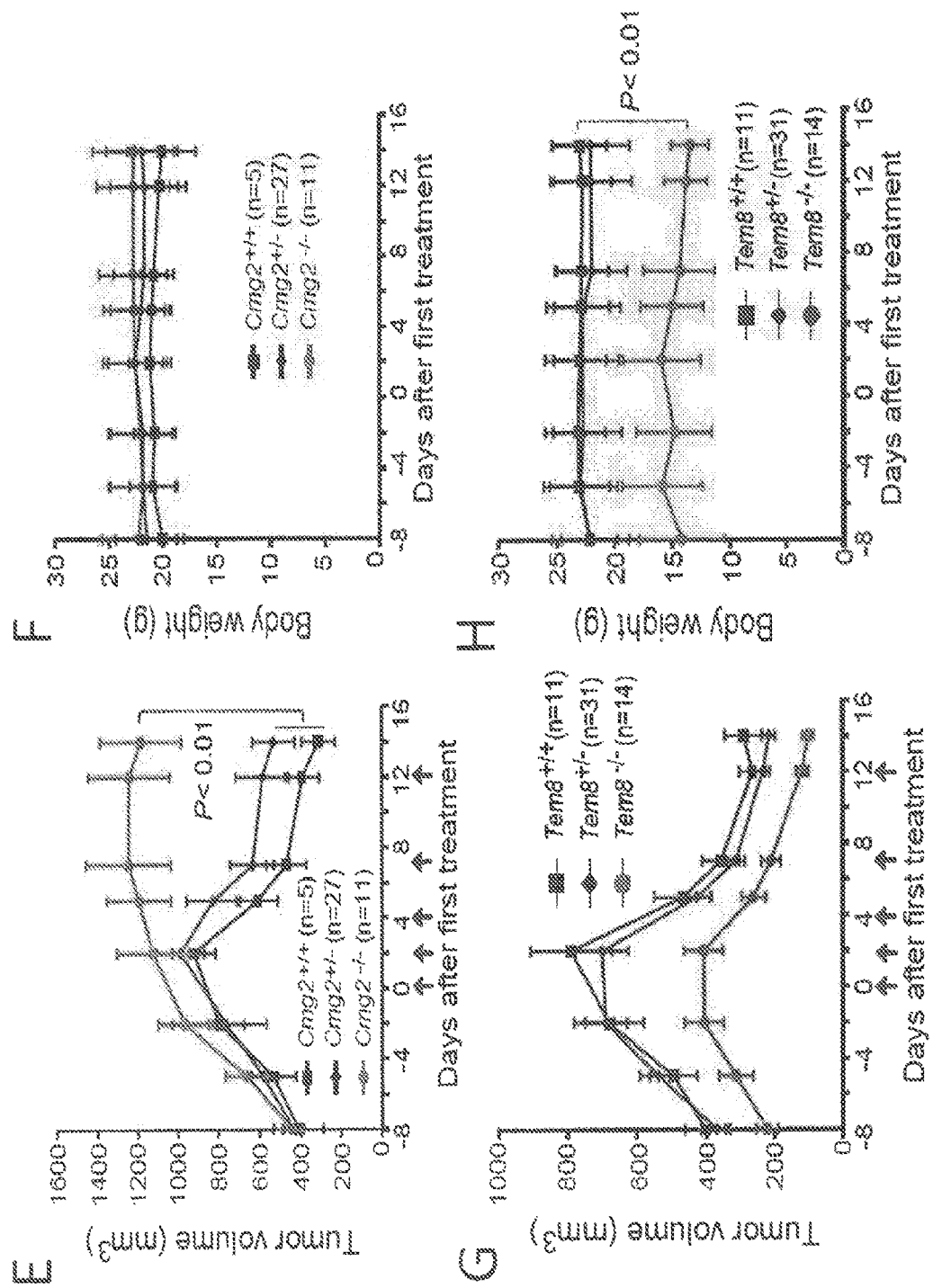

FIGS. 7A and 7B are graphs showing the tumor volume (mm$^3$) (mean±SE) of LL3 tumor-bearing mice treated with PBS (squares), PA-L1 (circles) (A), or IC2-PA/LF (diamonds) (B) at various time points (days) after first treatment. The treatment was administered on the days indicted by arrows.

FIG. 7C is a graph showing the tumor volume (mm$^3$) (mean±SE) of B16-BL6 tumor-bearing mice treated with PBS (squares), PA-L1 (circles), or IC2-PA/LF (diamonds) at various time points (days) after first treatment. The treatment was administered on the days indicted by arrows.

FIG. 7D is a graph showing the cell viability (%) of LL3 cells treated with PA (open squares) or PA-L1 (closed squares) or B16-BL6 cells treated with PA (open circles) or PA-L1 (closed circles) in the presence of LF (mean±SD).

FIGS. 7E and 7F are graphs showing the tumor volume (mm$^3$) (mean±SE) (E) and body weight (g) (mean±SD) (F) of Cmg2$^{+/+}$ (squares), Cmg2$^{+/-}$ (diamonds), and Cmg2$^{-/-}$ (circles) mice treated with 15 µg PA-L1 plus 7.5 µg LF on days after the first treatment. The treatment was administered on the days indicted by arrows.

FIGS. 7G and 7H are graphs showing the tumor volume (mm$^3$) (mean±SE) (G) and body weight (g) (mean±SD) (H) of A549 tumor-bearing littermate Tem8$^{+/+}$ (squares), Tem8$^{+/-}$ (diamonds), and Tem8$^{-/-}$ (circles) mice treated with 15 µg PA-L1 plus 7.5 µg LF on days after the first treatment. The treatment was administered on the days indicted by arrows.

Figure 8:
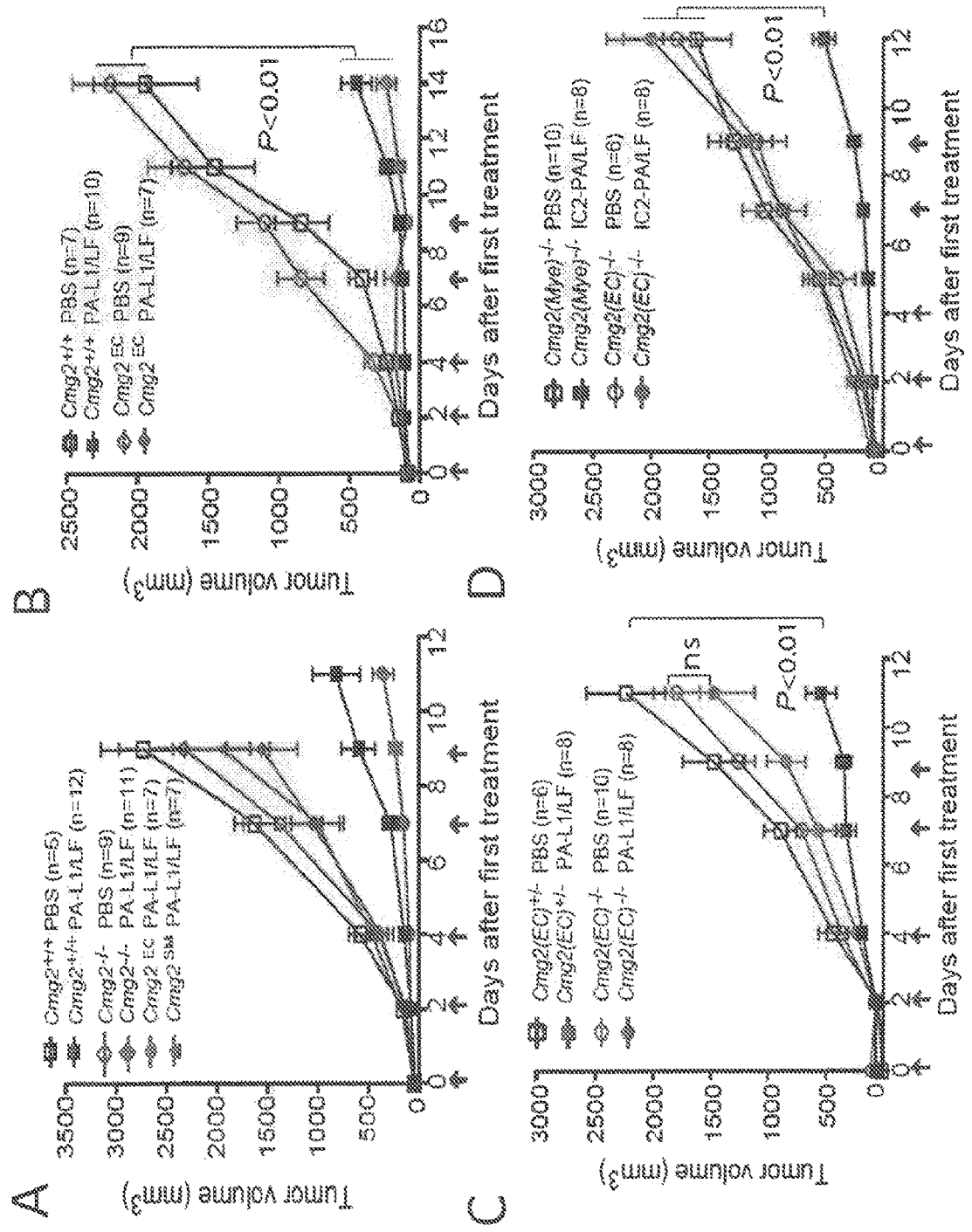
Figure 8:
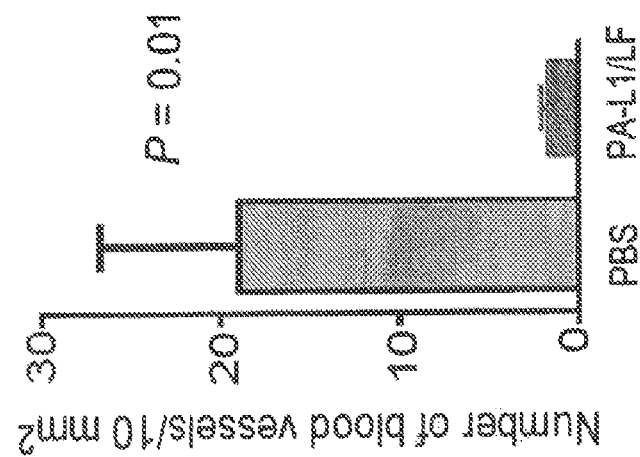
Figure 8:
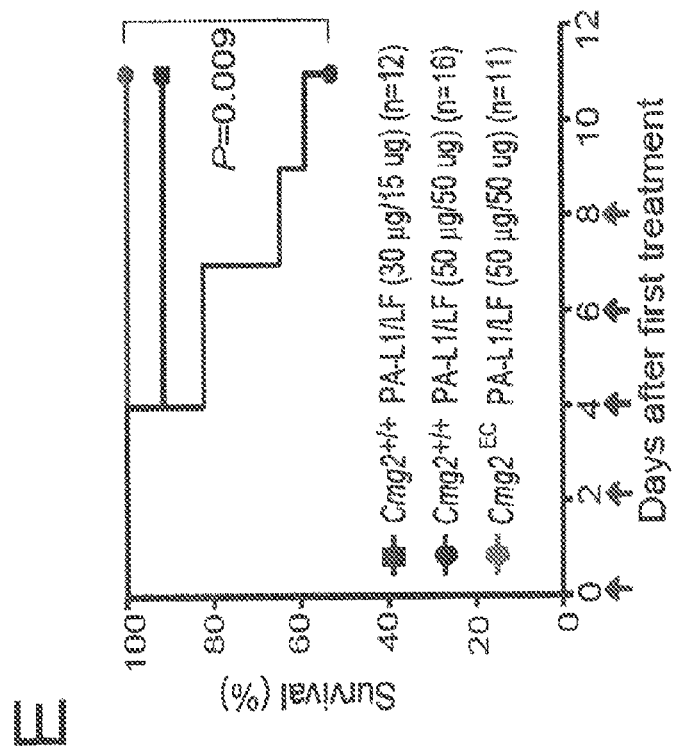

FIGS. 8A-8C are graphs showing the tumor volume (mm$^3$) (mean±SE) of B16-BL6 melanoma-bearing mice with the indicated CMG2 genotypes that were treated with 30 µg PA-L1 plus 15 µg LF on days after the first treatment. The treatment was administered on the days indicted by arrows.

FIG. 8D is a graph showing the tumor volume (mm$^3$) (mean±SE) of B16-BL6 melanoma-bearing endothelial cell-specific CMG2-null mice and myeloid-specific CMG2-null mice (Cmg2(Mye)$^{-/-}$) treated with 30 µg IC2-PA (15 µg PA-L1-I207R+15 µg PA-U2-R200A) plus 10 µg LF or PBS at the days indicated by the arrows.

FIG. 8E is a graph showing the survival (%) of WT mice and Cmg2$^{EC}$ mice that were treated with PA-L1/LF on the days indicated by arrows.

FIG. 8F is a graph showing the number of blood vessels per 10 mm$^2$ of mice treated with PBS (left bar) or 3 doses of 30 µg PA-L plus 15 µg LF (right bar) on days 0, 2, and 4.

Figure 9:
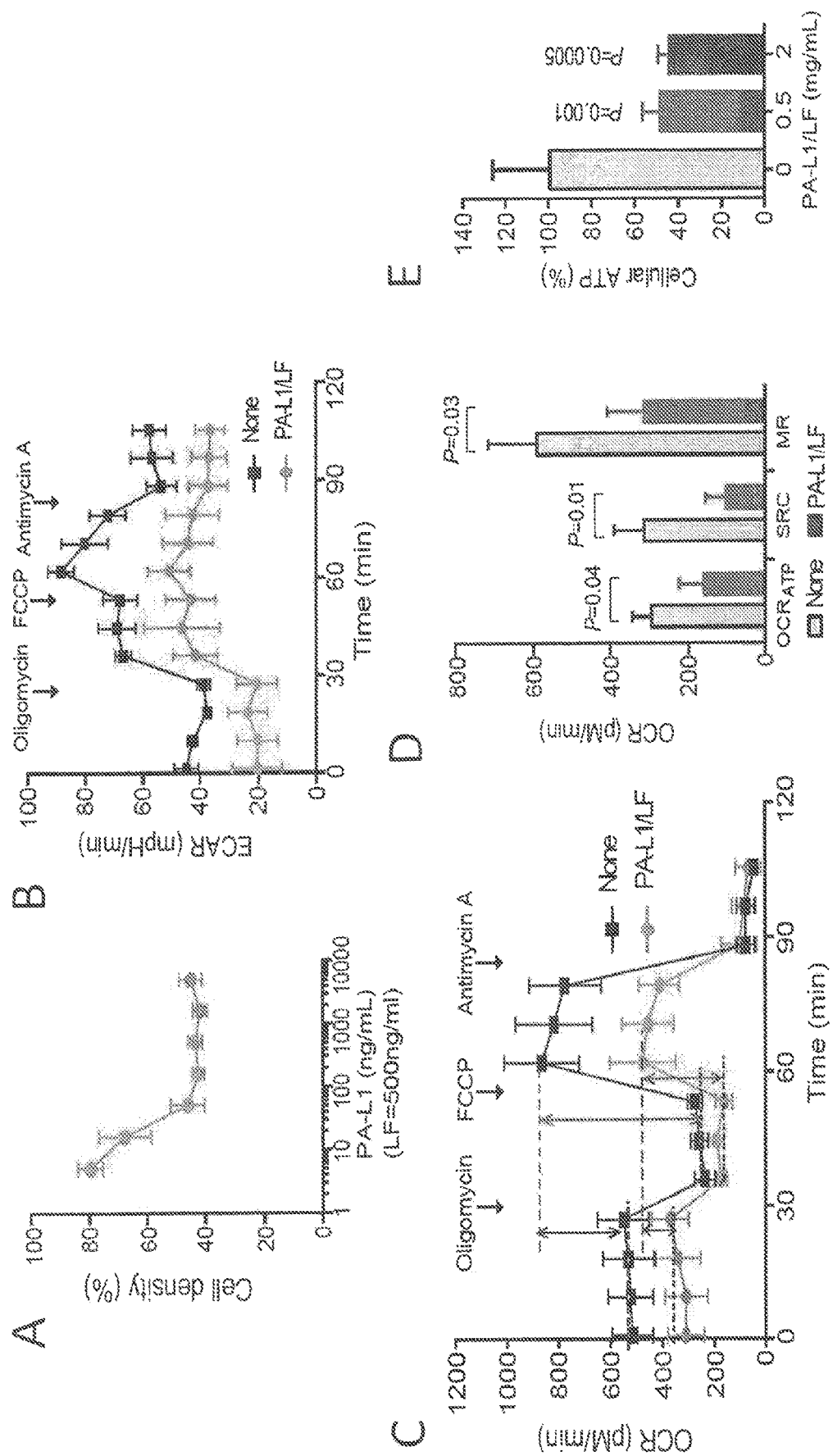
Figure 9:
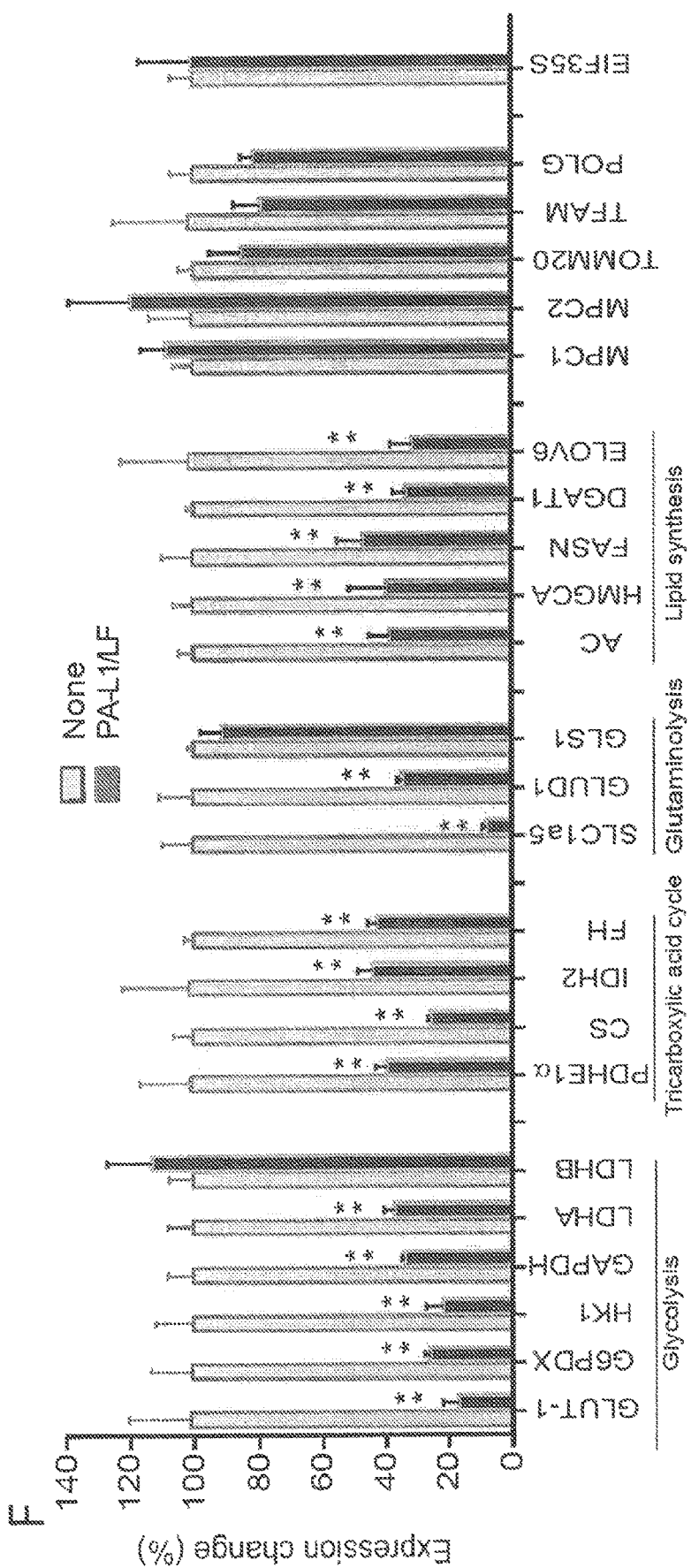

FIG. 9A is a graph showing the cell density (%) of tumor endothelial cells incubated with various concentrations of PA-L1 in the presence of LF (500 ng/mL). Data are shown as mean±SD.

FIG. 9B is a graph showing the ECAR (mpH/min) measured at various time points (min) under basal conditions or conditions following sequential additions of the mitochondrial inhibitors (oligomycin, FCCP, and antimycin A) of tumor endothelial cells treated with or without PA-L1/LF (1 µg/mL each) for 24 h. The ECAR readings were normalized to amounts of cells having 50 mg total protein, mean±SD. (n=3 independent experiments).

FIG. 9C is a graph showing the OCR (pM/min) measured at various time points (min) under basal conditions or conditions following sequential additions of the mitochondrial inhibitors (oligomycin, FCCP, and antimycin A) of tumor endothelial cells treated with or without PA-L1/LF (1 µg/mL each) for 24 h. The OCR readings were normalized to amounts of cells having 50 mg total protein, mean±SD. (n=3 independent experiments).

FIG. 9D is a graph showing (i) the OCR$_{ATP}$ obtained by subtracting the OCRs after addition of oligomycin from the basal OCRs of the endothelial cells, (ii) spare respiratory capacity (SRC), and (iii) the maximal respiration (MR) values of cells treated with (dark grey bars) or without (light grey bars) PA-L/LF (1 µg/mL each). Data are shown as mean±SD.

FIG. 9E is a graph showing the relative cellular ATP levels of tumor endothelial cells treated with PA-L1/LF (0.5 µg/mL or 2 µg/mL each) for 24 h vs. untreated cells. Data are shown as mean±SD.

FIG. 9F is a graph showing the change in expression (%) of the indicated genes in tumor endothelial cells treated with or without PA-L1/LF (1 µg/mL each) for 24 h. Eukaryotic translation initiation factor EIF35S was used as an internal normalization control. *, P<0.05; ***, P<0.01.

Figure 10:
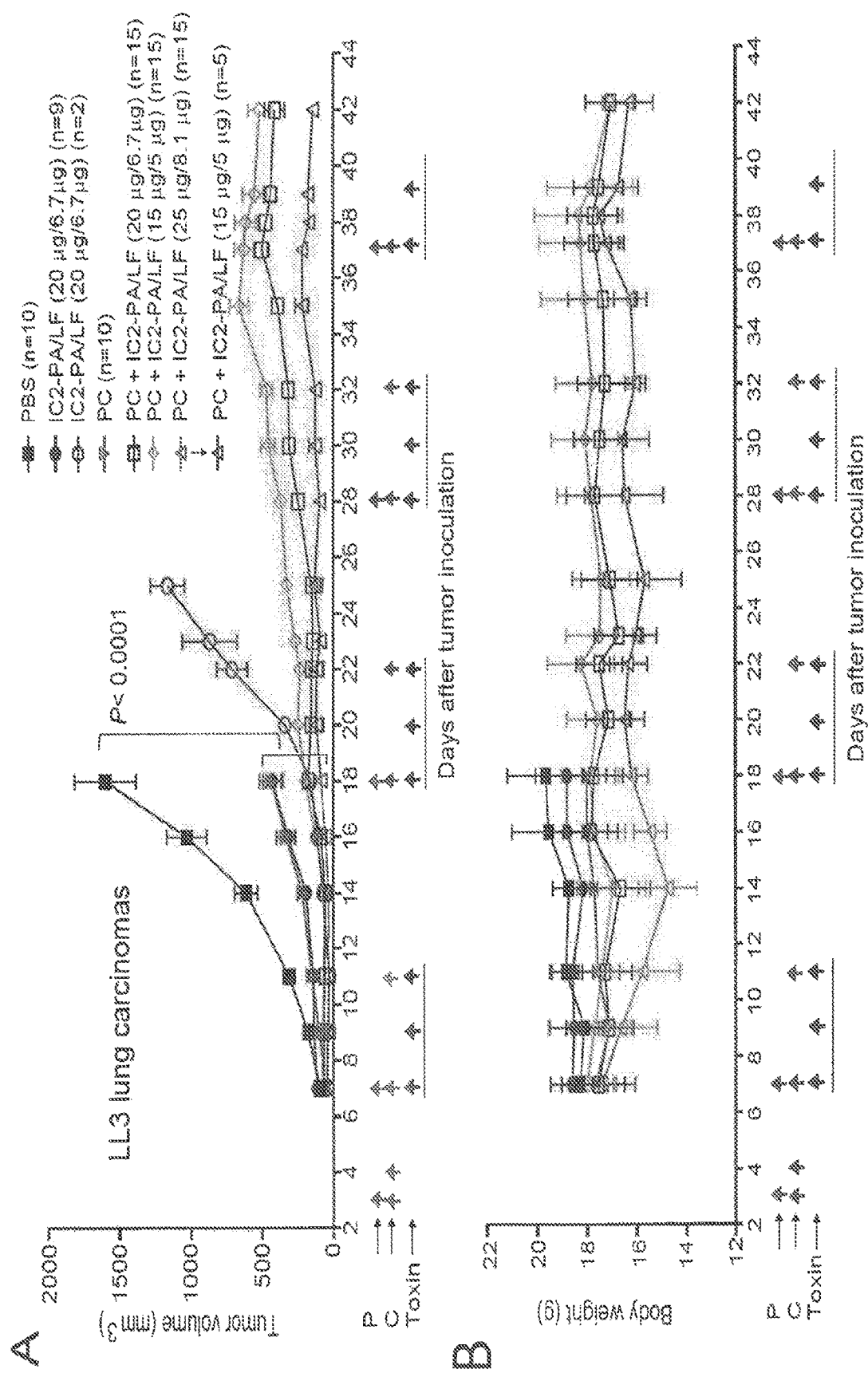
Figure 10:
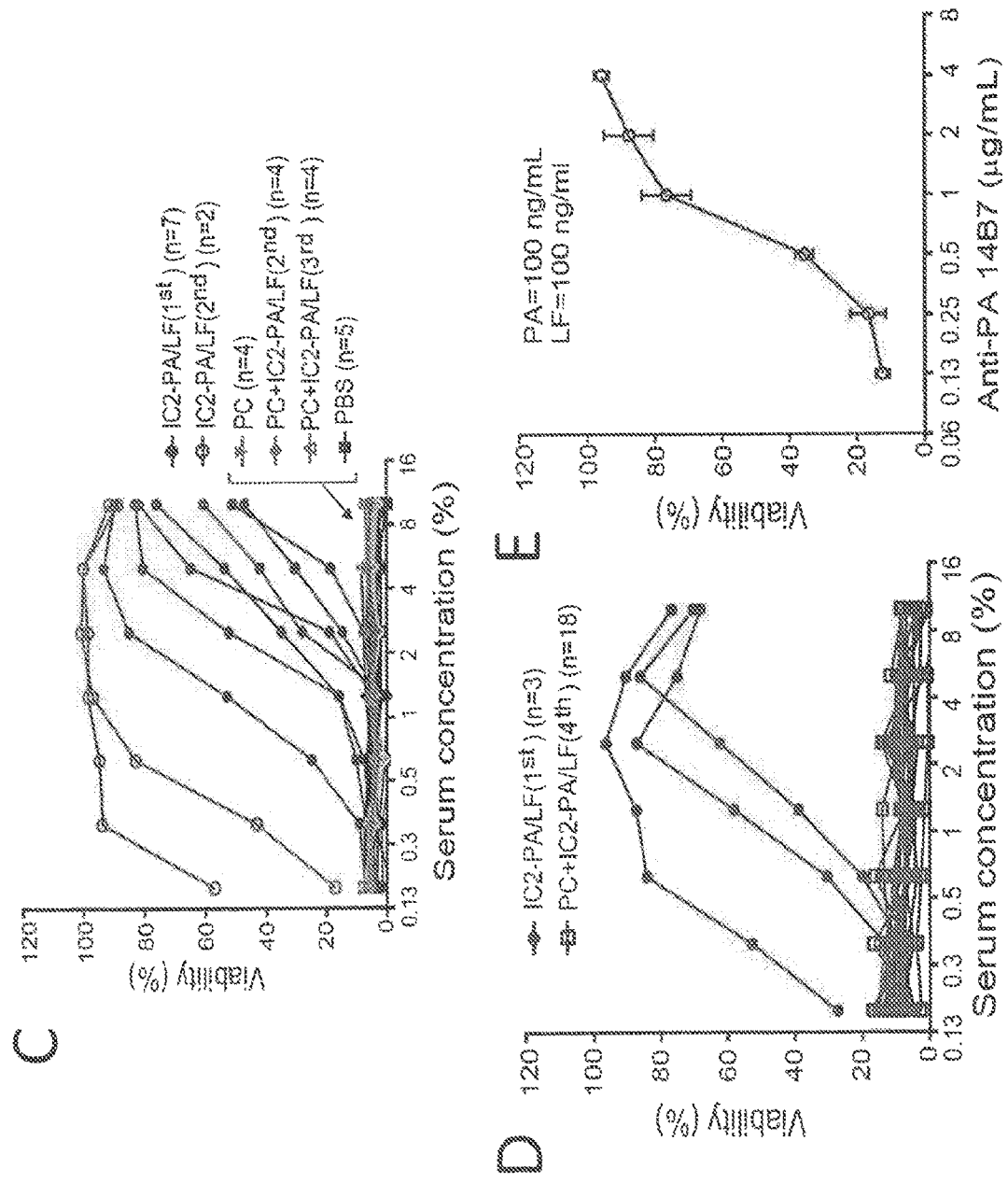

FIGS. 10A and 10B are graphs showing the tumor volume (mm$^3$) (A) and body weight (g) (B) in LL3 lung carcinomas-bearing immunocompetent C57BL/6 mice that were treated with PBS (closed squares), IC2-PA/LF (20 µg/6.7 µg) (* and open circles), PC regimen (1 mg pentostatin and 50 mg cyclophosphamide) (▽), high (25 µg/8.1 µg) (△), medium (20 µg/6.7 µg) (open squares), or low (15 µg/5 µg) (diamonds and ▲) doses of IC2-PA/LF combined with PC regimen at various time points (days) after tumor inoculation. Schedules for PC and the toxin treatments are indicated by the arrows. Tumor weights, mean±SE. Body weights, mean±SD.

FIG. 10C is a graph showing the viability (%) of RAW264.7 cells that were incubated with IC2-PA/LF (100 ng/mL each) for 5 h in the presence of various dilutions of sera obtained from representative mice in FIGS. 10A and 10B after the 1$^{st}$ (closed circles) or 2$^{nd}$ (open circles) round of therapy. The viability of cells treated with PC and IC2-PA/LF after the 2$^{nd}$ (diamonds) or 3$^{rd}$ (△) round of therapy, PC (▼), or PBS (squares) are also shown.

FIG. 10D is a graph showing the viability (%) of RAW264.7 cells that were incubated with IC2-PA/LF (100 ng/mL each) for 5 h in the presence of various dilutions of sera obtained from representative mice in FIGS. 10A and 10B after the 1$^{st}$ round of therapy (circles). The viability of cells treated with PC and IC2-PA/LF after the 4$^{th}$ round of therapy (squares) is also shown.

FIG. 10E is a graph showing the viability (%) of cells treated as described in FIGS. 10A-10D using various concentrations of 14B7 anti-PA monoclonal antibodies as a positive control for neutralizing antibodies.

FIGS. 11A-11D are graphs showing the number of cells (millions) isolated from B16-BL6 melanoma-bearing mice that were positive for the indicated B-cell (A), T-cell (B and C), or granulocyte markers (D) after the 2$^{nd}$ cycle of therapy with PBS (grey bars), PC (black bars), IC2-PA/LF (right striped bars), or the combined PC and the toxin (left striped bars) as measured by flow cytometry. Naïve, untreated cells (white bars) were measured as a control.

Figure 11:
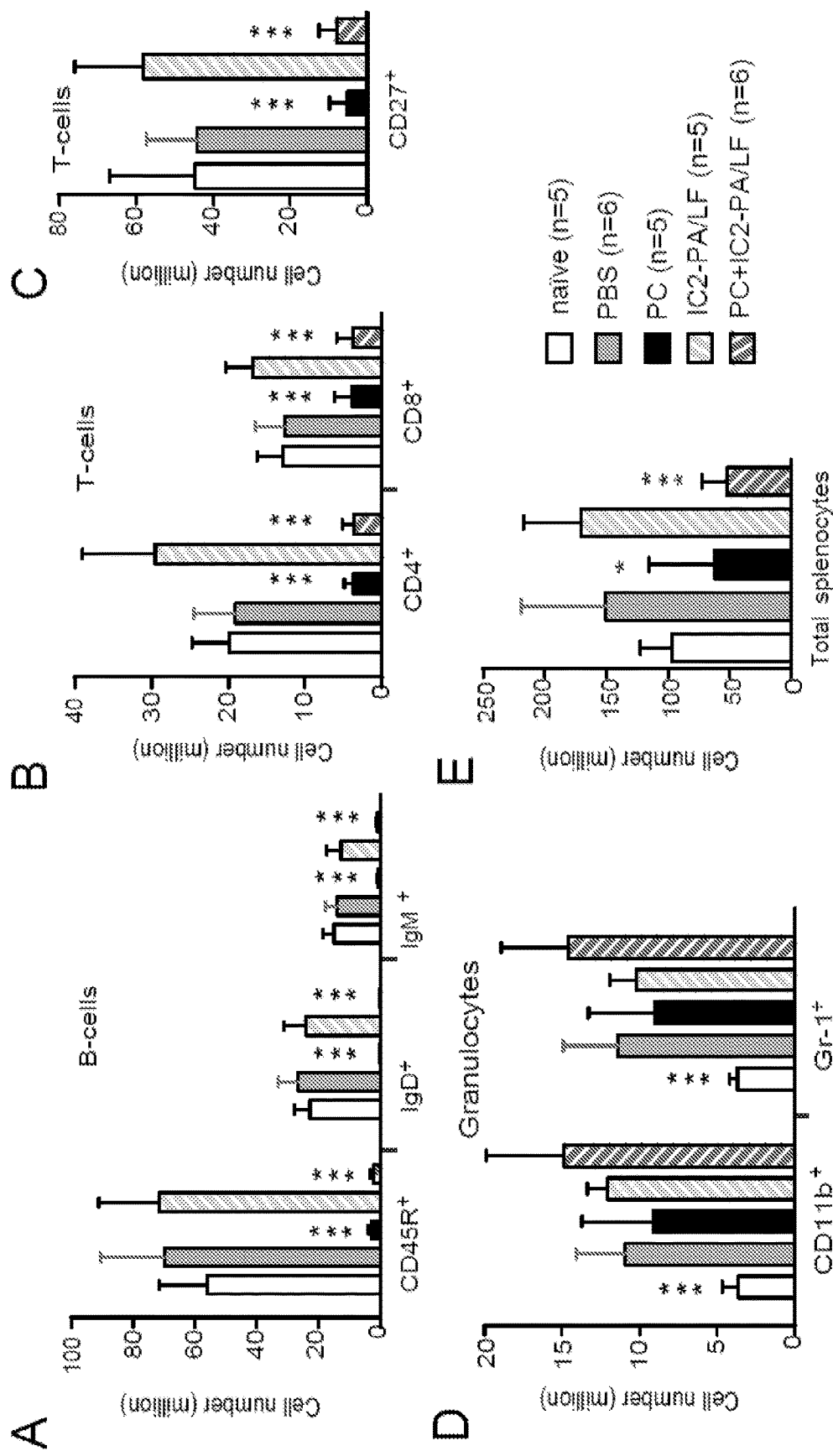

FIG. 11E is a graph showing the total splenocyte count (millions) of the mice treated in FIGS. 11A-11D.

Figure 12:
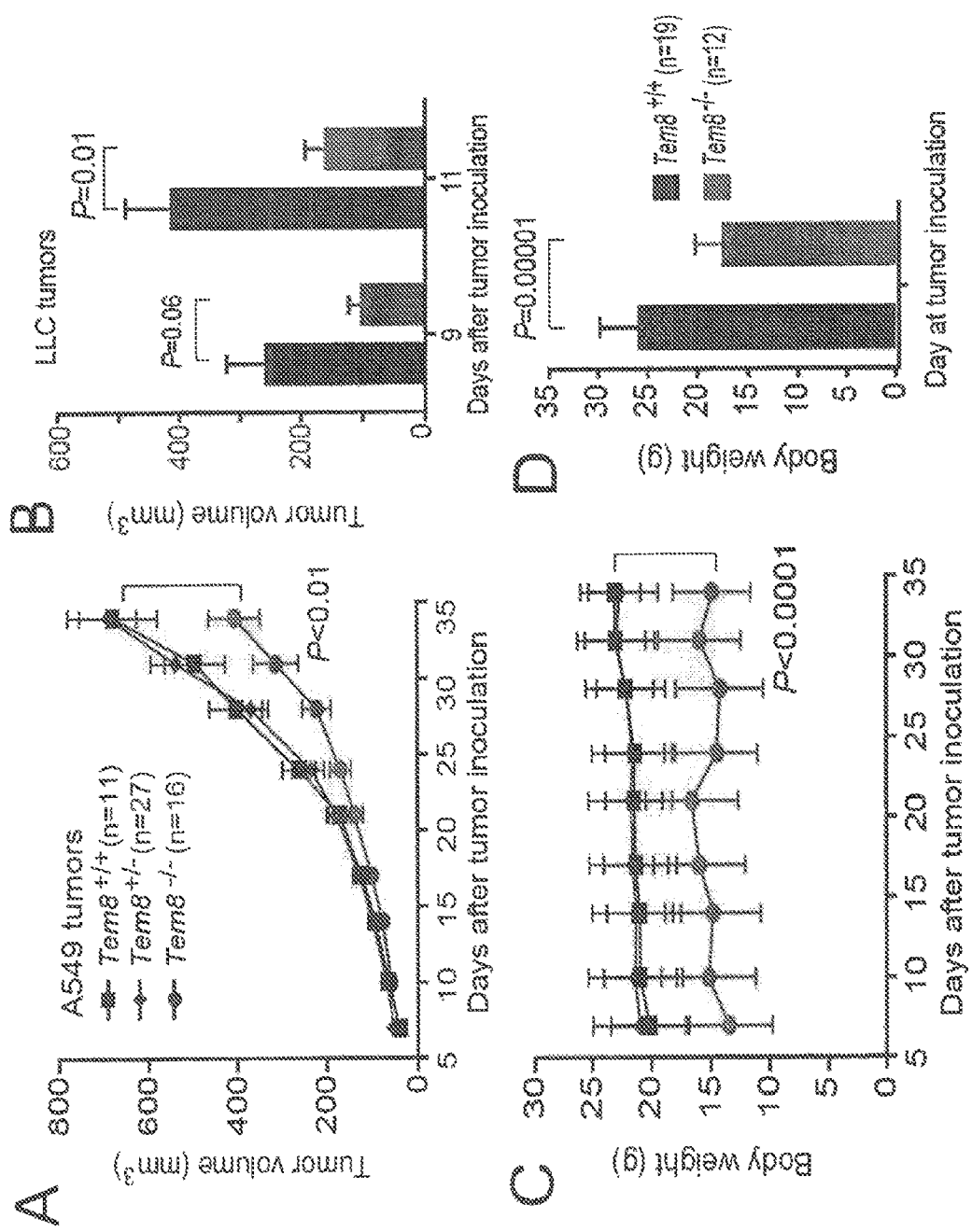
Figure 12:
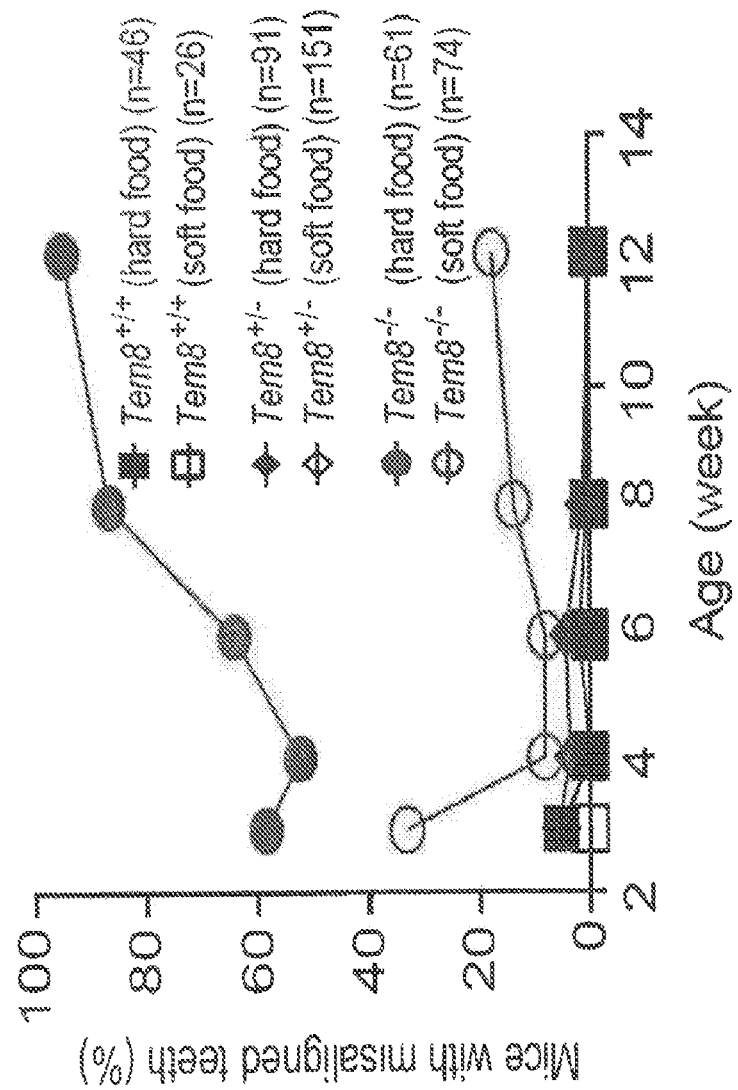
Figure 12:
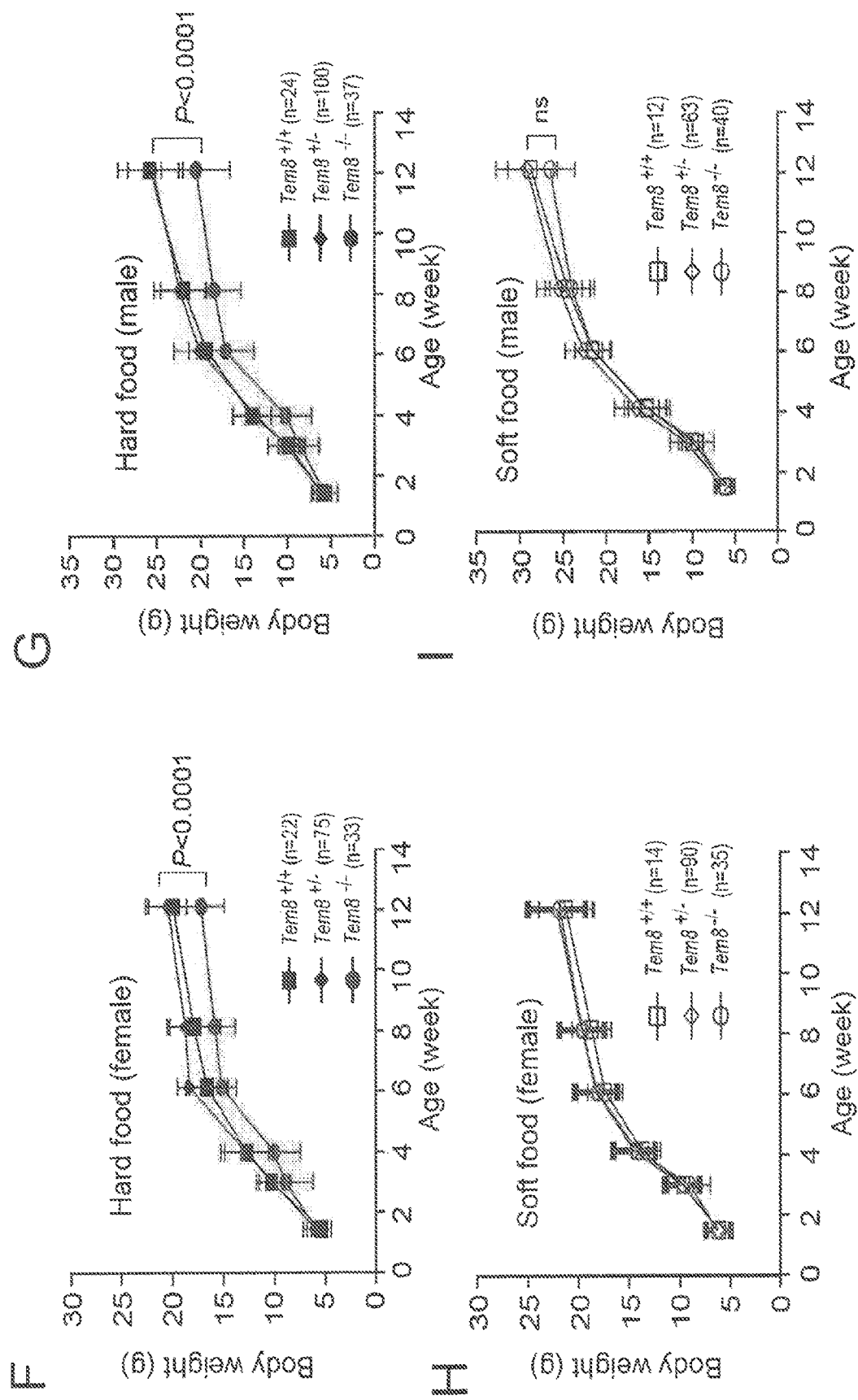

FIG. 12A is a graph showing the tumor volume (mm$^3$) (mean±SE) of Tem8$^{-/-}$ mice (circles), Tem8$^{+/-}$ mice (diamonds), Tem8$^{+/+}$ mice (squares) bearing A549 tumors at various time points (days) after inoculation.

FIG. 12B is a graph showing the tumor volume (mm$^3$) (mean±SE) of Tem8$^{-/-}$ mice (grey bars) and Tem8$^{+/+}$ mice (black bars) bearing LL3 tumors at various time points (days) after inoculation.

FIG. 12C is a graph showing the body weight (g) (mean±SD) of Tem8$^{-/-}$ mice (circles), Tem8$^{+/-}$ mice (diamonds), Tem8$^{+/+}$ mice (squares) bearing A549 tumors at various time points (days) after inoculation.

FIG. 12D is a graph showing the body weight (g) (mean±SD) of Tem8$^{-/-}$ mice (grey bars) and Tem8$^{+/+}$ mice (black bars) bearing LL3 tumors at various time points (days) after inoculation.

FIG. 12E is a graph showing the percentage of mice with misaligned teeth having the following genotypes and fed the following foods: Tem8$^{+/+}$ (hard food) (n=46) (closed squares); Tem8$^{+/+}$ (soft food) (n=26) (open squares); Tem8$^{+/-}$ (hard food) (n=91) (closed diamonds); Tem8$^{-/-}$ (hard food) (n=61) (open diamonds); Tem8$^{+/-}$ (soft food) (n=151) (closed circles); and Tem8$^{-/-}$ (soft food) (n=74) (open circles).

FIGS. 12F and 12G are graphs showing the body weight of female (F) and male (G) mice that were fed hard food and which had the following genotypes: Tem8$^{+/+}$ (squares); Tem8$^{+/-}$ (diamonds); and Tem8$^{-/-}$ (circles).

FIGS. 12H and 12I are graphs showing the body weight of female (H) and male (I) mice that were fed soft food and which had the following genotypes: Tem8$^{+/+}$ (squares); Tem8$^{+/-}$ (diamonds); and Tem8$^{-/-}$ (circles).

Figure 13:
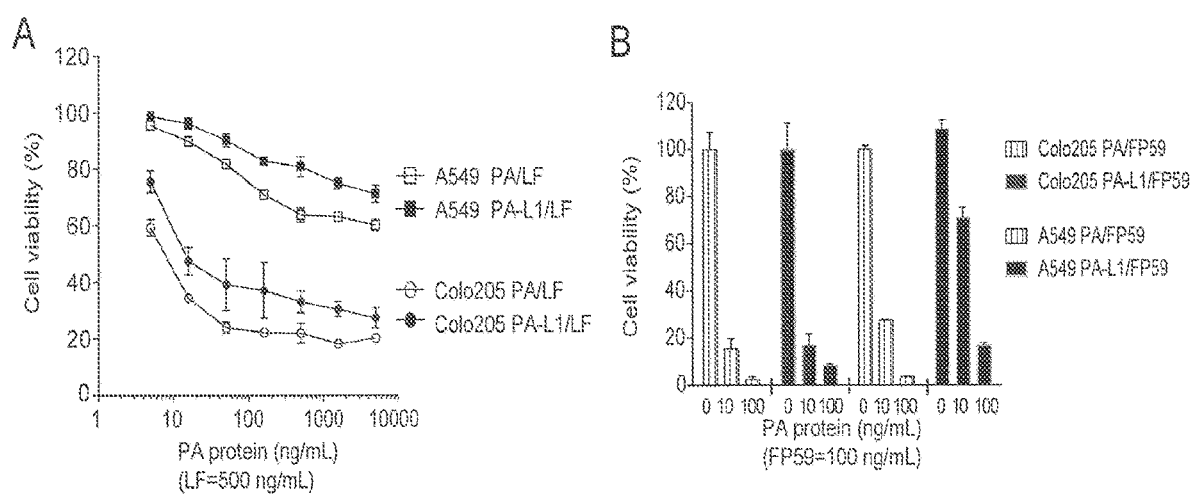

FIG. 13A is a graph showing the viability (%) of cells treated with LF and various concentrations of PA. The cell types and treatments were as follows: A549 cells treated with PA/LF (open squares); A549 cells treated with PA-L1/LF (closed squares); Colo205 cells treated with PA/LF (open circles); and Colo205 cells treated with PA-L1/LF (closed circles).

FIG. 13B is a graph showing the viability (%) of cells treated with FP59 and various concentrations of PA. The cell types and treatments were as follows: A549 cells treated with PA/FP59 (striped bars right of dotted line); A549 cells treated with PA-L1/FP59 (shaded bars right of dotted line); Colo205 cells treated with PA/FPS9 (striped bars left of dotted line); and Colo205 cells treated with PA-L1/FP59 (shaded bars left of dotted line).

Figure 14:
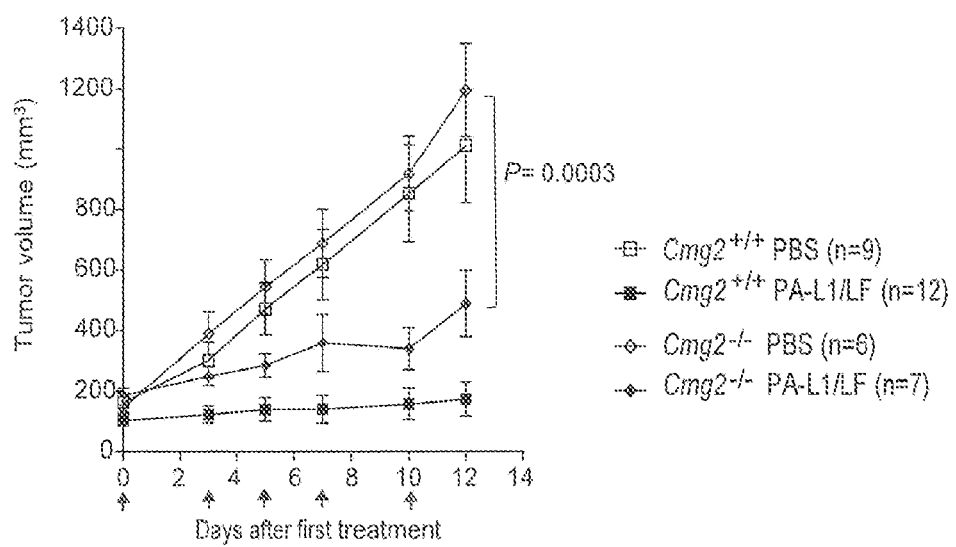

FIG. 14 is a graph showing the Colo205 tumor volume (mm$^3$) in mice at various time points (days) after first treatment. Treatments were administered on the days indicated by arrows. The genotypes and treatments were as follows: Cmg2$^{+/+}$ mice treated with PBS (open squares); Cmg2$^{+/+}$ mice treated with PA-L1/LF (closed squares); Cmg2$^{-/-}$ treated with PBS (open diamonds); and Cmg2$^{-/-}$ mice treated with PA-L1/LF (closed diamonds).

Figure 15:
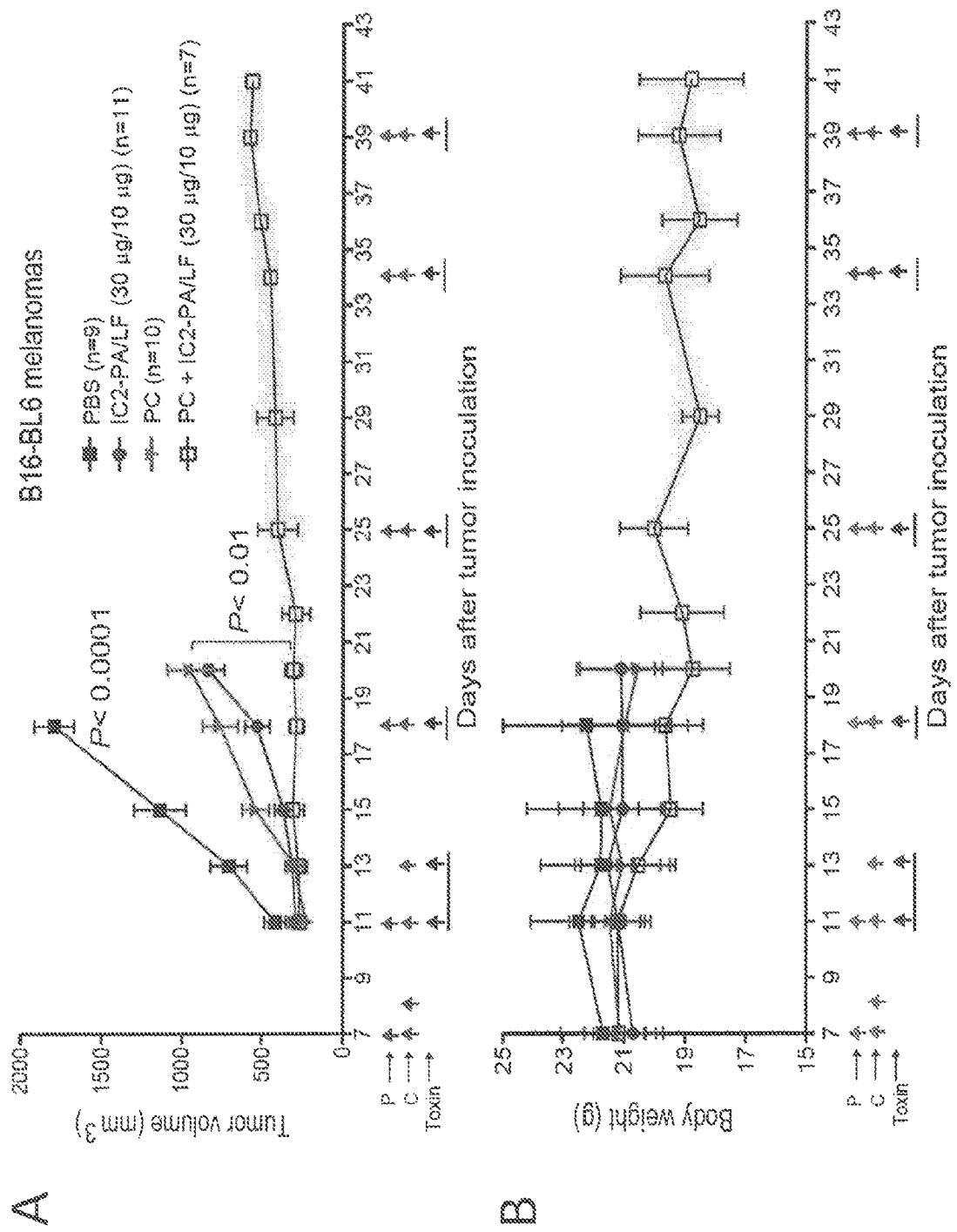
Figure 15:
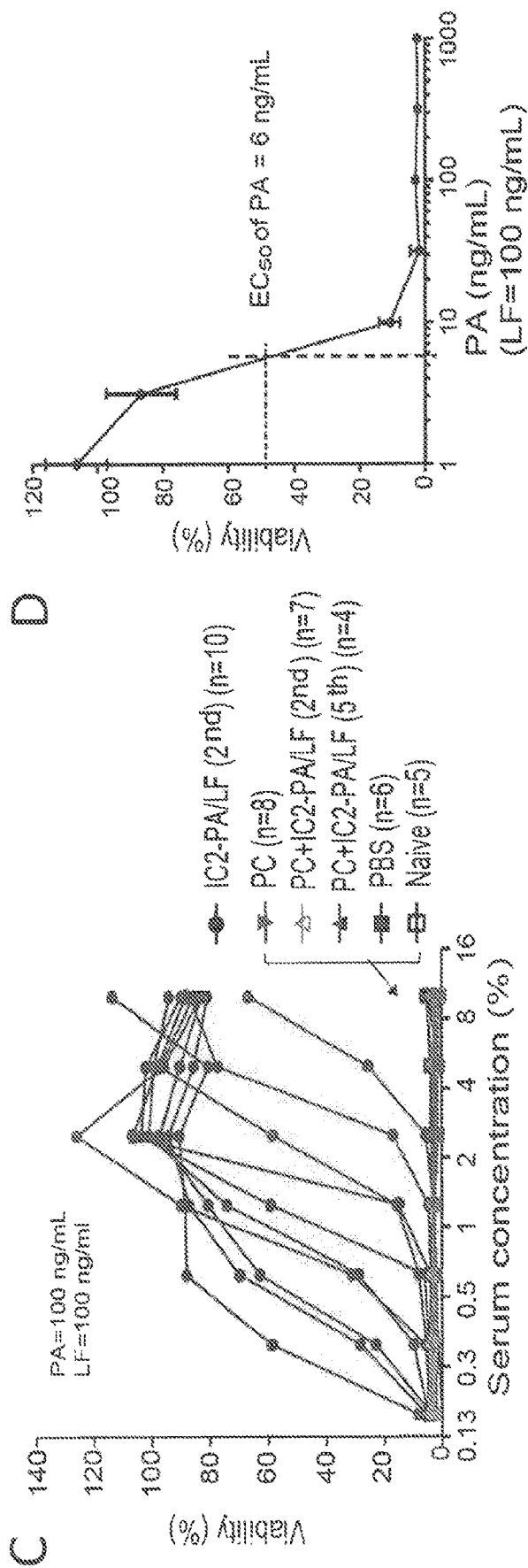

FIGS. 15A and 15B are graphs showing the tumor volume (mm$^3$) (A) and body weight (g) (B) in mice bearing B16-BL6 melanoma tumors receiving the indicated treatments at various time points (days) after tumor inoculation. The treatments were given on the days indicated by arrows. The treatments were as follows: PBS (closed squares); IC2-PA/LF (circles); PC (triangles); and PC+IC2-PA/LF (open squares).

FIG. 15C is a graph showing the viability (%) of cells that were incubated with the indicated treatments in the presence of various dilutions of sera obtained from representative mice in FIGS. 15A and 15B after the indicated round of therapy. The treatments and the rounds of therapy were as follows: IC2-PA/LF (2nd) (circles); PC (▼); PC+IC2-PA/LF (2nd) (Δ); PC+IC2-PA/LF (5th) (▲); PBS (closed squares); and naïve (untreated) (open squares).

FIG. 15D is a graph showing the viability of cells (%) that were treated with the LF and the indicated concentrations of PA. The EC$_{50}$ of PA is 6 ng/mL.

Figure 16:
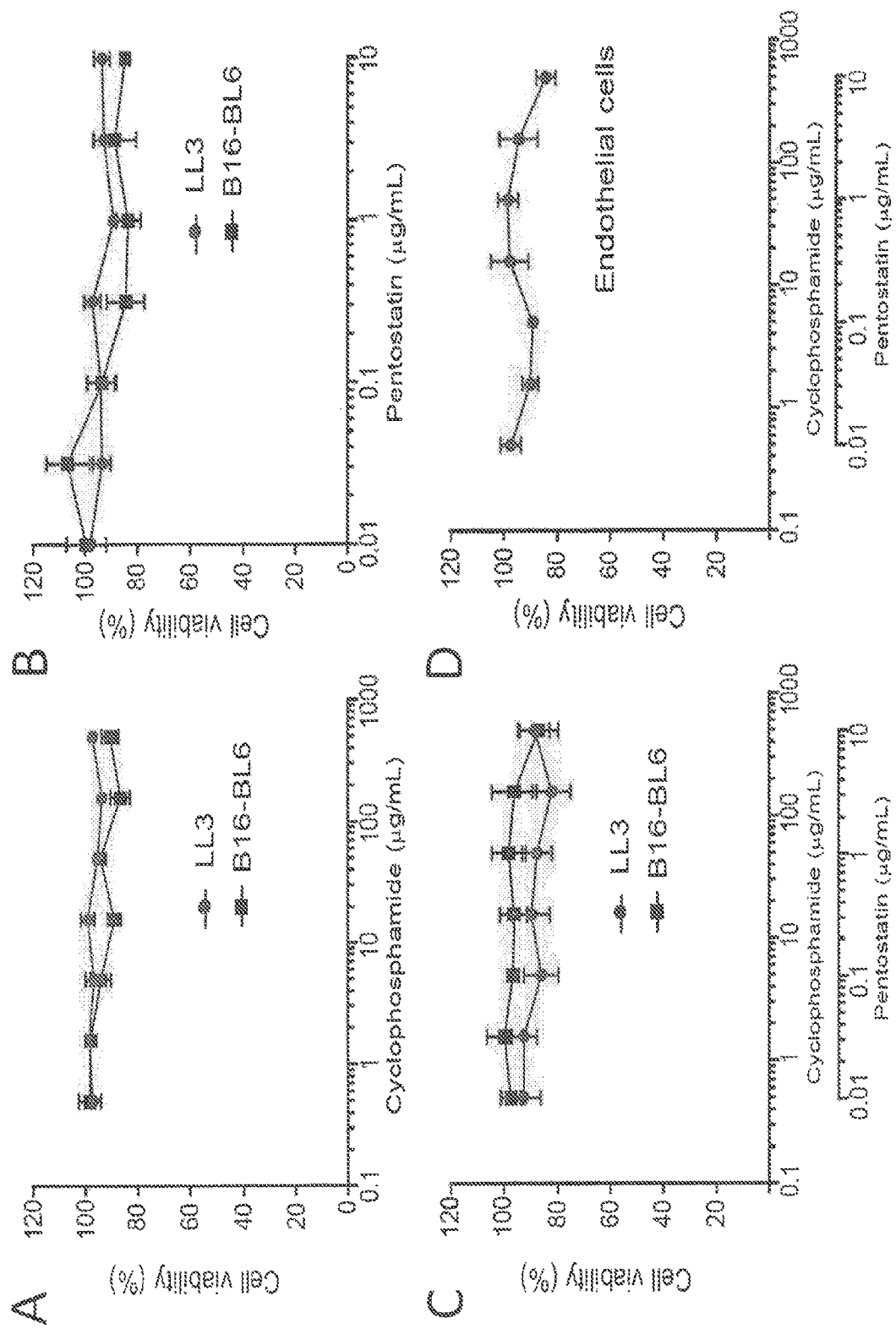

FIGS. 16A and 16B are graphs showing the viability (%) of LL3 (circles) and B16-BL cells (squares) that were treated with various concentrations of cyclophosphamide (A) or pentostatin (B).

FIG. 16C is a graph showing the viability (%) of LL3 (circles) or B16-BL cells (squares) (%) that were treated with various concentrations of pentostatin and cyclophosphamide.

FIG. 16D is a graph showing the viability (%) of endothelial cells that were treated with various concentrations of pentostatin and cyclophosphamide.

Figure 17:
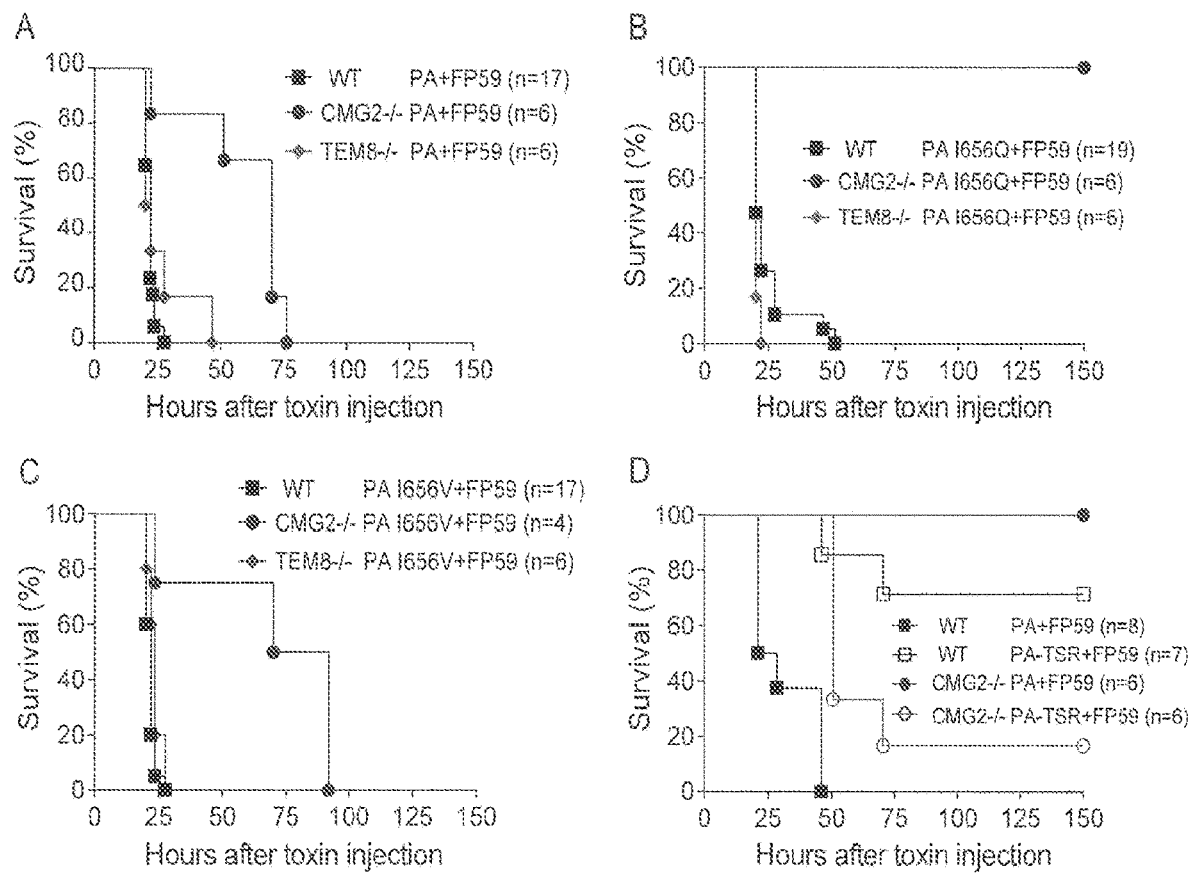

FIG. 17A is a graph showing the survival (percentage) of wild-type (WT) (squares), CMG2$^{-/-}$ (circles), and TEM8$^{-/-}$ (diamonds) mice at various time points (hours) following injection of native PA and FP59. Group sizes are indicated for each toxin.

FIG. 17B is a graph showing the survival (percentage) of WT (squares), CMG2$^{-/-}$ (circles), and TEM8$^{-/-}$ (diamonds) mice at various time points (hours) following injection of PA I656Q and FP59. Group sizes are indicated for each toxin.

FIG. 17C is a graph showing the survival (percentage) of WT (squares), CMG2$^{-/-}$ (circles), and TEM8$^{-/-}$ (diamonds) mice at various time points (hours) following injection of PA I656V and FP59. Group sizes are indicated for each toxin.

FIG. 17D is a graph showing the survival (percentage) of (i) WT (open squares) and CMG2$^{-/-}$ (open circles) mice at various time points (hours) following injection of the PA E654T/R659S/M662R protein (abbreviated PA TSR) and FP59 and (ii) WT (closed squares) and CMG2$^{-/-}$ (closed circles) mice at various time points (hours) after injection of native PA and FP59. Group sizes are indicated for each toxin.

Figure 18:
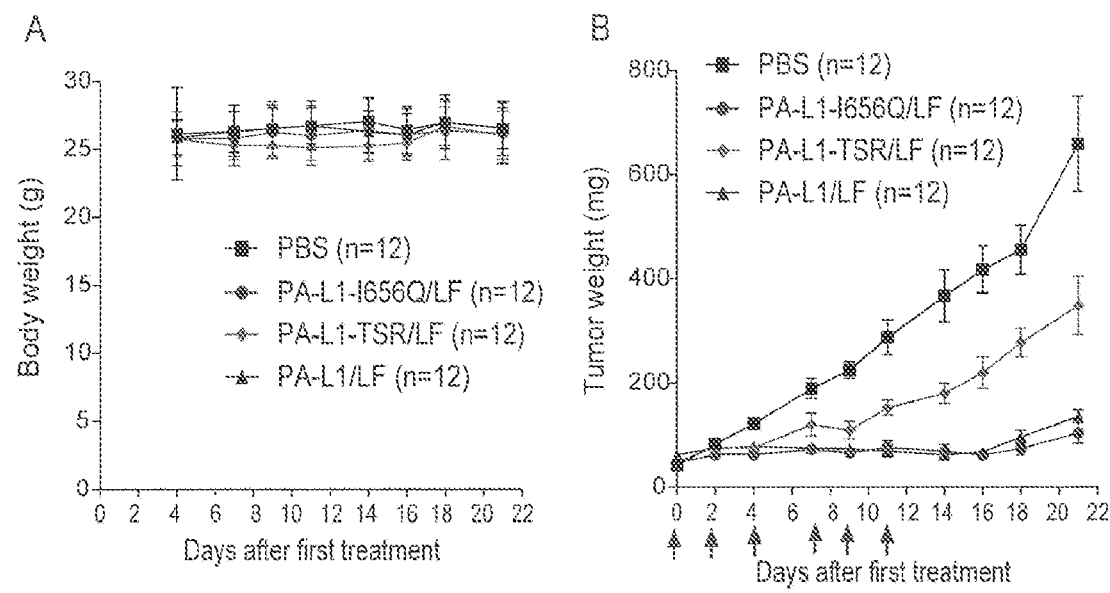

FIG. 18A is a graph showing the body weight (g) of mice bearing a HeLa xenograft which were injected intraperitoneally with PBS (■), 15 µg PA-L1+5 µg LF (▲), 15 µg PA-L1 I656Q+5 µg LF (•) or 30 µg PA-L1 TSR+10 µg LF (♦). Group sizes are indicated for each toxin.

FIG. 18B is a graph showing the weight (g) of intradermal tumor nodules (expressed as mean of tumor weight) in mice bearing a HeLa xenograft which were injected intraperitoneally with PBS (■), 15 µg PA-L1+5 µg LF (▲), 15 µg PA-L1 I656Q+5 µg LF (•) or 30 µg PA-L1 TSR+10 µg LF (♦). Group sizes are indicated for each toxin. Arrows indicate days on which toxin was injected. PBS vs. PA-L1/LF=P<0.01. PBS vs. PA-L1-I656Q/LF=P<0.01. PA-L1-TSR/LF vs. PA-L1/LF=P<0.01. PA-L1-TSR/LF vs PA-L1-I656Q/LF=P<0.01.

Figure 19:
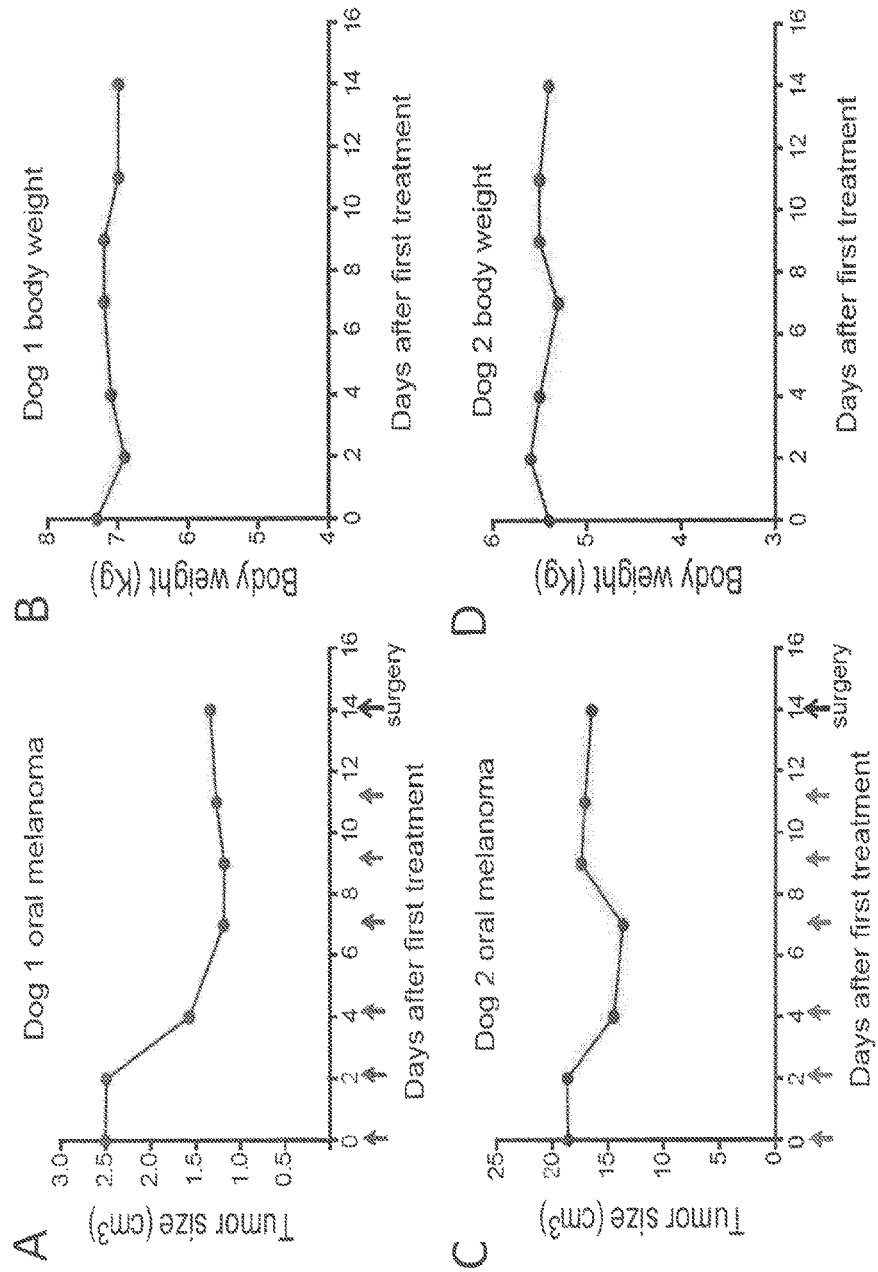

FIGS. 19A and 19C are graphs showing oral melanoma tumor size (cm$^3$) in Dog 1 (A) and Dog 2 (C) treated with 750 µg IC2-PA (PA-L1-I207R+PA-U2-R200A) plus 250 µg LF at various time points (days) after first treatment. The rightmost arrow indicates surgical removal of the tumor. The remainder of the arrows indicate the days on which the dogs were treated with IC2-PA plus LF.

FIGS. 19B and 19D are graphs showing the body weight (kg) of Dog 1 (B) and Dog 2 (D) at various time points after first treatment with IC2-PA plus LF.

DETAILED DESCRIPTION OF THE INVENTION

Anthrax toxin is a protein toxin produced by *Bacillus anthracis*. Anthrax toxin includes three components: the protective antigen (PrAg or PA), the lethal factor (LF), and the edema factor (EF). PA binds to a cell surface receptor for PA. The native, wild-type PA is cleaved after the sequence RKKR (SEQ ID NO: 4) by cell-surface furin or furin-like proteases into two fragments: PrAg63 and PrAg20. PrAg63 is a 63 kDa, C-terminal fragment which remains receptor-bound and forms a homo-oligomeric heptamer. PrAg20 is a 20 kDa, N-terminal fragment which is released into the cell medium. The PrAg63 homo-oligomeric heptamer forms the binding site for effector components LF and/or EF. Each LF/EF binding site is comprised of three subsites on two adjacent PA monomers. Upon the binding of LF and/or EF to PA, the resulting complex is internalized in a target cell where the LF and/or EF exert toxic effects.

The premature native, wild-type PA amino acid sequence is set forth in Genbank Accession No. NP_052806 (SEQ ID NO: 2). A coding sequence for the premature native, wild-type PA amino acid sequence is the nucleotide sequence of SEQ ID NO: 33. Another premature PA amino acid sequence is set forth in SEQ ID NO: 5. Premature PA contains an N-terminal signal peptide (SEQ ID NO: 3, which corresponds to amino acid residues 1-29 of SEQ ID NO: 2) which is removed in the mature form of PA. The mature, wild-type PA amino acid sequence (without the N-terminal signal peptide) is set forth in SEQ ID NO: 1.

Unless specified otherwise, amino acid residue position numbers of PA are defined herein by reference to the amino acid sequence of the mature, wild-type PA amino acid sequence of SEQ ID NO: 1. Thus, substitutions of PA are described herein by reference to the amino acid residue present at a particular position, followed by the amino acid with which that residue has been replaced in the particular substitution under discussion. In this regard, the positions of the amino acid sequence of a particular embodiment of a PA are referred to herein as the positions as defined by SEQ ID NO: 1. The actual positions of the amino acid sequence of a particular embodiment of a PA are defined relative to the corresponding positions of SEQ ID NO: 1 and may represent different residue position numbers than the residue position numbers of SEQ ID NO: 1. Thus, for example, substitutions refer to a replacement of an amino acid residue in the amino acid sequence of a particular embodiment of a PA corresponding to the indicated position of the 735-amino acid sequence of SEQ ID NO: 1 with the understanding that the actual positions in the respective amino acid sequences may be different. For example, when the positions are as defined by SEQ ID NO: 1, the term "R200" refers to the arginine normally present at position 200 of SEQ ID NO: 1, "R200A" indicates that the arginine normally present at position 200 of SEQ ID NO: 1 is replaced by an alanine, while "I207R" indicates that the isoleucine normally present at position 207 of SEQ ID NO: 1 has been replaced with an arginine. In the event of multiple substitutions at two or more positions, the two or more substitutions may be the same or different, i.e., each amino acid residue of the two or more amino acid residues being substituted can be substituted with the same or different amino acid residue unless explicitly indicated otherwise.

Variants of PA, and combinations thereof, may provide cancer-cell specific cytotoxicity. For example, the PA variant PA-U2-R200A is a urokinase plasminogen activator-activated PA variant with LF-binding subsite II residue R200 mutated to Ala, and the PA variant PA-L1-I210A is a matrix metalloproteinase-activated PA variant with LF-binding subsite III residue I210 mutated to Ala. PA-U2-R200A and PA-L1-I210A provide reduced cytotoxicity when used singly. However, when combined, PA-U2-R200A and PA-L1-I210A (collectively referred to as IC-PA) form LF-binding competent heterogeneous oligomers by intermolecular complementation, and achieve high specificity in tumor targeting. Nevertheless, IC-PA may provide undesirable non-specific toxicity to normal tissues.

It has been discovered that replacing the native amino acid residue at one or both of positions 207 and 210 of *Bacillus anthracis* PA with an amino acid residue other than alanine advantageously reduces non-specific toxicity to normal tissues and provides potent anti-tumor activity. Accordingly, an embodiment of the invention provides a *Bacillus anthracis* PA comprising a PA amino acid sequence, wherein one or both of amino acid residues I207 and I210, as defined by reference to SEQ ID NO: 1, are, independently, substituted, with the proviso that amino acid residue I207 is not substituted with alanine and amino acid residue I210 is not substituted with alanine.

In a preferred embodiment, the PA comprises a PA amino acid sequence, wherein amino acid residue I207, as defined by reference to SEQ ID NO: 1, is substituted, with the proviso that amino acid residue I207 is not substituted with alanine.

Amino acid residues I207 and I210 may be independently substituted with any amino acid residue other than alanine. Preferably, amino acid residue I210 is substituted with aspartic acid, glutamic acid, lysine, glutamine, arginine, or serine. Preferably, amino acid residue I207 is substituted with arginine, tryptophan, or tyrosine. In an especially preferred embodiment, amino acid residue I207 is substituted with arginine.

It has also been discovered that replacing the native amino acid residue at one or more of positions 656, 681, and 687 of *Bacillus anthracis* PA advantageously improves selectivity for CMG2 (which is expressed by tumor endothelial cells), reduces non-specific toxicity to normal tissues, and provides potent anti-tumor activity. Accordingly, an embodiment of the invention provides a *Bacillus anthracis* PA comprising a PA amino acid sequence, wherein one or more of amino acid residues I656, Y681, and L687, as defined by reference to SEQ ID NO: 1, are, independently, substituted.

Amino acid residues I656, Y681, and L687 may be independently substituted with any amino acid residue. Preferably, amino acid residue I656 is substituted with glutamine, valine, alanine, cysteine, or glutamic acid. Preferably, amino acid residue Y681 is substituted with alanine. Preferably, amino acid residue L687 is substituted with alanine.

It has also been discovered that replacing the native amino acid residue at one or more of positions 654, 659, and 662 of *Bacillus anthracis* PA advantageously improves selectivity for TEM8. Accordingly, an embodiment of the invention provides a *Bacillus anthracis* PA comprising a PA amino acid sequence, wherein one or more of amino acid residues E654, R659, and M662, as defined by reference to SEQ ID NO: 1, are, independently, substituted. A PA wherein one or more of amino acid residues E654, R659, and M662 is substituted may be useful as, for example, a research tool and/or may provide anti-tumor activity for tumors that have a high expression of TEM8.

Amino acid residues E654, R659, and M662 may be independently substituted with any amino acid residue. Preferably, amino acid residue E654 is substituted with threonine. Preferably, amino acid residue R659 is substituted with serine. Preferably, amino acid residue M662 is substituted with arginine.

The inventive PA may comprise any of the amino acid residue substitutions described herein in any combination.

Accordingly, an embodiment of the invention provides a *Bacillus anthracis* PA comprising a PA amino acid sequence, wherein one or more of amino acid residues I207, I210, E654, I656, R659, M662, Y681, and L687, as defined by reference to SEQ ID NO: 1, are, independently, substituted, with the proviso that amino acid residue I207 is not substituted with alanine and amino acid residue I210 is not substituted with alanine.

The terms "protective antigen," "PA," and "PrAg," as used herein, include PA that includes any one or more of the following modifications: (a) substitution of a native cell-recognition domain for a non-native cell-recognition domain; (b) substitution of a native proteolytic activation site for a non-native proteolytic activation site; (c) modification of a first PA to generate a first modified PA, whereby the first modified PA can pair only with a second PA; or (d) modification of the first PA and the second PA, whereby an effector component (e.g., LF and/or EF) can bind only at a site formed by the interaction of the first PA and the second PA.

For example, the PA may be modified by substitution of the native cell recognition domain for a non-native cell recognition domain as described in, e.g., U.S. Pat. No. 7,947,289, which is incorporated herein by reference. The non-native cell recognition domain recognizes and/or binds to a molecule on the surface of a target cell population (e.g., a cancer cell), thus specifically targeting the modified PA to the target cells. Substitution of a native cell recognition domain may comprise, e.g., substitution of the native cell recognition domain with a recognition domain for another cell surface molecule. The PA may be modified such that it no longer binds to the PA receptors, but binds to other cell surface molecules (e.g., receptors for cytokines). The PA may also be modified such that it binds to the PA receptor in addition to other cell surface molecules. Exemplary non-native cell recognition domains include, e.g., an antibody, a cytokine, or a cell surface receptor ligand. Suitable non-native cell recognition domains include, e.g., VEGF, C-CSF, GM-CSF, EPO, EGF, IL-1, IL-2, IL-4, IL-5, IL-6, interferon α, interferon γ, growth hormone, prolactin, thrombopoietin, and TGF-β. Exemplary antibodies may include, e.g., an antibody that specifically binds a protein that is overexpressed on cancer cells such as, for example, Her2/Neu, CD19, CD276, CD25, CD30, CA19-9, CA-125, VEGF receptors, C-CSF receptors, GM-CSF receptors, EPO receptors, EGF receptors, interleukin receptors (e.g., IL-1R, IL-2R, IL-4R, IL-5R, or IL-6R), interferon receptors (e.g., interferon α or interferon γ), growth hormone receptors, prolactin receptors, thrombopoietin receptors, and TGF-β receptors.

Alternatively or additionally, the PAs may be modified by substitution of the native proteolytic cleavage site(s) with nonnative proteolytic cleavage site(s) as described in, e.g., U.S. Pat. No. 7,947,289, which is incorporated herein by reference. Thus, the PA can be activated via cleavage by proteases present on the surface of specific target cell types (e.g., cancer cells). Examples of proteolytic cleavage sites that can be substituted for native cleavage sites on the PA include cleavage sites for any proteases known in the art including, e.g., metalloproteinase, a cysteine protease, an aspartic acid protease, a plasminogen activator, a kallikrein, a type 1 transmembrane serine protease, a type 2 transmembrane serine protease, or a GPI anchored serine protease. Proteases include, e.g., plasminogen activators (uPA and tPA), matrix metalloproteinases, (e.g., MMP-1; MMP-2; MMP-3; MMP-7; MMP-8; MMP-9; MMP-10; MMP-11; MMP-12; MMP-13; MMP-14; MMP-15; MMP-16; MMP-17; MMP-19; MMP-20; MMP-21; MMP-23A; MMP-23B; MMP-24; MMP-25; MMP-26; MMP-27; MMP-28; and MT2-MMP); metalloproteases (e.g., Meprin a; Meprin b; Decysin; ADAM1a; ADAM2; ADAM3B; ADAM4; ADAM4B; ADAM5; ADAM6; ADAM7; ADAM8; ADAM9; ADAM10; ADAM11; ADAM12; ADAM15; ADAM17; ADAM18; ADAM19; ADAM20; ADAM21; ADAM22; ADAM23; ADAM28; ADAM29; ADAM30; ADAM32; ADAM33; ADAMTS1; ADAMTS2; ADAMTS3; ADAMTS4; ADAMTS5/11; ADAMTS6; ADAMTS7; ADAMTS8; ADAMTS9; ADAMTS10; ADAMTS12; ADAMTS13; ADAMTS14; ADAMTS15; ADAMTS16; ADAMTS17; ADAMTS18; ADAMTS19; ADAMTS20); serine proteases (e.g., Kallikrein hK1; Kallikrein hK2; Kallikrein hK3/PSA; Kallikrein hK4; Kallikrein hK5; Kallikrein hK6; Kallikrein hK7; Kallikrein hK8; Kallikrein hK9; Kallikrein hK10; Kallikrein hK11; Kallikrein hK12; Kallikrein hK13; Kallikrein hK14; Kallikrein hK15; Thrombin; Coagulation factor VIIa; Coagulation factor IXa; Coagulation factor Xa; Coagulation factor XIa; Coagulation factor XIIa; Protein C; Protein Z; Mastin; Tryptase-α1; Tryptase-α2; Tryptase-β1; Tryptase-δ1; Tryptase-γ1; Marapsin; Marapsin-2; Testisin; Brain serine protease-2; Prostasin; Prostasin-like 1; Prostasin-like 2; Chymase; Cathepsin G; Neutrophil elastase; Azurocidin; Hepsin; HAT-related protease; HAT (Human Airway Trypsin-like Protease); Type I transmembrane serine proteases, type II transmembrane serine proteases, cysteine proteases, aspartic acid proteases, HAT-like 1; HAT-like 2; HAT-like 3; HAT-like 4; HAT-like 5; DESC1; Corin; Matriptase; Matriptase-2; Matriptase-3; TMPRSS3; TMPRSS4; Spinesin; Polyserase; MSPL; Neurotrypsin; Urokinase plasminogen activator; Tissue plasminogen activator; Plasminogen; Acrosin; Plasma-kallikrein-like 1; Plasma-kallikrein-like 2; Plasma-kallikrein-like 3; Plasma-kallikrein-like 4; and Seprase); and aspartic proteases (e.g., Cathepsin D; and Cathepsin E); Cysteine Proteases (e.g., Cathepsin B; Cathepsin C; Cathepsin F; Cathepsin H; Cathepsin K; Cathepsin L; Cathepsin L2; Cathepsin S; Cathepsin W; Cathepsin Z and Cathepsin J).

In a preferred embodiment, the PA is modified by substitution of the native proteolytic cleavage site(s) with an MMP cleavage site or a plasminogen activator cleavage site. Both MMP and plasminogen activator proteases are overproduced by tumor tissues and are implicated in cancer cell growth and metastasis (Dano et al., *APMIS*, 107: 120-127 (1999)). In an embodiment of the invention, the native furin cleavage site (e.g., SEQ ID NO: 4) of the PA is replaced with an MMP cleavage site or a plasminogen activator cleavage site. Examples of MMP cleavage sites that may be useful in the inventive PAs include GPLGMLSQ (SEQ ID NO: 6) and GPLGLWAQ (SEQ ID NO: 7). In this regard, the PA may comprise an MMP cleavage site. Examples of plasminogen activator cleavage sites that may be useful in the inventive PAs include PCPGRVVGG (SEQ ID NO: 8), PGSGRSA (SEQ ID NO: 9), PGSGKSA (SEQ ID NO: 10), PQRGRSA (SEQ ID NO: 11), PCPGRVVGG (SEQ ID NO: 12), GSGRSA (SEQ ID NO: 13), GSGKSA (SEQ ID NO: 14), QRGRSA (SEQ ID NO: 15). In this regard, the PA may comprise a plasminogen activator cleavage site.

Alternatively or additionally, the PA may be modified so that each individual PA molecule (PA monomer) can only form hetero-oligomers (i.e., each PA monomer can pair only with a PA monomer of a different type (i.e., having a different amino acid sequence)) as described in, e.g., U.S. Pat. No. 7,947,289, which is incorporated herein by reference. The modified PA monomers may comprise PA monomer binding sites which have been modified such that the PA monomer can bind only to a PA monomer of a different type. In some embodiments, the PA monomer binding sites have been modified such that the PA monomer can bind two PA monomers of two different types. For example, a PA monomer that forms a heptameric complex can be modified so that each PA monomer can bind only to two different, but complementary PA monomers, each of which has a modified PA monomer binding site. For example, one or more of the following amino acid substitutions may provide a PA monomer that can only form a hetero-oligomeric heptamer: aspartic acid at position 512 for alanine; aspartic acid at position 512 for lysine; lysine at position 199 for glutamic acid; arginine at position 468 for alanine, and arginine at position 470 for aspartic acid. For example, a modified PA monomer comprising an alanine at position 512 is unable to homo-oligomerize, but can form functional hetero-oligomers with a modified PA with a glutamic acid at position 199, an alanine at position 468, and an aspartic acid at position 470, as defined by reference to SEQ ID NO: 1.

Alternatively or additionally, the PA may be modified so that at least two PA monomers (each having a different amino acid sequence) are needed to bind an effector component (e.g., LF and/or EF) so that the effector component can be delivered to a target cell and exert a biological effect (e.g., target cell killing or inhibition of target cell proliferation) as described in, e.g., U.S. Pat. No. 7,947,289, which is incorporated herein by reference. The portion of a first PA monomer that binds to the effector component may be modified so that a second PA monomer of a different type (i.e., having a different amino acid sequence) is required to effectively bind the effector molecule.

For example, the native lethal factor (LF) binding site of the PA may be mutated so that at least two different PA monomer types are required to bind LF. In an embodiment of the invention, a substitution of the native amino acid residue at one or more of the following positions may provide a PA monomer that cannot homo-oligomerize to form a functional LF binding site: 178, 197, 200, 207, 210, and 214, as defined by reference to SEQ ID NO: 1. However, in one embodiment of the invention, the combination of (i) a PA monomer comprising a substitution of the native amino acid residue at position 200 and (ii) a PA monomer comprising a substitution of the amino acid residue at position 207 may form functional PA heptamers that bind LF. In another embodiment of the invention, the combination of (i) a PA monomer comprising a substitution of the native amino acid residue at position 200 and (ii) a PA monomer comprising a substitution of the amino acid residue at position 210 may form functional PA heptamers that bind LF. For example, one or more of the following substitutions may provide a PA monomer that cannot homo-oligomerize to form a functional LF binding site: arginine at position 178 for alanine; lysine at position 197 for alanine; arginine at position 200 for alanine; isoleucine at position 207 for arginine; isoleucine at position 210 for alanine; lysine at position 214 for alanine, as defined by reference to SEQ ID NO: 1. Modified PA monomers comprising alanine at position 200 (e.g., R200A), modified PA monomers comprising alanine at position 210 (e.g., I210A), modified PA monomers comprising arginine at position 210 (e.g., I207R), and modified PA monomers comprising alanine at position 214 (e.g., K214A) are unable to homo-oligomerize and form a functional PA heptamer that binds LF. However, the combination of any one or more of (i) a PA monomer having the substitution of R200A or R200C with (ii) any one or more of a PA monomer having the substitution of I207R, I207W, I210D, I210E, I210K, I210Q, I210R, or I210S may form functional PA heptamers that bind LF. For example, the combination of a PA monomer comprising R200A and a PA monomer comprising I207R may form functional PA heptamers that bind LF.

Accordingly, an embodiment of the invention also provides compositions comprising combinations of any of the PA monomers described herein which, when employed singly, are unable to homo-oligomerize and form a functional PA heptamer that binds LF, but when combined, may form functional PA heptamers that bind LF. Accordingly, an embodiment of the invention provides a composition comprising a first PA comprising a first PA amino acid sequence and a second PA comprising a second PA amino acid sequence. The first PA comprises a first PA amino acid sequence, wherein (i) one or both of amino acid residues I207 and I210, as defined by reference to SEQ ID NO: 1, are, independently, substituted, with the proviso that amino acid residue I207 is not substituted with alanine and amino acid residue I210 is not substituted with alanine; (ii) one or more of amino acid residues I207, I210, E654, I656, R659, M662, Y681, and L687, as defined by reference to SEQ ID NO: 1, are, independently, substituted, with the proviso that amino acid residue I207 is not substituted with alanine and amino acid residue I210 is not substituted with alanine; (iii) one or more of amino acid residues I656, Y681, and L687, as defined by reference to SEQ ID NO: 1, are, independently, substituted; or (iv) one or more of amino acid residues E654, R659, and M662, as defined by reference to SEQ ID NO: 1, are, independently, substituted. The second PA comprises a second PA amino acid sequence, wherein amino acid residue R200 of the second PA amino acid sequence, as defined by reference to SEQ ID NO: 1, is substituted. The second PA amino acid sequence is different from the first PA amino acid sequence.

Amino acid residue R200 of the second PA amino acid sequence may be substituted with any amino acid residue. In an embodiment of the invention, amino acid residue R200 of the second PA amino acid sequence is substituted with alanine, cysteine, aspartic acid, glutamic acid, glycine, isoleucine, methionine, proline, serine, valine, or tryptophan. In a preferred embodiment, amino acid residue R200 of the second PA amino acid sequence is substituted with alanine.

The first PA and the second PA may include any of the modifications described herein with respect to other aspects of the invention. In an embodiment of the invention, the second PA amino acid sequence is modified by substitution of the native proteolytic cleavage site(s) with any of the nonnative proteolytic cleavage site(s) described herein. In an embodiment of the invention, the first PA comprises an MMP cleavage site and the second PA comprises a plasminogen activator cleavage site. The plasminogen activator cleavage site may be selected from the group consisting of SEQ ID NOs: 8-15.

The inventive compositions may further comprise an effector component which binds to a heptamer formed by the modified PAs and exerts a biological effect (e.g., killing of a target cell or inhibition of target cell proliferation). Suitable effector components include, e.g., anthrax lethal factor, anthrax edema factor, truncated anthrax lethal factor (e.g., LFn or amino acids 1-254 of anthrax lethal factor), FP59 (LFn fused to the ADP-ribosylation domain of *Pseudomonas* exotoxin A as described in, e.g., Arora et al., *J. Biol. Chem.*, 268:3334-3341 (1993) and WO 01/21656), and cytolethal distending toxin subunit B (CdtB) conjugated or fused to *Bacillus anthracis* toxin LF as described in International Publication No. WO 2014/205187.

Toxin proteins such as, for example, the PAs described herein, may be highly immunogenic upon administration to a mammal. Such immunogenicity may reduce the amount of PA that can be given to a mammal which may, in turn, reduce the effectiveness of the PA for treating or preventing the disease, e.g., cancer. It has been discovered that the combination of pentostatin and cyclophosphamide advantageously reduces or prevents the induction of antibodies against the inventive PAs described herein. Accordingly, an embodiment of the invention provides any of the compositions described herein, wherein the composition further comprises an immunosuppressive agent. In an embodiment of the invention, the immunosuppressive agent is the combination of pentostatin and cyclophosphamide.

An embodiment of the invention provides a nucleic acid comprising a nucleotide sequence encoding any of the inventive PAs described herein. In an embodiment, the nucleic acid comprises a nucleotide sequence encoding a PA amino acid sequence including the I207R substitution, wherein the nucleotide sequence comprises SEQ ID NO: 29.

The term "nucleic acid," as used herein, includes "polynucleotide," "oligonucleotide," and "nucleic acid molecule," and generally means a polymer of DNA or RNA, which can be single-stranded or double-stranded, which can be synthesized or obtained (e.g., isolated, purified, or both isolated and purified) from natural sources, which can contain natural, non-natural or altered nucleotides, and which can contain a natural, non-natural, or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, substitutions, or combinations thereof. However, it may be suitable in some instances, as discussed herein, for the nucleic acid to comprise one or more insertions, deletions, inversions, substitutions, or combinations thereof.

Preferably, the nucleic acids of the invention are recombinant. As used herein, the term "recombinant" refers to (i) molecules that are constructed outside living cells by joining natural or synthetic nucleic acid segments, or (ii) molecules that result from the replication of those described in (i) above. For purposes herein, the replication can be in vitro replication or in vivo replication.

The nucleic acids can be constructed based on chemical synthesis, enzymatic ligation reactions, or combinations thereof using procedures known in the art. See, for example, Green and Sambrook, *Molecular Cloning: A Laboratory Manual*, Cold Spring Harbor Laboratory Press, 4th Ed. (2012). For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The invention also provides a nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches, from a random sequence that happened to have only a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt conditions, high temperature conditions, or combinations thereof, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive proteins or chimeric molecules. It is generally appreciated that conditions can be rendered more stringent by the addition of increasing amounts of formamide.

The invention also provides a nucleic acid comprising a nucleotide sequence that is about 70% or more, e.g., about 80% or more, about 90% or more, about 91% or more, about 92% or more, about 93% or more, about 94% or more, about 95% or more, about 96% or more, about 97% or more, about 98% or more, or about 99% or more identical to any of the nucleic acids described herein.

The nucleic acids of the invention can be incorporated into a recombinant expression vector. In this regard, the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, which can be synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages do not hinder the transcription or replication of the vector.

The recombinant expression vector of the invention can be any suitable recombinant expression vector, and can be used to transform or transfect any suitable host cell. Suitable vectors include those designed for propagation and expansion or for expression or for both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNMI149, also can be used. Examples of plant expression vectors include pBI01, pBI101.2, pBI101.3, pBI121 and pBIN19 (Clontech). Examples of animal expression vectors include pEUK-Cl, pMAM, and pMAMneo (Clontech). Preferably, the recombinant expression vector is a viral vector, e.g., a retroviral vector.

The recombinant expression vectors of the invention can be prepared using standard recombinant DNA techniques described in, for example, Green and Sambrook, supra. Constructs of expression vectors, which are circular or linear, can be prepared to contain a replication system functional in a prokaryotic or eukaryotic host cell. Replication systems can be derived, e.g., from ColE1, 2µ plasmid, λ, SV40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the inventive protein or chimeric molecule (including functional portions and functional variants), or to the nucleotide sequence which is complementary to or which hybridizes to the nucleotide sequence encoding the protein or chimeric molecule. The selection of promoters, e.g., strong, weak, inducible, tissue-specific, and developmental-specific, is within the ordinary skill of the artisan. Similarly, the combining of a nucleotide sequence with a promoter is also within the ordinary skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Another embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell, an adherent cell or a suspended cell, i.e., a cell that grows in suspension. For purposes of producing a recombinant inventive protein or chimeric molecule, the host cell is preferably a prokaryotic cell, e.g., an E. coli cell.

Also provided by the invention is a population of cells comprising at least one host cell described herein. The population of cells can be a heterogeneous population comprising the host cell comprising any of the recombinant expression vectors described, in addition to at least one other cell, e.g., a host cell which does not comprise any of the recombinant expression vectors. Alternatively, the population of cells can be a substantially homogeneous population, in which the population comprises mainly (e.g., consisting essentially of) host cells comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population of host cells comprising a recombinant expression vector as described herein.

The inventive proteins, chimeric molecules (including functional portions and functional variants), nucleic acids, recombinant expression vectors, host cells, and populations of cells can be isolated, purified, or both isolated or purified. The term "isolated" as used herein means having been removed from its natural environment. The term "purified" as used herein means having been increased in purity, wherein "purity" is a relative term, and not to be necessarily construed as absolute purity. For example, the purity can be about 50% or more, about 60% or more, about 70% or more, about 80% or more, about 90% or more, or about 100%. The purity preferably is about 90% or more (e.g., about 90% to about 95%) and more preferably about 98% or more (e.g., about 98% to about 99%).

The inventive PAs, nucleic acids, recombinant expression vectors, host cells, populations of cells, and compositions, all of which are collectively referred to as "inventive PA materials" hereinafter, can be formulated into a pharmaceutical composition. In this regard, the invention provides a pharmaceutical composition comprising any of the PAs, nucleic acids, recombinant expression vectors, host cells, populations of cells, or compositions described herein, and a pharmaceutically acceptable carrier.

Preferably, the carrier is a pharmaceutically acceptable carrier. With respect to pharmaceutical compositions, the carrier can be any of those conventionally used and is limited only by chemico-physical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular inventive PA material, as well as by the particular method used to administer the inventive PA material. Accordingly, there are a variety of suitable formulations of the pharmaceutical composition of the invention. The following formulations for parenteral (e.g., subcutaneous, intravenous, intraarterial, intramuscular, intradermal, interperitoneal, intratumoral, and intrathecal) and oral administration are exemplary and are in no way limiting. More than one route can be used to administer the inventive PA materials, and in certain instances, a particular route can provide a more immediate and more effective response than another route.

Formulations suitable for oral administration can include (a) liquid solutions, such as an effective amount of the inventive PA material dissolved in diluents, such as water or saline; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the inventive PA material in a flavor, usually sucrose and acacia or tragacanth, as well as pastilles comprising the inventive PA material in an inert base, such as gelatin and glycerin, or sucrose and acacia, emulsions, gels, and the like additionally containing such excipients as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inventive PA material can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1, 3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 2% by weight per volume of the inventive PA material in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described. The requirements for effective pharmaceutical carriers for parenteral compositions are well-known to those of ordinary skill in the art (see, e.g., Lloyd et al. (Eds.) Remington: The Science and Practice of Pharmacy, Pharmaceutical Press, $22^{ND}$ Ed. (2012)).

For purposes of the invention, the amount or dose of the inventive PA material administered should be sufficient to effect a desired response, e.g., a therapeutic or prophylactic response, in the mammal over a reasonable time frame. For example, the dose of the inventive PA material should be sufficient to inhibit growth of a target cell or treat or prevent cancer in a period of from about 2 hours or longer, e.g., 12 to 24 or more hours, from the time of administration. In certain embodiments, the time period could be even longer. The dose will be determined by the efficacy of the particular inventive PA material and the condition of the mammal (e.g., human), as well as the body weight of the mammal (e.g., human) to be treated.

Many assays for determining an administered dose are known in the art. An administered dose may be determined in vitro (e.g., cell cultures) or in vivo (e.g., animal studies). For example, an administered dose may be determined by determining the $IC_{50}$ (the dose that achieves a half-maximal inhibition of symptoms), $LD_{50}$ (the dose lethal to 50% of the population), the $ED_{50}$ (the dose therapeutically effective in 50% of the population), and the therapeutic index in cell culture, animal studies, or combinations thereof. The therapeutic index is the ratio of $LD_{50}$ to $ED_{50}$ (i.e., $LD_{50}/ED_{50}$).

The dose of the inventive PA material also may be determined by the existence, nature, and extent of any adverse side effects that might accompany the administration of a particular inventive PA material. Typically, the attending physician will decide the dosage of the inventive PA material with which to treat each individual patient, taking into consideration a variety of factors, such as age, body weight, general health, diet, sex, inventive PA material to be administered, route of administration, and the severity of the condition being treated. By way of example and not intending to limit the invention, the dose of the inventive PA material can be about 0.001 to about 1000 mg/kg body weight of the subject being treated/day, from about 0.01 to about 10 mg/kg body weight/day, about 0.01 mg to about 1 mg/kg body weight/day, from about 1 to about to about 1000 mg/kg body weight/day, from about 5 to about 500 mg/kg body weight/day, from about 10 to about 250 mg/kg body weight/day, about 25 to about 150 mg/kg body weight/day, about 10 mg/kg body weight/day, about 2 mg/kg body weight/day to about 5 mg/kg body weight/day, or about 4 mg/kg body weight/day.

The inventive PA materials may be assayed for cytotoxicity by assays known in the art. Examples of cytotoxicity assays include a MTT (3-(4,5-dimethyl-2-thiazolyl)-2,5-diphenyl-2H-tetrazolium bromide) assay, as described in Liu et al., $J. Biol. Chem.$, 278: 5227-5234 (2003).

It is contemplated that the inventive PA materials can be used in methods of treating or preventing a condition such as, for example, cancer. Without being bound to a particular theory or mechanism, it is believed that compositions comprising a combination of the first PA and the second PA as described herein form LF-binding competent heterogeneous oligomers by intermolecular complementation, and specifically kill cancer cells with no or minimal cross-reactivity with normal, non-cancerous cells. In this regard, the invention provides a method of treating or preventing cancer in a mammal, the method comprising administering to the mammal any of the inventive PA materials described herein in an amount effective to treat or prevent cancer in the mammal.

In an embodiment of the invention, the method further comprises administering to the mammal one or more of any of the effector components described herein. The first PA, the second PA, and the effector component may be administered simultaneously or in any suitable sequence. For example, the method may comprise administering the first PA prior to administering the second PA and administering the effector component after administering the second PA. Alternatively, the method may comprise administering the first PA and the second PA simultaneously and prior to administering the effector component. In a preferred embodiment, the method comprises administering the first PA, the second PA, and the effector component simultaneously.

In an embodiment, the method further comprises administering one or more immunosuppressive agents to the mammal in an amount effective to decrease the immune response to the inventive PA material. Administering one or more immunosuppressive agents to the mammal may, advantageously, eliminate or reduce an anti-PA material immune response including, for example, the production of anti-PA material antibodies and/or T-cells, that may otherwise undesirably neutralize the cytotoxic activity of the inventive PA material. In this regard, administering one or more immunosuppressive agents to the mammal may, advantageously, increase the amount of inventive PA material that can be given to the mammal which may, in turn, increase the effectiveness of the inventive PA material for treating or preventing a condition, such as, for example, cancer.

The method may comprise administering the inventive PA material and the one or more immunosuppressive agents simultaneously or sequentially to the mammal. While the method may comprise administering the one or more immunosuppressive agents to the mammal after administering the inventive PA material, preferably the method comprises administering the one or more immunosuppressive agents to the mammal prior to administering the inventive PA material or sequentially with the inventive PA material. Administering the one or more immunosuppressive agents to the mammal prior to administering the inventive PA material advantageously may eliminate or reduce an undesirable immune response to the inventive PA material before the immune system is exposed to the inventive PA material. For example, the method may comprise administering the one or more immunosuppressive agents to the mammal about one to about seven days prior to administering the inventive PA material to the mammal.

The one or more immunosuppressive agents may comprise any agent suitable for suppressing an immune response to the inventive PA material. In an embodiment, the one or more immunosuppressive agents are selected from the group consisting of pentostatin, cyclophosphamide, and tofacitinib (Hassan et al., *Sci. Transl. Med.,* 5(208):208ra147 (2013); Mossoba et al., *Clin. Cancer Res.,* 17: 3697-3705 (2011); and Onda et al., *J. Immunol.,* 193(1): 48-55 (2014). In an embodiment of the invention, the one or more immunosuppressive agents comprise a combination of pentostatin and cyclophosphamide. Pentostatin and cyclophosphamide may be administered simultaneously or in sequence. For example, pentostatin may be administered before administering cyclophosphamide. Alternatively, cyclophosphamide may be administered prior to administering pentostatin.

It has also been discovered that the combination of pentostatin and cyclophosphamide provides anti-solid tumor effects when used in the absence of any other pharmaceutically active agents. Accordingly, an embodiment of the invention provides a method of treating or preventing a solid tumor in a mammal, the method comprising administering to the mammal pentostatin and cyclophosphamide in an amount effective to treat or prevent the solid tumor in the mammal. In a preferred embodiment, the method comprises administering pentostatin and cyclophosphamide in the absence of any other pharmaceutically active agents (e.g., in the absence of any other anti-cancer agents). For example, the method comprises administering pentostatin and cyclophosphamide in the absence of any of the inventive PA materials described herein. In an especially preferred embodiment, the method comprises administering pentostatin and cyclophosphamide (and a pharmaceutically inactive carrier) alone. Pentostatin and cyclophosphamide may be administered simultaneously or in sequence as described herein with respect to other aspects of the invention.

The terms "treat" and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount or any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

With respect to the inventive methods, the cancer can be any cancer, including any of adrenal gland cancer, sarcomas (e.g., synovial sarcoma, osteogenic sarcoma, leiomyosarcoma uteri, angiosarcoma, fibrosarcoma, rhabdomyosarcoma, liposarcoma, myxoma, rhabdomyoma, fibroma, lipoma, and teratoma), lymphomas (e.g., small lymphocytic lymphoma, Hodgkin lymphoma, and non-Hodgkin lymphoma), hepatocellular carcinoma, glioma, head cancers (e.g., squamous cell carcinoma, e.g., oral squamous cell carcinoma), neck cancers (e.g., squamous cell carcinoma), acute lymphocytic cancer, leukemias (e.g., hairy cell leukemia, myeloid leukemia (acute and chronic), lymphatic leukemia (acute and chronic), prolymphocytic leukemia (PLL), myelomonocytic leukemia (acute and chronic), and lymphocytic leukemia (acute and chronic)), bone cancer (osteogenic sarcoma, fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochondroma (osteocartilaginous exostoses), benign chondroma, chondroblastoma, chondromyxoid fibroma, osteoid osteoma, and giant cell tumors), brain cancer (astrocytoma, medulloblastoma, glioma, ependymoma, germinoma (pinealoma), glioblastoma multiforme, oligodendroglioma, schwannoma, and retinoblastoma), fallopian tube cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva (e.g., squamous cell carcinoma, intraepithelial carcinoma, adenocarcinoma, and fibrosarcoma), myeloproliferative disorders (e.g., chronic myeloid cancer), colon cancers (e.g., colon carcinoma), esophageal cancer (e.g., squamous cell carcinoma, adenocarcinoma, leiomyosarcoma, and lymphoma), cervical cancer (cervical carcinoma and pre-invasive cervical dysplasia), gastric cancer, gastrointestinal carcinoid tumor, hypopharynx cancer, larynx cancer, liver cancers (e.g., hepatocellular carcinoma, cholangiocarcinoma, hepatoblastoma, angiosarcoma, hepatocellular adenoma, and hemangioma), lung cancers (e.g., bronchogenic carcinoma (squamous cell, undifferentiated small cell, undifferentiated large cell, and adenocarcinoma), alveolar (bronchiolar) carcinoma, bronchial adenoma, chondromatous hamartoma, small cell lung cancer, non-small cell lung cancer, and lung adenocarcinoma), malignant mesothelioma, skin cancer (e.g., melanoma, basal cell carcinoma, squamous cell carcinoma, Kaposi's sarcoma, nevi, dysplastic nevi, lipoma, angioma, dermatofibroma, and keloids), multiple myeloma, nasopharynx cancer, ovarian cancer (e.g., ovarian carcinoma (serous cystadenocarcinoma, mucinous cystadenocarcinoma, endometrioid carcinoma, and clear cell adenocarcinoma), granulosa-theca cell tumors, Sertoli-Leydig cell tumors, dysgerminoma, and malignant teratoma), pancreatic cancer (e.g., ductal adenocarcinoma, insulinoma, glucagonoma, gastrinoma, carcinoid tumors, and VIPoma), peritoneum, omentum, mesentery cancer, pharynx cancer, prostate cancer (e.g., adenocarcinoma and sarcoma), rectal cancer, kidney cancer (e.g., adenocarcinoma, Wilms tumor (nephroblastoma), and renal cell carcinoma), small intestine cancer (adenocarcinoma, lymphoma, carcinoid tumors, Kaposi's sarcoma, leiomyoma, hemangioma, lipoma, neurofibroma, and fibroma), soft tissue cancer, stomach cancer (e.g., carcinoma, lymphoma, and leiomyosarcoma), testicular cancer (e.g., seminoma, teratoma, embryonal carcinoma, teratocarcinoma, choriocarcinoma, sarcoma, Leydig cell tumor, fibroma, fibroadenoma, adenomatoid tumors, and lipoma), cancer of the uterus (e.g., endometrial carcinoma), thyroid cancer, and urothelial cancers (e.g., squamous cell carcinoma, transitional cell carcinoma, adenocarcinoma, ureter cancer, and urinary bladder cancer). In an embodiment, the cancer is a solid tumor. In a preferred embodiment, the solid tumor is an oral squamous carcinoma tumor, a melanoma tumor, a lung tumor, or an ovarian tumor. Without being bound to a particular theory or mechanism, it is believed that the inventive PA materials, wherein one or more of amino acid residues I207, I210, I656, Y681, and L687 are substituted as described herein, are toxic to tumor endothelial cells that express CMG2. Accordingly, in an embodiment of the invention, the endothelial cells of the solid tumor express CMG2. Without being bound to a particular theory or mechanism, it is believed that the inventive PA materials, wherein one or more of amino acid residues E654, R659, and M662 are substituted as described herein, are toxic to cells that express TEM8. Accordingly, in an embodiment of the invention, the cells of the tumor express TEM8.

As used herein, the term "mammal" refers to any mammal, including, but not limited to, mammals of the orders Rodentia, such as mice and hamsters; Logomorpha, such as rabbits; Carnivora, including Felines (cats) and Canines (dogs); Artiodactyla, including Bovines (cows) and Swines (pigs); Perssodactyla, including Equines (horses); Primates, Ceboids, or Simoids (monkeys) or Anthropoids (humans and apes). In a preferred embodiment, the mammal is a human, mouse, cat or dog.

Also provided is a method of inhibiting the growth of a target cell comprising contacting the cell with any of the inventive PA materials described herein, in an amount effective to inhibit growth of the target cell. The growth of the target cell may be inhibited by any amount, e.g., by about 10% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, or about 100%. The target cell may be provided in a biological sample. A biological sample may be obtained from a mammal in any suitable manner and from any suitable source. The biological sample may, for example, be obtained by a blood draw, leukapheresis, tumor biopsy necropsy, or combinations thereof. The contacting step can take place in vitro or in vivo with respect to the mammal. Preferably, the contacting is in vitro.

In an embodiment of the invention, the target cell is a cancer cell. Preferably, the target cell is a cancer cell. The target cell may be a cancer cell of any of the cancers described herein. In an embodiment of the invention, the target may express a cell surface molecule. The cell surface marker may be any cell surface molecule described herein with respect to other aspects of the invention.

The method may comprise contacting the cell with the inventive PA material and the effector component simultaneously or sequentially. In an embodiment of the invention, the method comprises contacting the cell with the inventive PA material prior to contacting the cell with the effector component. In another embodiment, the method comprises contacting the cell with the effector component prior to administering the inventive PA material. Preferably, the method comprises contacting the cell with the effector component and the inventive PA simultaneously.

The following examples further illustrate the invention but, of course, should not be construed as in any way limiting its scope.

Examples 1-3

The following materials and methods were employed in the experiments described in Examples 1-3.

Mutagenic PCR

Mutations were introduced by overlap polymerase chain reaction (PCR) with NNS codons into the plasmid pYS52 (a derivative of *B. anthracis* expression vector pYS5 (Singh et al., *J. Biol. Chem.*, 264: 19103-19107 (1989)), which contains a synthetic DNA sequence coding for domain II of PA with additional unique restriction sites. PHUSION High-Fidelity DNA polymerase (New England Biologicals, Ipswich, Mass.) was used for mutagenic PCR reactions. Flanking primers used for all reactions were SEQ ID NO: 16 (PA-250) and SEQ ID NO: 17 (Pa-SwaI-Rev). Specific primers were SEQ ID NO: 18 (R178X mut), SEQ ID NO: 19 (R178X rev), SEQ ID NO: 20 (R200X mut), SEQ ID NO: 21 (R200X rev), SEQ ID NO: 22 (I207X mut), SEQ ID NO: 23 (I207/210X rev), SEQ ID NO: 24 (I210X mut), SEQ ID NO: 25 (K214X mut), and SEQ ID NO: 26 (K214X rev). Mutagenic primers were combined with PA-SwaI-Rev and reverse primers with PA-250 for the first round of PCR. The products were gel-purified and the complementary PCR fragments were extended to full length by 10 cycles of PCR before addition of PA-250 and PA-SwaI-rev and an additional 35 cycles. These mutagenic inserts were gel-purified and the inserts, along with pYS52, were digested with PstI and HindIII. The digestion products were ligated overnight and transformed into chemically competent *E. coli* MC1061, which were plated on lysogeny broth (LB)-agar plates containing 100 µg/mL ampicillin. Colony PCR using PA-250 and PA-SwaI-Rev primers was performed to identify positive clones. Colonies were screened using primer PA-250 to sequence the plasmid and identify clones having all possible substitutions. Selected clones were then grown overnight in LB containing 100 µg/mL ampicillin and the plasmids were extracted by mini-scale preparation.

Expression of Protein Library

Mini-prepared plasmids from *E. coli* MC1061 were transformed into chemically competent *E. coli* SCSI 10, which is dam⁻ and dcm⁻. The purified, non-methylated plasmids from SCSI 10 were then transformed into an electrocompetent *B. anthracis* BH480 strain, which was plated on LB-agar containing 20 g/mL kanamycin. BH480 is an avirulent large plasmids-cured, sporulation-defective *B. anthracis* strain with eight proteases deleted, serving as an efficient host for recombinant protein expression (Pomerantsev et al., *Protein Expr. Purif.*, 80: 80-90 (2011)). Single colonies were grown overnight in 5 mL FA medium containing 20 µg/mL kanamycin (Pomerantsev et al., supra). The supernatants containing the mutant PA proteins were sterilized by centrifugation and concentrated ~10 fold using AMICON ULTRA-4 (30K) Centrifugal Filter Devices (Millipore Corp., Billerica, Mass.). The supernatants were analyzed by native gel electrophoresis, strained with coommasie blue dye, and the protein concentrations were estimated by densitometry to compare the supernatant bands to a sample of purified PA. This was performed twice on each protein.

PA Variant Screen

RAW264.7 macrophages and murine melanoma B16-BL6 cells were grown in Dulbecco's Modified Eagle Medium (Life Technologies, Grand Island, N.Y.) supplemented with fetal bovine serum to 10% (Invitrogen) and gentamycin at 50 µg/mL (Invitrogen) at 37° C. in a tissue culture incubator with 5% $CO_2$.

To test the PA variants for a loss of function, RAW 264.7 macrophages were plated in a 96-well plate at $10^5$ cells/well and grown overnight. The next day, the PA variants were added at a concentration of 500 ng/mL and LF at a concentration of 100 ng/mL. The cells were incubated for 20 hours (h) and MTT (3-(4,5-dimethyl-2-thiazolyl)-2,5-diphenyl-2H-tetrazolium bromide, Sigma, St. Louis, Mo.) was added at 500 µg/mL for the final hour. The medium was aspirated and the oxidized MTT was solubilized in 91% isopropanol containing 0.5% SDS and 0.038 M hydrochloric acid, then read at 570 nm using a SPECTRAMAX 190 plate reader (Molecular Devices, Sunnyvale, Calif.). The absorbance was used to determine percent survival compared to an untreated control. PA variants that showed less toxicity than the original constructs PA-R200A and PA-I210A were subjected to a double-agent gain-of-function test. RAW 264.7 macrophages were seeded as above and respective PA variants (250 ng/mL) combined with PA-R200A or PA-I210A (250 ng/mL) and 100 ng/mL LF were added. The cells were incubated for 6 h and viability was measured as above.

Creation and Cytotoxicity of PA-L1-I207R

Site-directed mutagenesis was used to introduce mutation I207R into pYS5-L1 if, an overexpression plasmid for PA-L1, in which the furin cleavage sequence RKKR (SEQ ID NO: 4) (residues 164-167) was replaced with a MMP substrate sequence GPLGMLSQ (SEQ ID NO: 6) (Liu et al., *Cancer Res.*, 60: 6061-6067 (2000)). Primers used were SEQ ID NO: 27 (I207R sense), SEQ ID NO: 28 (I207R antisense). Sense and anti-sense primers were used with the QUIKCHANGE LIGHTNING Kit (Agilent, Santa Clara, Calif.) according to manufacturer's recommendations and transformed into chemically competent *E. coli* XL-10 GOLD cells. The plasmids were mini-prepared, sequenced, and transformed into *E. coli* SCS110 before transformation into BH480 for expression and purification. The coding sequence for PA-L1-I207R was the nucleotide sequence of SEQ ID NO: 29. Cytotoxicities of PA-L1-I207R and PA-L1-I210A were tested singly and in combination with PA-U2-R200A (with the furin cleavage sequence replaced with an uPA substrate sequence PGSGRSA (SEQ ID NO: 9) (Liu et al., *J. Biol. Chem.*, 276, 17976-17984 (2001)) in the presence of 30 ng/mL FP59. B16-BL6 cells were incubated with the indicated toxins in 96-well plates for 48 h, and cell viabilities were determined by MTT assay as described above.

Protein Purification

PA-L1-I210A, PA-L1-I207R, PA-U2-R200A, LF and FP59 were expressed using pYS5-based expression plasmids from *B. anthracis* BH480 strain. The recombinant proteins secreted into culture supernatants were purified as described previously (Pomerantsev et al., supra; Liu et al., *Cell. Microbiol.*, 9: 977-987 (2007)). In brief, the expression plasmid transformed BH480 strains were grown in FA medium with 10 µg/ml kanamycin for 12 h at 37° C. The proteins secreted into the culture supernatants were precipitated on PHENYL-SEPHAROSE 6 FAST FLOW resin (low substitution, GE Healthcare Life Sciences, Pittsburgh, Pa.) (30 ml per liter supernatant) in the presence of 2 M ammonium sulfate in rotating bottles. The resin was collected on a porous plastic funnel and washed with wash buffer (1.5 M ammonium sulfate, 10 mM Tris-HCl (pH 8.0), 1 mM EDTA) and the proteins were eluted using elution buffer (0.3 M ammonium sulfate, 10 mM Tris-HCl (pH 8.0), 1 mM EDTA). The eluted proteins were precipitated by adding 2 M ammonium sulfate. The precipitate was collected by centrifugation, resuspended and dialyzed in 10 mM Tris-HCl (pH 8.0), 1 mM EDTA. The toxin proteins were further purified by chromatography on Q-SEPHAROSE FAST FLOW column (GE Healthcare Life Sciences) and eluted with a 0-0.5 M NaCl gradient in 20 mM Tris-HCl, 0.5 mM EDTA (pH 8.0). The toxin proteins were further purified by SEPHACRYL S-200 high resolution gel filtration (GE Healthcare Life Sciences) using 10 mM Tris-HCl (pH 8.0), 100 mM NaCl, and 0.5 mM ethylenediaminetetraacetic acid (EDTA) to one prominent band at the expected molecular mass.

In Vivo Toxicity of PA Mutants

C57BL/6J male and female mice (10 to 12-week-old) were injected intraperitoneally with 20 μg PA-L1-I207R or PA-L1-I210A along with 10 μg FP59 at 0, 24, and 48 hours and checked twice daily for signs of malaise and mortality for two weeks following the first injection. Mice were euthanized at the end of experiment. All animal studies were carried out in accordance with protocols approved by the National Institute of Allergy and Infectious Diseases Animal Care and Use Committee.

In Vivo Anti-Tumor Study

Twelve-week-old female C57BL/6J mice (Jackson Laboratory, Bar Harbor, Me.) were injected with $5\times10^5$ B16-BL6 cells in the mid-scapular subcutis. B16-BL6 melanoma cells were authenticated by continual assessment of cellular morphology at both low and high magnifications. Eight days after injection, established tumors were measured with digital calipers (FV Fowler Company, Inc., Newton, Mass.). Tumor weights were estimated with the longest and shortest tumor dimensions in the formula: tumor weight (mg)= (length in mm×width in mm$^2$)×0.5 (Geran et al., *Cancer Chemother. Rep.*, 3: 1-103 (1972)). Tumor-bearing mice were randomized into groups and injected intraperitoneally on study days 0 (eight days after tumor cell injection), 2, 4, 7, and 9 with a 200 μL PBS solution containing the PA variant proteins and LF, at doses shown in FIG. 5. Mice were weighed and the tumors were measured before each injection. The study was ended on day 10 when tumors in the PBS alone control group reached 10% of the body weights, a condition requiring euthanasia according to the animal study protocol.

Statistical Analysis

Statistical analysis was done with unpaired student's t test using EXCEL software. Survival curves were analyzed using log-rank test (Mantel-Cox) using GRAPHPAD PRISM software.

Example 1

This example demonstrates the mutagenesis and expression of PA mutants.

Figure 1:
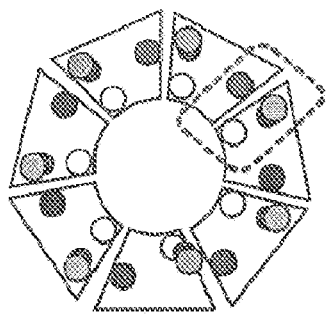
FIG. 1 is a schematic representation of PA oligomers, with each LF-binding site including three subsites (circles) located on adjacent PA monomers. While a heptamer is shown, the same interactions occur within octamers.

To select PA variants with activity strictly dependent on intermolecular complementation for LF-binding, a PA variant library with NNS (N=any nucleotide, S=C or G) codons at LF-binding subsite residue R200 on the counterclockwise-side monomer was constructed, and the residues R178, I207, I210, and K214 on the clockwise-side monomer (FIG. 1). While DNA coding sequences for all of the possible PA variants were isolated, some proteins were not expressed, or were expressed only at very low levels, from the corresponding transformed avirulent *B. anthracis* BH480 strains. Out of a theoretical library of 95 mutants, 79 were successfully expressed and supernatants containing the secreted PA variants were prepared for initial testing. PA proteins were usually expressed at high levels by the correspondingly transformed BH480 strains, often reaching levels above 50% of the total protein in the culture supernatant. Of the sixteen proteins that were not expressed, nine were mutants of K214 (C, D, E, F, G, P, S, W, Y), four were mutants at I207 (D, K, P, S), two were mutants of I210 (G, N), and one was an R178 mutant (P). K214 lies at the end of an α-helix and the side chain makes no close contact with any other residues on PA. It is not clear why so many mutants at this position could not be expressed.

Example 2

This example demonstrates that PA-I207R is an improved clockwise-side monomer variant.

The sterilized supernatants containing PA proteins were screened for activity relative to the original versions of the intermolecular complementing, PA-R200A or PA-I210A, as appropriate using cytotoxicity assays. In the screen of counterclockwise-side monomer mutants, ten mutant PA-R200X proteins (C, D, E, G, 1, M, P, S, V, and W) were initially identified as being less intrinsically toxic than PA-R200A. However, later detailed characterization found that these PA variants also showed reduced intermolecular complementation with PA-I210, resulting in less LF-induced cytotoxicity. As an example, although PA-R200C was slightly less toxic than PA-R200A, it was also slightly less effective in complementing with PA-I210A to promote killing of RAW264.7 cells. Therefore, none of the counterclockwise-side monomer PA variants were found to be significantly superior to the original PA-R200A.

Figure 2:
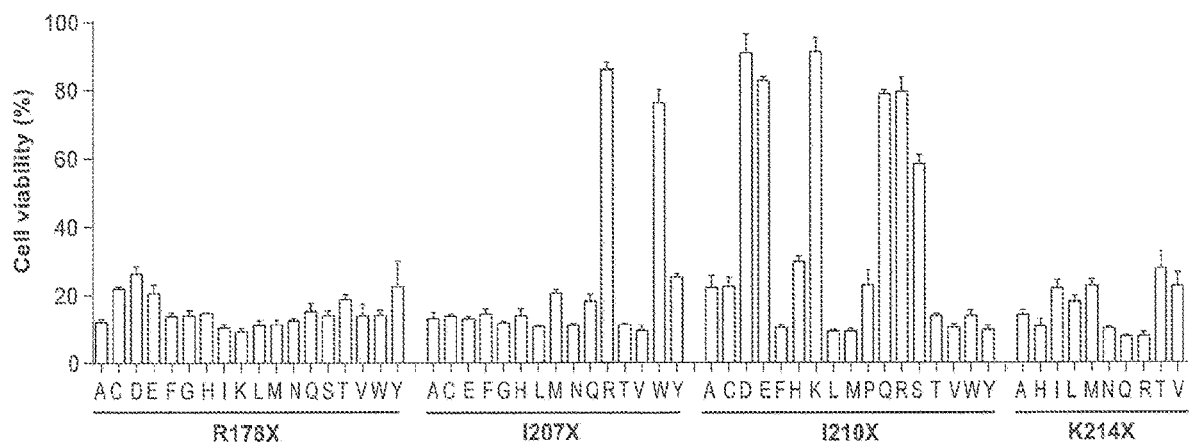
FIG. 2 is a graph showing the cell viability (%) of RAW264.7 macrophage cells treated with the indicated PA variants at about 500 ng/mL in the presence of 100 ng/mL LF for 20 h.
Figure 3:
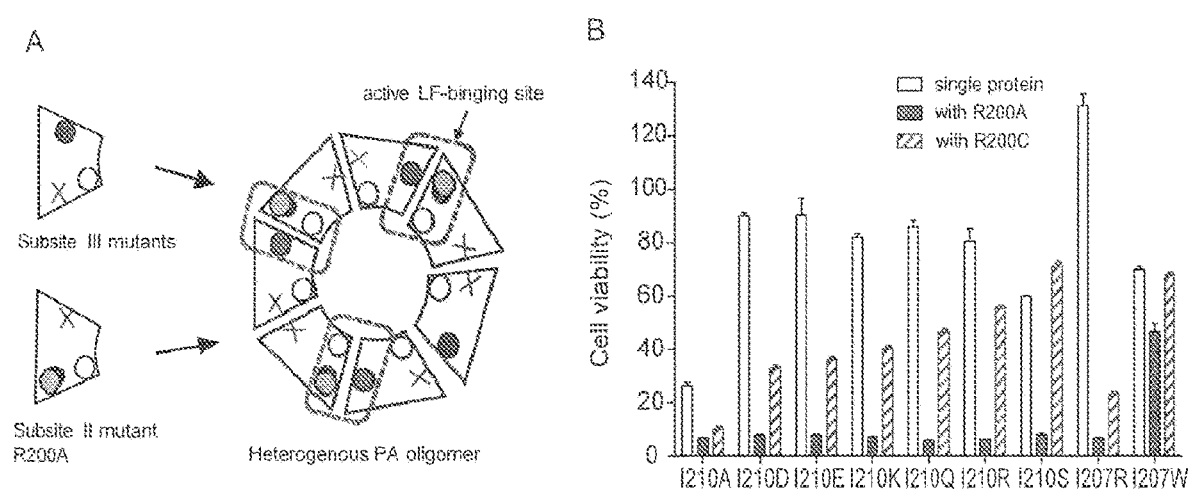

In screens for the clockwise-side monomer variants PA-R178X, PA-I207X, PA-I210X, and PA-K214X, eight proteins with greatly reduced inherent cytotoxicity to RAW264.7 macrophages were identified: I207R, I207W, I210D, I210E, I210K, I210Q, I210R, and I210S (FIG. 2). These were tested in combination with R200A and R200C for their ability in intermolecular complementation (FIG. 3B). All of these clockwise-side mutants could be complemented by PA-R200A and to a lesser extent by PA-R200C. Among these PA variants, PA-I207R behaved the best in complementing with both PA-R200A and PA-R200C to achieve killing of RAW264.7 cells. Therefore, PA-I207R was identified as an improved clockwise-side monomer variant for the intermolecular complementation PA system, displaying very low cytotoxicity when used singly.

To further characterize PA-I207R, the MMP-activated variant, i.e., PA-L1-I207R (SEQ ID NO: 30) was generated and the protein purified. The new combination of PA-L1-I207R and PA-U2-R200A was compared with the original combination of PA-L1-I210A and PA-U2-R200A for cytotoxicity towards mouse melanoma B16-BL6 cells, which express high levels of both MMPs and uPA. PA-L1-I207R showed similar activity as PA-L1-I207A in complementing with PA-U2-R200A to kill B16-BL6 cells in the presence of FP59, a LF fusion effector protein that kills cells in a PA-dependent manner (Arora et al., *Infect. Immun.*, 62: 4955-4961 (1994)) (FIG. 4A). Remarkably, the single component PA-L1-I207R showed no cytotoxicity, whereas the original counterpart PA-L1-I210A displayed moderate cytotoxicity to B16-BL6 cells when used singly ($IC_{50}$=200 ng/mL) in these assays (FIG. 4A). PA-U2-R200A also showed no cytotoxicity when used singly in these settings (FIG. 4A).

The toxicity of PA-L1-I207R and PA-L1-I210A was further compared when administered with FP59 to C57BL/6J mice. It was found that PA-L1-I207R was much less toxic than PA-L1-I210A in that all of the mice challenged with 3 doses of 20 μg PA-L1-I207R and 10 μg FP59 survived whereas all of the mice challenged with three doses of 20 μg PA-L1-I210A and 10 μg FP59 succumbed to the challenges within a week (P=0.0007, log-rank test (Mantel-Cox)) (FIG. 4B).

Example 3

This example demonstrates that the combination of PA-L1-I207R and PA-U2-R200A provides high efficacy in antitumor activity.

To further evaluate the anti-tumor activity of the new PA variant, a side-by-side comparison of the new combination, i.e., PA-L1-I207R (SEQ ID NO: 30) plus PA-U2-R200A (SEQ ID NO: 32), and the original combination of PA-L1-I210A and PA-U2-R200A in the treatment of B16-BL6 syngeneic tumors in C57BL/6J mice was performed. PA-U2-R200A was encoded by the nucleotide sequence of SEQ ID NO: 31. The tumor-bearing mice were treated with either PBS, low doses of the new combination or the original combination of the PA variants plus LF (7.5 μg/7.5 μg/5 μg), or high doses of each combination plus LF (22.5 μg/22.5 μg/15 μg). All of the toxin-treated groups showed significant anti-tumor activities compared to the PBS control group (FIG. 5) (P<0.0001 for all toxin-treated groups, Student's t test). The new combination of PA-L1-I207R and PA-U2-R200A showed significantly higher anti-tumor activity than the original combination of PA-L1-I210A and PA-U2-R200A (FIG. 5) (P=0.0326 for the two high dose groups at day 10, Student's t test). A mortality of 20% was observed in the PBS group before termination of the experiment at day 10, with deaths apparently due to the high tumor burden. The groups receiving the low doses of both combinations had 10% mortality, whereas in the high dose groups the new combination appeared to be safer, with a 10% mortality versus 30% mortality in the original combination group (although this difference was not statistically significant).

Examples 4-10

The following materials and methods were employed in the experiments described in Examples 4-10.

Proteins and Reagents

Recombinant PA variants and LF proteins were purified from supernatants of BH480, an avirulent, sporulation-defective, protease-deficient *B. anthracis* strain, as described previously (Gupta et al., *PLoS ONE,* 3: e3130 (2008); Pomerantsev et al., supra). FP59 is a fusion protein of LF amino acids 1-254 and the catalytic domain of *Pseudomonas aeruginosa* exotoxin A that kills cells by ADP-ribosylation of eukaryotic elongation factor-2 after delivery to cytosol by PA. The LF and FP59 used here contain the native amino-terminal sequence AGG (Gupta et al., supra). MTT (3-[4, 5-dimethylthiazol-2-yl]-2,5-diphenyltetrazolium bromide) and pentostatin (SML0508-25 mg) were from Sigma (Atlanta, Ga.). Cyclophosphamide (NDC10019-957-01) was from Baxter Healthcare (Deerfield, Ill.).

Cells and Cytotoxicity Assay

All cultured cells were grown at 37° C. in a 5% $CO_2$ atmosphere. Murine B16-BL6 melanoma cells, LL3 Lewis lung carcinoma cells, human lung carcinoma A549 cells, and colorectal carcinoma Colo205 cells were cultured in DMEM (Dulbecco's Modified Eagle Medium) supplemented with 10% fetal bovine serum. Mouse lung endothelial cells and tumor endothelial cells from B16-BL6 melanomas were isolated following the protocol for lung endothelial cell isolation (Reynolds et al., *Methods Mol. Med.,* 120:503-509 (2006)). Briefly, mouse lungs and B16-BL6 tumors were digested with type I collagenase and plated on gelatin and collagen-coated flasks. The cells were then subjected to sequential negative sorting by magnetic beads coated with a sheep anti-rat antibody using a Fc Blocker (rat anti-mouse CD16/CD32, Cat. 553142, BD Pharmingen, San Diego, Calif.) to remove macrophages and positive sorting by magnetic beads using an anti-intermolecular adhesion molecule 2 (ICAM2 or CD102) antibody (Cat. 553326, rat anti-mouse CD102, BD Pharmingen) to isolate endothelial cells. Endothelial cells were cultured in DMEM supplemented with 20% fetal bovine serum, endothelial cell growth supplement (30 mg in 500 mL DMEM) (E2759-15 mg, Sigma), heparin (50 mg in 500 mL DMEM) (H3149-100 KU, Sigma).

For cytotoxicity assays, cells grown in 96-well plates (50% confluence) were incubated with various concentrations of PA or PA variant proteins combined with 500 ng/mL LF for 72 h. In some experiments, cells were incubated with various concentrations of pentostatin or cyclophosphamide or their combination for 72 h. Cell viabilities were then assayed by MTT as described previously (Liu et al., *J. Biol. Chem.,* 278: 5227-5234 (2003)), expressed as % of MTT signals of untreated cells.

MEK Cleavage Assay

Tumor endothelial cells grown in 12-well plate were incubated with indicated concentrations of PA-L1 plus LF for 3 h at 37° C., then washed three times with Hank's Balanced Salt Solution (Biofluids, Rockville, Md.) to remove unbound toxins. Cells were then lysed in modified radioimmunoprecipitation assay (RIPA) lysis buffer containing protease inhibitors (Liu et al., *J. Biol. Chem.,* 278: 5227-5234 (2003)) and lysates were subjected to sodium dodecyl sulfate polyacrylamide gel electrophoresis (SDS-PAGE) and Western blotting to detect MEK2 cleavage using anti-MEK2 (N-terminus) antibody (sc-524, Santa Cruz Biotechnology, Santa Cruz, Calif.).

Gene Expression

Endothelial cells cultured in 12-well plates were treated with or without PA-L1/LF for 24 h, total RNA was then prepared using TRIZOL reagent (Invitrogen, Carlsbad, Calif.). Single-strand cDNA was synthesized using reverse transcriptase reaction kit following the manufacturer's manual (Invitrogen). Expression changes of the selected key genes involved in glucose uptake, glycolysis, tricarboxylic acid cycle, glutaminolysis, and lipid synthesis were analyzed by real-time quantitative PCR using a SYBR Green PCR Mastermix kit.

Oxygen Consumption Rates and Extracellular Acidification Rates

Metabolic activities of tumor endothelial cells were assessed in an XF24 Extracellular Flux analyzer (Seahorse Bioscience, North Billerica, Mass.). Tumor cells and tumor endothelial cells grown to confluence in 24-well XF24 tissue culture plates were incubated with or without PA-L1/LF (1 g/mL, each) in pentaplicates for 24 h. Cells were changed into fresh unbuffered serum-free DMEM with 200 mM GLUTAMAX-1 medium, 25 mM D-glucose, pH 7.4, and equilibrated in the medium for 1 h. Real-time extracellular acidification rates (ECARs) and oxygen consumption rates (OCRs) were then measured at 37° C. under basal conditions and conditions following sequential additions of oligomycin (0.5 μM), FCCP (carbonyl cyanide p-trifluoromethoxyphenylhydrazone) (0.5 μM), and antimycin A (1 μM). ECARs and OCRs were normalized to 50 mg total protein in cell lysates. Adenosine triphosphate (ATP) production-coupled OCR is calculated as the difference between basal OCR and OCR after addition of oligomycin. Spare respiratory capacity (SRC) is defined as the difference between the OCR following FCCP addition and the OCR under basal condition. Maximal respiration (MR) is defined as the difference between the OCR following FCCP addition and the OCR following oligomycin addition. Cellular ATP levels were measure using ATPLITE 1STEP kit (PerkinElmer, Boston, Mass.).

Mice and Tumor Studies

TEM8- and CMG2-null mice were generated previously (Liu et al., *Proc. Natl. Acad. Sci. USA,* 106: 12424-12429 (2009)). TEM8- and CMG2-null mice were also crossed with athymic nude (Foxn1$^{nu/nu}$) mice (Jackson Laboratory, Bar Harbor, Me.) to generate athymic nude TEM8- and CMG2-null mice, which were used to establish human tumor xenografts. Various tissue-specific CMG2-null mice, including Cmg2(EC)$^{-/-}$, Cmg2(SM)$^{-/-}$, Cmg2(Mye)$^{-/-}$ mice, and the tissue-specific CMG2-expressing mice, including Cmg2$^{EC}$ and Cmg2$^{SM}$ mice were generated as described previously (Liu et al., *Proc. Natl. Acad. Sci. USA,* 106: 12424-12429 (2009); Liu et al., *Cell Host Microbe,* 8: 455-462 (2010); Liu et al., *Nature,* 501: 63-68 (2013)). (Full descriptions of the genotypes are provided in the legends of FIGS. 8A-8E. For tumor studies, 10-14-week-old male and female mice were used. To grow syngeneic tumors, 5×10$^5$ cells/mouse B16-BL6 melanoma cells or LL3 lung carcinoma cells were injected in the mid-scapular subcutis of the pre-shaved mice with indicated genotypes. For human tumor xenografts, 1×10$^7$ cells/mouse Colo205 colorectal carcinoma cells or A549 lung carcinoma cells were injected intradermally into athymic nude mice having the indicated TEM8 or CMG2 genotypes. Tumors were measured with digital calipers (FV Fowler Company, Inc., Newton, Mass.) and tumor weights were estimated with the length, width, and height tumor dimensions using formulas: tumor weight (mg)=½(length in mm×width in mm$^2$) or ½(length in mm×width in mm×height in mm). Tumor-bearing mice were randomized into groups and injected intraperitoneally following schedules indicated in the figures, with PBS, the engineered toxins, a PC regimen, or a combined therapy. Mice were weighed and the tumors measured before each injection. All animal studies were carried out in accordance with protocols approved by the National Institute of Allergy and Infectious Diseases Animal Care and Use Committee.

Visualization of Blood Vessels with a Lipophilic Carbocyanine Dye DiI

The procedure was previously described (Li et al., *Nat. Protoc.,* 3: 1703-1708 (2008)). In brief, B16-BL6 tumor-bearing mice treated with three doses of 30 μg PA-L1 plus 15 μg LF or PBS were euthanized by CO$_2$ inhalation, followed immediately by sequential cardiac perfusion using PBS, DiI dye (Sigma), and 4% paraformaldehyde. Frozen tissue sections were then prepared for fluorescent microscopy to visualize vasculatures of tumors and various normal tissues. For tumor blood vessel quantifications, blood vessels were counted in five random views (11 min$^2$/view) from each tumor sample (n=3 for each treatment group).

Measurement of Toxin-Neutralizing Antibodies

B16-BL6 or LL3 tumor-bearing mice from various treatment groups were terminally bled and sera prepared. To titrate toxin neutralizing antibodies in the sera, RAW264.7 cells grown in 96-well plates were incubated with 100 ng/mL PA plus 100 ng/mL LF (amounts that kill >95% of the cells) in the presence of various dilutions of the sera for 5 h, followed by MTT assay to determine cell viabilities as described above.

Flow Cytometry

Spleens from naïve mice and the B16-BL6 melanoma-bearing mice from the groups treated with PBS, PC regimen, IC2-PA/LF, or the combined PC and the toxin were dissected and weighed after the second round treatments as shown in FIGS. 15A-15D. Splenocytes were isolated, counted, and stained with fluorochrome-conjugated mAbs anti-CD45R APC-Cy7 (Cat. No. 552094, BD Pharmingen), anti-CD4 APC (Cat. 553051, BD Pharmingen), anti-CD8 PE (Cat. 553033, BD Pharmingen), anti-CD11b PerCP-Cy5 (Cat. 550993, BD Pharmingen), and anti-Gr-1 FITC (Cat. 553127, BD Pharmingen), or anti-IgD FITC (Cat. 553439, BD Pharmingen), anti-IgM PE (Cat. 553409, BD Pharmingen), and anti-CD27 PerCP-Cy5 (Cat. 563603, BD Pharmingen). The cells were analyzed using a BD FACSCanto Flow Cytometer and percentages of each cell population positive for indicated immune cell markers were obtained. Cell numbers positive for each immune cell marker were obtained by: total splenocytes×% of the marker positive cells.

Statistical Analysis

Statistical analysis was done with unpaired Student's t test using EXCEL software. Survival curves were analyzed using log-rank test (Mantel-Cox) using GRAPHPAD PRISM software.

Example 4

This example demonstrates that CMG2 and TEM8 in tumor stromal compartments are not important for tumor growth.

Without being bound to a particular theory or mechanism, it is believed that the angiogenic process is necessary for tumor growth. To directly assess the roles of the anthrax toxin receptors CMG2 and TEM8 in tumor angiogenesis, the growth rates of three different solid tumors in previously described TEM8- and CMG2-null mice (Liu et al., *Proc. Natl. Acad. Sci. USA,* 106: 12424-12429 (2009)) were measured. The tumors evaluated were human lung carcinoma A549 xenografts and the syngeneic mouse LL3 Lewis lung carcinoma and B16-BL6 melanoma (FIGS. 6A, 6B, 6C, 6F, 6G, and 6H). Consistently, all three tumors grew as rapidly in CMG2-null mice as in their littermate control mice, indicating that CMG2 expression in tumor stromal compartments (e.g., endothelial cells and inflammatory cells) is not required for tumor growth (FIGS. 6A, 6B, and 6C). No differences in body weight were observed between the tumor-bearing littermate Cmg2$^{+/+}$, Cmg2$^{+/-}$, and Cmg2$^{-/-}$ mice (FIGS. 6F-6H).

In preliminary studies, it was observed that tumors grew more slowly in TEM8-null mice than in their littermate controls (FIGS. 12A, 12B, 12C, and 12D). However, it was found that nearly all Tem8$^{-/-}$ mice progressively developed misaligned overgrown incisor teeth (malocclusion) beginning at the time of weaning (3-weeks old), causing these mice to have difficulty in chewing the hard food that was routinely provided (FIG. 12D). Consequently, the Tem8$^{-/-}$ mice became malnourished, reflected in lower body weights associated with lack of subcutaneous fat deposition (FIGS. 12E, 12F, 12G, 12H, and 12I). The malnourished phenotypes became more pronounced as the Tem8$^{-/-}$ mice aged, leading to about 50% mortality at one-year of age. It was found that the Tem8$^{-/-}$ mice were completely rescued from malnourishment after providing soft food (Nutra-Gel from Bio-Serv, Frenchtown, N.J.) (FIGS. 12E, 12F, 12G, 12H, and 12I). Thus, the cause of the malnourished phenotype of Tem8$^{-/-}$ mice was their inability to obtain sufficient amounts of nutrients. Furthermore, the frequency of malocclusion seen in Tem8$^{-/-}$ mice was greatly decreased by soft food feeding (FIG. 12E). Therefore, TEM8$^{-/-}$ is essential in maintaining mouse tooth function required for the gnawing and chewing of hard food.

To investigate whether the decreases in tumor growth in Tem8$^{-/-}$ mice observed above were due to the malnourished phenotype, the syngeneic LL3 lung carcinomas and B16-BL6 melanomas were then grown in the soft food-fed, body weight-corrected Tem8$^{-/-}$ mice. Notably, no significant differences in tumor growth were now observed between littermate Tem8$^{-/-}$ and Tem8$^{+/+}$ mice (FIGS. 6D, 6E, 6I, and 6J). Taken together, the results above demonstrate that expression of neither CMG2 nor TEM8 in stromal compartments is important for tumor growth and, by implication, tumor angiogenesis.

Example 5

This example demonstrates that engineered anthrax lethal toxins block tumor growth through host CMG2.

To investigate the anti-tumor mechanisms of engineered lethal toxins, LL3 carcinoma-bearing mice and B16-BL6 melanoma-bearing mice were treated systemically with PA-L1 plus LF or IC2-PA plus LF. "IC2-PA" refers to the combination of PA-L1-I207R and PA-U2-R200A. These types of tumors were highly and equally sensitive to these engineered lethal toxins in vivo (FIGS. 7A, 7B, and 7C). LL3 cells were sensitive to the lethal toxins in in vitro cytotoxicity assay, whereas B16-BL6 cells were highly resistant (FIG. 7D). These results suggested that targeting certain cell-types in tumor stromal compartments may play a role in tumor responses to the toxins.

Because both CMG2$^{-/-}$ and TEM8$^{-/-}$ mice are able to support normal tumor growth, these mice provide powerful genetic tools to dissect the mechanisms by which the engineered anthrax toxins control tumor growth. To determine the role of stromal compartments in the potent anti-tumor activities of the engineered anthrax lethal toxins, A549 tumor-bearing Cmg2$^{-/-}$ and Tem8$^{-/-}$ mice and their littermate control mice were treated with PA-L1/LF after tumors had grown to about one gram. A549 cells contain wild-type BRAF and are resistant to PA-L1/LF in in vitro cytotoxicity assays (FIGS. 13A and 13B). While A549 tumors in Cmg2$^{+/+}$ and Cmg2$^{+/-}$ mice were very sensitive to the toxin, the tumors growing in Cmg2$^{-/-}$ mice were much less sensitive (FIGS. 7E and 7F). In contrast, the A549 tumors growing in Tem8$^{-/-}$ mice, as well as in their littermate control mice, all were sensitive to the toxin treatments (FIGS. 7G and 7H). These results clearly demonstrate that the anti-tumor activities of the engineered toxin involve targeting certain tumor stromal compartments. The results also reveal that CMG2 rather than TEM8 is the major toxin receptor mediating the anti-tumor activities of the toxin. In the presence of stromal CMG2 expression, the engineered toxin was highly potent, showing efficacy even for tumors that were very large in size (≈5% of total body weight) (FIGS. 7E, 7F, 7G, and 7H).

Example 6A

This example demonstrates that targeting tumor endothelial cells is responsible for the anti-tumor activities of the engineered anthrax lethal toxins.

To determine which cell-type in tumor stromal compartments is responsible for the anti-tumor action of PA-L1/LF, B16-BL6 tumors were inoculated into three types of mice: Cmg2$^{-/-}$ mice, Cmg2$^{-/-}$ mice with a CMG2-transgene expressed only in endothelial cells (named Cmg2$^{EC}$ hereafter, see Liu et al., *Nature*, 501: 63-68 (2013) for detailed description), and Cmg2$^{-/-}$ mice with a CMG2-transgene expressed only in vascular smooth muscle cells (Cmg2$^{SM}$) (see Liu et al., *Nature*, 501: 63-68 (2013) for detailed description). B16-BL6 cells are insensitive to PA-L/LF in in vitro cytotoxicity assays (FIG. 7D). As seen above for A549 tumors (FIG. 7E), B16-BL6 melanomas in Cmg2$^{-/-}$ mice were insensitive to PA-L1/LF, whereas the same tumors in Cmg2$^{+/+}$ mice were exquisitely sensitive (FIGS. 8A and 8B). While the B16-BL6 tumors in Cmg2$^{SM}$ mice were, like in Cmg2$^{-/-}$ mice, insensitive to the toxin, the tumors in Cmg2$^{EC}$ mice were fully sensitive (FIGS. 8A and 8B). Thus, CMG2 endothelial expression is sufficient to mediate the anti-tumor activities of the toxin. To further evaluate the role of targeting tumor endothelial cells in cancer targeted therapy, B16-BL6 tumors were grown in endothelial cell-specific CMG2-null (termed Cmg2(EC)$^{-/-}$ hereafter, see Liu et al., *Nature*, 501: 63-68 (2013) for detailed description) mice. The tumors in Cmg2(EC)$^{-/-}$ mice completely lost sensitivity to PA-L1/LF as well as to PA-IC2/LF (FIGS. 8C and 8D), whereas the tumors in myeloid CMG2-specific CMG2-null (Cmg2(Mye)$^{-/-}$, see reference Liu et al., *Cell Host Microbe*, 8: 455-462 (2010) for detailed description) mice remained sensitive to PA-IC2/LF (FIG. 8D). No anti-tumor activity was observed when PA-L1 was used alone, confirming that the antitumor activity of these toxins requires the action of LF, the enzymatic moiety of the toxins.

Taken together, the above results clearly demonstrate that the potent anti-tumor activities of the engineered anthrax toxins are due to the toxins' unique toxicities to the host-derived tumor endothelial cells rather than to other cell-types in the tumor stromal compartments, e.g., vascular smooth muscle cells and myeloid lineage cells. An additional observation was that the Cmg2$^{EC}$ mice used in the tumor trials were themselves (when tumor-free) highly resistant to challenge with PA-Li/LF, in that 100% of the Cmg2$^{EC}$ mice survived 5 doses of 50 μg PA-L1 plus 50 μg LF, a regimen that killed 50% of wild-type mice (FIG. 8E). These results indicate that the engineered toxins are selectively toxic to proliferating tumor endothelial cells rather than to the mostly quiescent normal endothelial cells that do not express MMPs or uPA. To test this hypothesis, blood vessels of B16-BL6 tumor-bearing mice treated with PBS or PA-L1/LF were labeled with the fluorescent lipophilic carbocyanine dye DiI by cardiac perfusion (Li et al., *Nat. Protoc.*, 3: 1703-1708 (2008)). During perfusion, DiI directly incorporates into endothelial cell membranes upon contact, allowing visualization by fluorescence microcopy of vasculature structures within tumors and normal tissues. Notably, no differences were detected in vasculature structures of various normal tissues, including the spleens, kidneys, livers, and hearts of the B16-BL6 tumor-bearing mice treated with PBS and the toxin. Remarkably, while blood vessels were abundant in the tumors treated with PBS, vessels in the tumors treated with PA-L1/LF were rarely detected (FIG. 8F), B16-BL6 melanomas and LLC carcinomas were also sectioned and histologically analyzed after the tumor-bearing mice were treated with PA-L1/LF or PBS. Extensive tumor necrosis (H&E staining) and decreases in cell proliferation (Ki67 staining) accompanied by loss of tumor vascular structures were readily detected in the toxin-treated B16-BL6 and LLC tumors. These results support the view that the engineered lethal toxins selectively damage tumor endothelial cells while sparing normal endothelial cells, CD31 and TUNEL co-staining was also performed on B16-BL6 tumors. Although extensive apoptotic tumor cell death was detected in PA-L1/LF-treated tumors, no apoptotic cell death was identified among the rarely detected tumor endothelial cells in the toxin-treated tumors, suggesting that the toxin may exert the antitumor effects through affecting endothelial cell proliferation rather than by inducing apoptosis.

Example 6B

This example demonstrates that engineered anthrax lethal toxins inhibit the proliferation of tumor endothelial cells.

Tumor endothelial cells were isolated from B16-BL6 tumors through intermolecular adhesion molecule 2 (ICAM2) sorting to investigate the toxic effects of the engineered toxins on tumor endothelial cells. The purity of the isolated endothelial cells was confirmed by another endothelial marker, CD31. Delivery of LF into the cytosol of endothelial cells by PAL1 was evidenced by the cleavage of MEK1 and MEK2, accompanied by a dramatic decrease in phosphorylation of ERK1/2, as measured by Western blotting using MEK, MEK2, ERK, and Phospho-ERK antibodies. Expression of the toxin-activating proteases by endothelial cells was also confirmed by the cells' susceptibilities to the protease-activated PA variants (PA, PA-L1 (MMP-activated PA variant), and PA-U2 (urokinase-activated PA variant)) in the presence of FP59. FP59 is a fusion protein of LF amino acids 1-254 and the catalytic domain of *Pseudomonas aeruginosa* exotoxin A that kills all cells by ADP ribosylation of eEF2 after delivery to cytosol by PA. To examine the cytotoxic effects of the toxin on tumor endothelial cells, the cells were treated with PA-L1/LF for 48 h and 72 h, respectively, followed by annexin V plus propidium iodide (PI) staining to identify apoptotic cells by flow cytometry. Although PA-L1 plus FP59 could induce dramatic apoptotic cell death 24 h after incubation, PA-L1 plus LF could not do so even after 72 h incubation. Although the engineered lethal toxin did not directly kill endothelial cells, the toxin displayed potent inhibitory effects on endothelial cell proliferation. Thus, Ki67 staining revealed that tumor endothelial cell proliferation nearly completely ceased after 72 h incubation with the toxin. The toxin's effects on endothelial cells could be fully replicated by trametinib (although much higher molar concentrations were required), a small molecule inhibitor of MEK1/2 approved by the Food and Drug Administration for treating patients having metastatic melanoma with BRAF$^{V600E}$ mutation. These data suggest that the inhibitory effects of the engineered toxins were through disruption of the MEK-ERK pathway.

Example 7

This example demonstrates the additional benefit of the engineered toxin in targeting tumors having the BRAF mutation.

Due to their unique action on tumor endothelial cells, the tumor-associated protease-activated anthrax lethal toxins exhibit potent anti-tumor activities even for the tumors composed of cancer cells that are insensitive to the toxins. However, a subset of human cancer cells have oncogenic BRAF mutations such as BRAF$^{V600E}$ that make the tumor cells dependent on the RAF-MEK-ERK pathway for survival while also making them exquisitely sensitive to anthrax lethal toxin (Abi-Habib et al., *Mol. Cancer Ther.*, 4: 1303-1310 (2005)). It was hypothesized that engineered anthrax lethal toxins would have additional benefit in treatment of solid tumors having the BRAF$^{V600E}$ mutation. To test this, human colorectal carcinoma Colo205 cells, which contain the oncogenic BRAF$^{V600E}$ mutation and are sensitive to PA-L1/LF in vitro (FIGS. 13A and 13B), were inoculated into littermate Cmg2$^{-/-}$ and Cmg2$^{+/+}$ mice and treated with PA-L1/LF. Significantly, Colo205 tumors in Cmg2$^{-/-}$ mice were sensitive to the toxin treatment, although the response to the toxin treatment was lower than the strong response of the tumors growing in Cmg2$^{+/+}$ mice (FIG. 14). These results suggest that in the 'toxin-sensitive' tumors, the anti-tumor activity of the toxin depends on targeting both tumor endothelial cells as well as the cancer cells.

Example 8

This example demonstrates the effects of anthrax lethal toxin on metabolism of tumor endothelial cells.

Tumor endothelial cells were isolated from B16-BL6 tumors to investigate the underlying mechanisms of the toxic effects of the engineered toxins on tumor endothelial cells. Notably, proliferation of the endothelial cells cultured in endothelial cell growth media was decreased significantly after the cells were incubated with PA-L1/LF for 72 h (FIG. 9A). The delivery of LF into the cytosol of endothelial cells by PA-L1 was evidenced by the cleavage of MEK2 after a 3-h incubation with the toxin. Images were taken of the live, MTT-stained endothelial cells after incubation with or without 5 μg/mL PA-L1 plus 0.5 μg/mL LF for 72 h. The relative lower density of the cells treated with the toxin was noted. Because cellular metabolism is crucial for all cellular processes, it was examined whether lethal toxin affected the bioenergetics of tumor endothelial cells. After incubation with PA-L1/LF for 24 h, the extracellular acidification rates (ECARs) and oxygen consumption rates (OCRs) of tumor endothelial cells were measured under basal conditions, and following additions of the mitochondrial inhibitors oligomycin (ATP synthase inhibitor), FCCP (mitochondrial oxidative phosphorylation uncoupler), and antimycin A (Complex III inhibitor). ECAR reflects cytosolic glycolytic activity whereas OCR reflects mitochondrial oxidative phosphorylation. The engineered toxin significantly inhibited endothelial cell glycolytic activity under basal conditions, as well as when mitochondria were inhibited (FIG. 9B). The up-regulation of glycolytic activity, which attempts to compensate for diminished energy production during mitochondria inhibition (by oligomycin and FCCP), was also compromised by the toxin (FIG. 9B). Furthermore, the basal OCRs, ATP production-coupled OCRs (OCR$_{ATP}$s), maximal respiration (MR), spare respiratory capacity (SRC), and cellular ATP levels of the endothelial cells were also remarkably decreased by the toxin (FIGS. 9C, 9D, and 9E). These results demonstrate that the toxin profoundly affects tumor endothelial cell metabolism through affecting glycolysis, as well as mitochondrial oxidative phosphorylation.

To explore the underlying mechanisms of the toxin's effects on metabolism of endothelial cells, the expression levels of key genes in central metabolism by real-time PCR analyses were surveyed. Surprisingly, many genes key to glucose uptake, glycolysis, tricarboxylic acid cycle, glutamine usage, as well as lipid synthesis were significantly down-regulated by PA-L1/LF (FIG. 9F). Because glucose and glutamine are two major carbon sources for energetic metabolism and macromolecule syntheses, and lipid synthesis provides essential plasma membrane building blocks for cell proliferation, the profound effects of the toxin on tumor growth can be attributed at least in part to the transcriptional repression of key metabolic genes demonstrated here.

Example 9

This example demonstrates that preventing antibody responses to the engineered toxin allows repeated courses of treatment.

The tumor-associated protease-activated anthrax toxins provide high tumor specificity and high anti-tumor efficacy. However, these bacterial proteins are foreign antigens to mammalian hosts and may induce neutralizing antibodies that prevent long-term use. Therefore, strategies for preventing an immune response may be useful.

To examine whether a combination of pentostatin and cyclophosphamide (PC) blocks production of antibodies that neutralize engineered anthrax toxins, a trial was performed using the highly metastatic LL3 (mouse) carcinomas established in syngeneic immunocompetent C57BL/6 mice. The tumor-bearing mice were treated with PBS, a PC regimen, IC2-PA/LF, or the combined therapy of the PC regimen and IC2-PA/LF, following the schedule shown in FIGS. 10A and 10B. For the combined treatment groups, the tumor-bearing mice were prepared with doses of PC 3 and 4 days prior to the first toxin treatment. The combined treatment groups were treated with a total of 4 cycles of toxin and PC, with intervals of 5-7 days between cycles. IC2-PA/LF alone showed strong anti-tumor effects (FIGS. 10A and 10B). Surprisingly, all of the combined treatments showed much higher anti-tumor efficacy at both early and late times, with the tumors remaining responsive to the treatments even after the 4$^{th}$ cycle of the therapy (FIGS. 10A-1B). Importantly, no mortality was observed in the low (15 µg IC2-PA+5 µg LF) and the medium (20 µg IC2-PA+6.7 µg LF) dose groups. In fact, the mice receiving the combined treatments were alive after 42 days, well after mice in the other groups had to be euthanized due to their high tumor burdens (FIG. 10A-10B). The PC regimen alone exhibited potent anti-tumor activities (FIG. 10A-10B). As expected, neutralizing antibodies were detected in all of the mice treated with the toxin alone. Antibodies were detected as early as 10 days after the first treatment, the time at which the tumors began to show decreases in response to the toxin (only) treatment. Strikingly, no neutralizing antibodies were detected in the tumor-bearing mice of the combined therapy group even after the 4$^{th}$ round of therapy (FIGS. 10C, 10D, and 10E).

This study was next extended to include therapy of another highly malignant syngeneic tumor, the B16-BL6 melanomas implanted in immunocompetent C57BL/6 mice. This experiment used a modified toxin and PC regimen as shown in FIGS. 15A-15B. The B16-BL6 melanoma-bearing mice were treated with PBS, IC2-PA/LF (30 Mg/10 µg), a PC regimen, or the combined therapy of the PC regimen and IC2-PA/LF twice in the first week and weekly in the following weeks (FIGS. 15A-15B). Again, the PC alone regimen had a significant anti-tumor effect (FIGS. 15A-15B), and the combined treatment showed remarkable efficacy, with the tumors remaining responsive to the treatments even after the 5th cycle of the therapy (FIGS. 15A-15B). Consistently, no neutralizing antibodies against the engineered toxin were detected in mice treated with the combined PC and the toxin even after the five cycles of therapy (FIGS. 15C-15D).

Taken together, the above results reveal that the combined toxin and PC therapy has remarkable and prolonged anti-tumor effects. It was demonstrated that the PC regimen contributes to the antitumor efficacy of the combined therapy not only by preventing the induction of neutralizing antibodies, thereby allowing multiple cycles of therapy, but also via its previously unrecognized anti-solid tumor activity. In vitro cytotoxicity assays showed that pentostatin and cyclophosphamide were not toxic to B16-BL6, LL3, and endothelial cells when used either alone or in combination (FIGS. 16A, 16B, 16C, and 16D), suggesting that the anti-solid tumor effects of PC discovered in this work might occur through effects on immune cell compartments that support tumor cell proliferation and survival.

Example 10

This example demonstrates the effects of pentostatin and cyclophosphamide on immune cells.

To investigate the effects of the PC regimen on immune cells, splenocytes were isolated from naïve mice and B16-BL6 melanoma-bearing mice from various treatment groups after the second round of treatments as shown in FIGS. 15A-15B. Flow cytometry analyses revealed that B-cell populations (CD45R$^+$, IgM$^+$, Ig$^+$ cells) were nearly completely depleted in the PC as well as in the combined therapy groups (FIG. 11A). To a lesser extent, T-cell populations (CD4$^+$, CD8$^+$, and CD27$^+$ cells) were also reduced in these treatment groups (FIGS. 11B and 11C). The PC regimen and the combined PC and toxin treatments did not affect granulocyte populations (CD11b$^+$ and Gr-1$^+$ cells). It was found that the numbers of CD11b$^+$ and Gr-1$^+$ granulocytes were significantly increased in the tumor-bearing mice when compared to the numbers in naïve mice regardless of treatment type, suggesting the existence of innate immune responses to the tumors (FIG. 11E). The IC2-PA/LF alone did not significantly affect these cell populations (FIGS. 11A, 11B, 11C, 11D, and 11E). Therefore, the above results clearly demonstrate that the PC regimen efficiently depletes lymphocytes, in particular B-cells, while sparing innate immunity. In agreement with PC's effects on lymphocytes, the total splenocytes of the mice treated with PC regimen alone or in combination with the toxin were also significantly decreased (FIG. 11E). Without being bound to a particular theory or mechanism, it is believed that the absence of a humoral immune response to the engineered toxins was due to the B-cell depletion caused by the PC regimen.

Examples 11-18

The following materials and methods were employed in the experiments of Examples 11-18.

Reagents

Enzymes for DNA manipulations and modifications were purchased from New England Biolabs (Beverly, Mass.). Dynabeads TALON was obtained from Invitrogen (Carlsbad, Calif.). PA and FP59 were prepared as described in Pomerantsev et al., *Protein Expr. Purif,* 80: 80-90 (2011); Liu et al., *Cell. Microbiol.,* 9: 977-987 (2007); and Gupta et al., *PLoS One,* 3: e3130 (2008). The extracellular domain (ECD) of CMG2 (amino acids 40-218) was produced in *Escherichia coli* with an N-terminal His6 tag (Santelli et al., *Nature,* 430: 905-908 (2004); Chen et al., *J. Biol. Chem.,* 282: 9834-9846 (2007)). The ECD of TEM8 (amino acids 35-227) with a C-terminal His6 sequence was expressed in CHO cells. The latter protein was concentrated and purified from the culture medium with a nickel-nitrilotriacetic acid column (Qiagen, Valencia, Calif.) and further purified by MONOQ column chromatography (GE Healthcare, Pittsburgh, Pa.). Minimum essential medium alpha, HEPES buffer, hygromycin B, Hanks' balanced salt solution (HBSS), and fetal bovine serum (FBS) were from Invitrogen. The mutagenic nucleoside triphosphates 8-oxo-2'-deoxyguanosine triphosphate (8-Oxo-dGTP) and 6-(2-deoxy-β-D-ribofuranosyl)-3,4-dihydro-8H-pyrimido-[4,5-c][1,2] oxazin-7-one triphosphate (dPTP) were purchased from Trilink Biotechnologies (San Diego, Calif.). Other chemical reagents were obtained from Sigma (St. Louis, Mo.).

Construction of a Randomly Mutated PAD4 Phage Display Library

Random mutagenesis of PAD4 was accomplished by PCR amplification with 10 ng of pYS5 template DNA and nucleotide analogues 8-oxo-dGTP and dPTP (Chen et al., *J. Biol. Chem.*, 282: 9834-9846 (2007); Zaccolo et al., *J. Mol. Biol.*, 255: 589-603 (1996)). The PCR reaction (a total volume of 25 µl) contained 2.5 units of Takara Ex TaqDNA polymerase (Clontech, Mountain View, Calif.), 1 µM each of forward primer 5'GCTT GAATTCATTCATTATGATAGAAATAAC3' (SEQ ID NO: 34) and reverse primer 5'AATTCAAGCTTCCTATCT-CATAGCCTTTTTT 3' (SEQ ID NO: 35) (with EcoRI and HindIII sites underlined and bolded, respectively), 2 mM MgCl$_2$, 10 mM Tris-HCl, pH 8.3, 50 mM KCl, 400 µM each of dATP, dCTP, dGTP, dTTP, 50 µM of 8-oxo-dGTP and 10 µM of dPTP. After forty-two cycles (94° C. for 1 min, 60° C. for 1.5 min, and 72° C. for 5 min), 1 µl of the amplified DNA was used in a secondary PCR in which the above conditions were used except that 8-oxo-dGTP and dPTP were omitted. The secondary PCR product was digested with EcoRI and HindIII, cloned into the T7Select10-3 phage display system, and packaged into bacteriophage according to the manufacturer's instructions (Novagen, Madison, Wis.).

Selection of CMG2- and TEM8-Specific PAD4 Variants Using Magnetic Beads

Bacteriophage libraries were selected for CMG2-specific clones by four rounds of panning with Dynabeads TALON. Each round of panning was begun by washing 1 mg Dynabeads TALON with TALON binding and washing buffer (50 mM Na Phosphate, pH 8.0, 300 mM NaCl, 5 mM MgCl$_2$, 0.01% Tween-20, and 100 µg/ml of bovine serum albumin), and then adding 10 µg of extracellular domain of CMG2. After incubation on a roller at 4° C. for 30 min, the beads were washed four times with the same buffer. Bacteriophage (1×10$^9$ particles) were then added to the mixture and incubated at 4° C. for 90 min. The beads were washed five times with the same buffer over total time periods of 10 min, 2 h, 5 h and 20 h in the four successive panning cycles. Following the final wash in each cycle, bacteriophage were eluted from the beads with 100 µl of TALON elution buffer (150 mM imidazole, 50 mM Na Phosphate, pH 8.0, 300 mM NaCl, 5 mM MgCl$_2$, 0.01% Tween-20, and 100 µg/ml of bovine serum albumin) by incubating the mixture on a roller for 10 min at 4° C. Phage were amplified by growth in *E. coli* BLT5403 and used in the next cycle of panning. To select TEM8-specific PAD4 variants, the experimental procedures described above were conducted except that 10 µg of extracellular domain of TEM8 was used for binding to the Dynabeads.

Sequencing of DNA Inserts in 77 Bacteriophage

Bacteriophage from the fourth round of panning were picked from individual bacteriophage plaques, suspended in M9LB broth (Novagen, Madison, Wis.) and set at room temperature for 2 h to allow bacteriophage particles to diffuse from the agar. EDTA was then added to the bacteriophage suspension to give a final concentration of 10 mM, and the suspension was heated at 65° C. for 10 min. One microliter of the sample was used for PCR amplification in reactions containing 2.5 units of Takara Ex TaqDNA polymerase, forward primer 5'TAAGTACGCAATGGGC-CACG3' (SEQ ID NO: 36), and reverse primer 5'AACTCA-GCGGCAGTCTCAAC3' (SEQ ID NO: 37), with PCR conditions as described above, except the annealing temperature was 50° C. The PCR product was sequenced by dideoxy-mediated sequencing reactions.

Construction of PA I656 and PA E654 Mutants

Cloning of mutated PA domain 4 sequences was done with plasmid pYS54, an expression vector having the silent restrictions sites StuI and XhoI at positions corresponding to amino acids 650-652 and 665-667, respectively (Chen et al., *J. Biol. Chem.*, 282: 9834-9846 (2007)). To obtain all 19 amino acid substitutions of either I656 or E654, oligonucleotides were synthesized having the sense strand sequence of SEQ ID NO: 38 and antisense strand sequence of SEQ ID NO: 39, where either (but not both) the E654 codon gaa or the I656 codon ata in the sense strand and the corresponding codons in the antisense strands were fully randomized. Additionally, mutants having R659S/M662R substitutions plus all 19 amino acid substitutions of E654 were made in a similar way by including the 659S and 662R codons in the oligonucleotides described above. In each case, double strand cassettes were obtained by heating the mixture of sense and antisense strands at 100° C. for 10 min and allowing the mixture to cool slowly to room temperature. The resulting products were digested with StuI and XhoI and ligated into pYS54 digested with the same restriction endonucleases, and the ligation mixtures were transformed into *E. coli* XL-1 Blue. Plasmid DNAs isolated from individual clones were sequenced to select all 20 amino acids substitutions.

Construction of PA Proteins with PAD4 Substitutions and Having a Modified Furin Site To prepare PA proteins having substitutions in residues identified as being involved in binding to CMG2 and TEM8 (I656, etc.) and also an uncleavable furin site, the pYS54 constructs described above were digested with PstI and HindIII, and the intervening region was replaced with the corresponding PstI to HindIII fragment isolated from a plasmid encoding PA-U7 (Liu et al., *J. Biol. Chem.*, 276: 17976-17984 (2001)), in which the $^{164}$RKKR$^{167}$ sequence is replaced by PGG. The doubly-substituted PA proteins derived from PA I656V and PA I656Q were accordingly named PA-U7 I656V and PA-U7 I656Q, respectively. In a similar way, altered furin site sequences were inserted into constructs having multiple substitutions, including the PA E654T/R659S/M662R protein (abbreviated PA TSR). In this case, alternative furin site sequences used included those from PA-U7 (as above) and PA-L1, the latter being one cleaved by matrix metalloproteases (Liu et al., *Cancer Res.*, 60: 6061-6067 (2000)). The doubly-mutated PA proteins derived from PA TSR were accordingly named as PA-U7 TSR and PA-L1 TSR.

Expression and Purification of PA Proteins

Plasmids encoding individual constructs described above were transformed into the nonvirulent *B. anthracis* strains BH450 or BH460 and transformants were grown in FA medium with 10 µg/ml kanamycin for 15 h at 37° C. (Pomerantsev et al., *Protein Expr. Purif.*, 80: 80-90 (2011)). PA proteins were concentrated from culture supernatants and purified by chromatography on a MONOQ column (GE Healthcare) by methods described previously (Pomerantsev et al., *Protein Expr. Purif.*, 80: 80-90 (2011); Park et al., *Protein Expr. Purif.*, 18: 293-302 (2000)).

Measurement of PA Affinity for Receptors

Schild plot analyses were used as described previously (Liu et al., *Proc. Natl. Acad. Sci. U.S.A.*, 106: 12424-12429 (2009); Ittelson et al., *Nature*, 242: 330-332 (1973)) to determine the affinity (apparent $K_d$) of PA variant proteins for cellular receptors. Briefly, the nontoxic PA-U7, PA-U7 I656Q, PA-U7 I656V, and PA-U7 TSR proteins were used as competitors to block the toxicity of wild-type PA to CHO cells. Multiple PA dose-response cytotoxicity assays were done, each in the presence of a different fixed concentration of the competitor. The midpoints on the dose-response curves (Ti) were plotted against the competitor concentration. Ti is the midpoint of the dose-response curve obtained at a particular fixed competitor concentration. To is the value of Ti with no competitor added. The intercept of the resulting line at the point where log((Ti/To)−1)=0 identifies the competitor concentration equal to the apparent $K_d$ value, a measure of the affinity of the competitor for the receptor used by the toxin to produce toxicity.

Cells and Culture Media

Parental wild type Chinese hamster ovary (CHO) cells (CHO WTP4) and the PA receptor-expressing CHO CMG2-C4 and CHO TEM8-T4 cells, which overexpress CMG2 and TEM8 respectively, are as described previously (Liu et al., *Cell. Microbiol.* 9: 977-987 (2007); Liu et al., *J. Biol. Chem.* 278: 5227-5234 (2003)). CHO cells were grown in Minimum essential medium alpha with 5% FBS, 2 mM glutamine, 5 mM HEPES, pH 7.4, and 50 µg/ml gentamicin, with or without 300 µg/ml hygromycin B. HeLa and SN12C cells were cultured in Dulbecco's modified Eagle's medium with 10% FBS, 2 mM glutamine, and 50 µg/ml gentamicin. Mouse embryonic fibroblast (MEF) cells were isolated from E13.5 embryos of the wild type, CMG2$^{-/-}$, TEM8$^{-/-}$ and CMG2$^{-/-}$/TEM8$^{-/-}$ mice (to be described below) as described previously (Liu et al., *Proc. Natl. Acad. Sci. U.S.A.*, 106: 12424-12429 (2009)) and cultured in Dulbecco's modified Eagle's medium with 10% FBS, 2 mM glutamine, and 50 µg/ml gentamicin. MEF cells were passaged at 85-90% confluence by splitting 1:4 and used within the first six passages.

Cytotoxicity Assays of Cultured Cells

Cells were plated at 10,000 cells/well in 96-well plates and cultured for 24 h before treatment. PA proteins, combined with 100 ng/ml of FP59 for CHO cells and with 400 ng/ml of FP59 for MEF cells, were added to cells to a final volume of 200 µl/well. Cell viability was assayed 48 h after treatment by replacing the medium with 50 µl of medium containing 2.5 mg/ml MTT (3-[4,5-dimethylthiazol-2-yl]-2,5-diphenyltetrazolium bromide). Medium was removed after 1 h of incubation at 37° C. and the blue pigment produced by viable cells was dissolved in 50 µl/well of 0.5% (w/v) SDS, 25 mM HCl, in 90% (v/v) isopropyl alcohol. Plates were vortexed and oxidized MTT was measured as $A_{570}$ using a microplate reader (Spectra Max 190, Molecular Devices, Sunnyvale, Calif.). Results were analyzed with PRISM software (GraphPad Software Inc., San Diego, Calif.) as percentage viability of control wells containing FP59 without PA. $EC_{50}$ values were determined by nonlinear regression sigmoidal dose-response analysis with variable slopes. Each assay was performed three times, and data from a representative assay are shown.

Lethality of PA Variants for Receptor-Deficient Mice

The CMG2$^{-/-}$, TEM8$^{-/-}$, and CMG2$^{-/-}$/TEM8$^{-/-}$ (double null) C57BL/6 mice used here were described previously (Liu et al., *Proc. Natl. Acad. Sci. U.S.A.*, 106: 12424-12429 (2009); Liu et al., *Nature*, 501: 63-68 (2013)). These mice and littermate control mice (all 8-10 weeks old) were challenged intraperitoneally with two doses of PA or PA variants along with FP59 (in 0.5 ml PBS, doses indicated in tables and figures) with a 2-day interval. Mice were observed for signs of malaise twice daily for one week following injection. All mice studies were carried out in accordance with protocols approved by the National Institute of Allergy and Infectious Diseases Animal Care and Use Committee.

Tumoricidal Activity of PA Variants

Athymic nude mice were injected intradermally with $1 \times 10^7$ HeLa cells/mouse, and tumor xenografts were allowed to grow to 0.05% of body mass. Tumor-bearing mice were randomized into groups and injected intraperitoneally at intervals of 2 or 3 days, as indicated in the figures, with six doses of PBS or the engineered toxins. Body weights and tumor masses were measured at 2 or 3 day intervals. Tumors were measured with digital calipers (FV Fowler Company, Inc., Newton, Mass.) and tumor weights were estimated with the length, width, and height tumor dimensions using formulas: tumor weight (mg)=½ (length in mm×width in mm2) or ½ (length in mm×width in mm×height in mm).

Example 11

This example demonstrates the selection of PAD4 mutants that bind to CMG2.

An improved panning procedure was developed using soluble forms of the extracellular domains of CMG2 and TEM8 bound to magnetic beads (Dynabeads TALON). The specific binding of the phage-displayed PAD4 to each type of beads was verified by showing that preincubation of the beads with 100 ng PA reduced phage binding by 90% (Table 1).

TABLE 1

Table 1: After binding of bacteriophage, the mixture was washed five times with binding and washing buffer for a total of 10 min and bacteriophage were eluted with elution buffer and titered.

| Treatments | Phage bound to Dynabeads |
|---|---|
| Exp #1 - CMG2 magnetic beads | |
| Control[a] | $7.5 \times 10^2$ |
| CMG2-mag beads | $6.6 \times 10^4$ |
| CMG2-mag beads + PA[b] | $5.6 \times 10^3$ |
| Exp #2 - TEM8 magnetic beads | |
| Control[a] | $7.4 \times 10^2$ |
| TEM8-mag beads | $7.0 \times 10^4$ |
| TEM8-mag beads + PA[b] | $5.6 \times 10^3$ |

[a]binding of bacteriophage to Dynabeads without addition of an extracellular domain.
[b]100 ng of PA was mixed with bacteriophage lysate before adding to the Dynabeads.

To enrich for PAD4 variants having high affinity, the stringency of washing in each successive amplification round was increased, using washing times of 10 min, 2 h, 5 h and 20 h. The number of phage increased 600-fold by the third round of panning. The fourth round of panning on CMG2 resulted in a 65% decrease in phage numbers (Table 2), possibly because the highest possible affinity had already been reached by the third round, and the prolonged 20-h washing removed some of these tightly binding phage. No similar effect was seen when panning on TEM8 beads. After the fourth round of panning, individual bacteriophage plaques were chosen and sequenced.

TABLE 2

Table 2: Experimental procedures were the same as described in Table 1, except the magnetic beads were washed for 10 min, 2 h, 5 h, and 20 h in 1st, 2nd, 3rd and 4th rounds of panning, respectively.

| Round of panning | Phage bound to Dynabeads |
|---|---|
| Expt. #1 - CMG2-magnetic beads | |
| 1st | $3.8 \times 10^4$ |
| 2nd | $3.8 \times 10^5$ |
| 3rd | $2.3 \times 10^7$ |
| 4th | $8.1 \times 10^6$ |
| Expt. #2 - TEM8-magnetic beads | |
| 1st | $7.0 \times 10^4$ |
| 2nd | $1.2 \times 10^7$ |
| 3rd | $1.1 \times 10^7$ |
| 4th | $4.5 \times 10^7$ |

A total of 104 phage clones were sequenced over the 420-base pair (bp) region corresponding to PA amino acids 596-735. These DNA sequences were aligned. The resulting amino acid sequences of the clones were determined. Among the resulting total of 43,680 bp examined, a total of 616 changes were found, for a mutation rate of 1.4%. However, this value and the subsequent analyses were for the phage library after selection for binding to CMG2. This selection will both eliminate the large fraction of sequences coding for misfolded or unstable proteins as well as those with specific surface residue changes that decrease receptor recognition. The selection is also expected to enrich for silent mutations. It was found that the number of substitutions in codon positions 1-3 were 207, 165, and 244, respectively. Thus, substitutions in the 3rd position, which are less likely to change the amino acid, were enriched, consistent with the expected elimination of clones having the most common mutagenic events—amino acid changes that decrease structure and/or function.

While mutation frequencies and other numerical values were calculated, these can be viewed only as estimates. Comparison of the DNA and amino acid sequences shows that many clones were related. The bp changes seen in multiple clones must have occurred in an early PCR cycle and then expanded into many progeny sequences. This illustrates that the clones are not independent, as would be needed to achieve an accurate statistical analysis.

Because 8-oxo-GTP causes A to C and T to G transversions and dPTP causes A to G and T to C transitions (Zaccolo et al., *J. Mol. Biol.*, 255: 589-603 (1996)), a broad spectrum of amino acid substitutions should be generated, although codons containing G and C will be less affected. Although there were multiple mutations in nearly every clone from the CMG2-selected library, strikingly, it was found that mutation of Ile656 to Val, in the region between 4136 and 417 (amino acids 656-665), occurred in 85 of the 86 clones sequenced, indicating that residue Ile656 has a role in the binding of PA to the CMG2 receptor. In contrast, the TEM8-selected library showed a greater diversity of substitutions. However, residue Glu654, in the same region as Ile656, was very frequently mutated. Thus, of the 95 random clones sequenced, 27 have Glu654 substituted by either Gly or Ala, indicating that this residue may have a role in the binding of PA to TEM8.

Example 12

This example demonstrates PAD4 variants having substitutions at Ile656.

To further characterize the role of Ile656 in binding of PA to TEM8, Ile656 was mutated to all other 19 amino acids. Substitutions of Ile656 with Leu, Met, Gln, Ser, Thr, Val, and Tyr were well tolerated, because these proteins retained cytotoxicity to the wild-type CHO WTP4 cells (Table 3). While these Ile656 mutants also retained activity to CHO CMG2-C4 cells, the CHO cell line that over-expresses only CMG2, all these PA variants displayed greatly decreased cytotoxicity to CHO TEM8-T4 cells, which over-express only TEM8. In particular, PA I656Q and I656S showed no cytotoxicity to CHO TEM8-T4 cells at the highest concentrations tested, 80 ng/ml. Therefore, PA I656Q and I656S are highly selective for CMG2. All other variants showed decreased cytotoxicity to all three types of CHO cells. PA I656W showed no cytotoxicity to the cell lines even at the highest concentration (80 ng/ml) tested (Table 3). Nearly all the I656 substitution variants showed a much greater loss of cytotoxicity toward the CHO TEM8-T4 cells than toward CHO CMG2-C4 and CHO WTP4 cells.

TABLE 3

Table 3: PA I656 mutants containing all 20 amino acids at position 656 were tested for toxicity to CHO cells. Values in the table are $EC_{50}$, the concentrations of the PA proteins that killed 50% of cells when combined with 100 ng/ml of FP59. The analyses were performed three times, and the averages are listed.

| PA variant | $EC_{50}$ (ng/ml) on CHO cells[#] | | | Selectivity for CMG2 vs. TEM8[$] |
|---|---|---|---|---|
| | WTP4 | TEM8-T4 | CMG2-C4 | |
| PA (native) | 0.14* | 0.21 | 0.05 | 4 |
| PA I656Q | 0.48* | >83.3 | 0.05 | >1667 |
| PA I656S | 0.42 | >83.3 | 0.07 | >1190 |
| PA I656N | 1.10 | >83.3 | 0.12 | >694 |
| PA I656H | 4.11 | >83.3 | 0.17 | >490 |
| PA I656E | 1.71 | >83.3 | 0.17 | >490 |
| PA I656A | 3.87 | >83.3 | 0.26 | >320 |
| PA I656G | 1.83 | >83.3 | 0.29 | >287 |
| PA I656K | 9.27 | >83.3 | 0.31 | >269 |
| PA I656C | 0.63* | 17.33 | 0.10 | 173 |
| PA I656M | 0.24 | 4.70 | 0.05 | 99 |
| PA I656Y | 2.13 | 13.61 | 0.14 | 99 |
| PA I656L | 0.22 | 3.71 | 0.04 | 92 |
| PA I656F | 1.76 | 7.29 | 0.12 | 61 |
| PA I656T | 0.28 | 1.59 | 0.03 | 53 |
| PA I656D | 15.33 | >83.3 | 1.91 | >44 |
| PA I656P | 2.76 | 5.25 | 0.22 | 24 |
| PA I656V | 0.35 | 1.34 | 0.06 | 22 |
| PA I656R | >83.3 | >83.3 | 5.33 | >16 |
| PA I656W | >83.3 | >83.3 | >83.3 | nc[#] |

[$]Ratio: ($EC_{50}$ for TEM8-T4)/($EC_{50}$ for CMG2-C4). Variants are sorted according to this value.
[#]nc is for not able to be calculated.
[#]In $EC_{50}$ values, standard deviations (SD) are indicated as follows:
No asterisk indicates that SD = <0.5 x the absolute value or cannot be calculated and one asterisk indicates that SD = 0.5-1.0 x the absolute value.

Example 13

This example demonstrates PAD4 variants having substitutions at Glu654.

To further characterize the role of position 654 in binding to CMG2, E654 was mutated to all other 19 amino acids. In many cases, the substitutions led to a greater reduction in potency toward CHO-CMG2-C4 than toward CHO-TEM8-T4 cells (Table 4), although the losses in potency were smaller than those caused by substitutions at I656 (Table 3). Only the substitution of Val was fully tolerated, as shown by the retention of toxicity toward both cell types. In contrast, substitution of Ala, Cys, Gly, His, Asn, Gln, Ser, Thr, Trp and Tyr caused decreases in potency toward CHO CMG2-C4 cells that were not paralleled by decreases in potency toward CHO TEM8-T4. In fact, many of these substitutions appeared to cause a slight increase in potency toward the CHO-TEM8-T4 cells, as seen particularly with the E654Q, E654V and E654W variants. These variants have a 2- to 3-fold higher toxicity toward CHO-TEM8-T4 than does native PA, indicating that the E654 residue plays a role in determining the relative affinities for the two receptors.

TABLE 4

Table 4: PA E654 variants containing all 20 amino acids at position 654 were tested for toxicity to CHO cells. Values in the table are $EC_{50}$, the concentrations of the PA proteins that killed 50% of cells when combined with 100 ng/ml of FP59. The analyses were performed three times, and the averages are listed.

| PA variant | $EC_{50}$ (ng/ml) on CHO cells[#] | | Selectivity for TEM8 vs. CMG2[$] |
|---|---|---|---|
| | TEM8-T4 | CMG2-C4 | |
| PA (native) | 0.52 | 0.39* | 0.7 |
| PA E654C | 0.16 | 0.81* | 4.9 |
| PA E654N | 0.16 | 0.68 | 4.3 |
| PA E654Q | 0.13 | 0.39 | 2.9 |
| PA E654S | 0.10 | 0.26* | 2.6 |
| PA E654H | 0.22 | 0.53 | 2.4 |
| PA E654F | 0.63 | 1.43 | 2.3 |
| PA E654Y | 0.16 | 0.36 | 2.3 |
| PA E654W | 0.15* | 0.34 | 2.2 |
| PA E654T | 0.42 | 0.89 | 2.1 |
| PA E654I | 0.73 | 1.27 | 1.7 |
| PA E654M | 0.35 | 0.58 | 1.7 |
| PA E654A | 0.54 | 0.88 | 1.6 |
| PA E654L | 0.52 | 0.70 | 1.3 |
| PA E654G | 0.58 | 0.59 | 1.0 |
| PA E654V | 0.19* | 0.20 | 1.0 |
| PA E654R | 2.40 | 1.12 | 0.5 |
| PA E654P | 7.20 | 2.80 | 0.4 |
| PA E654D | 2.40 | 0.83 | 0.3 |
| PA E654K | 2.50 | 0.50 | 0.2 |

[$]Ratio: ($EC_{50}$ for CMG2-C4)/($EC_{50}$ for TEM8-T4). Variants are sorted according to this value.
[#]In $EC_{50}$ values, standard deviations (SD) are indicated as follows:
No asterisk indicates that SD = <0.5 x the absolute value or cannot be calculated, and one asterisk indicates that SD = 0.5-1.0 x the absolute value.

Example 14

This example demonstrates PAD4 variants having substitutions in multiple residues.

To examine the effects of combining substitutions, PA variants were selected combining all 19 amino acids replacing E654 with the R659S/M662R substitutions. All 19 substitution mutants showed decreased toxicity toward CHO-CMG2-C4 cells (Table 5). Particularly, the PA variants KSR, PSR and RSR were nontoxic to CHO-CMG2-C4 cells when added at 80 ng/ml, the highest concentration tested. In contrast, variants PA ASR, GSR, HSR, MSR, NSR, QSR, SSR, TSR and WSR had potencies equal or slightly greater than that of native PA toward CHO-TEM8-T4 cells (Table 5). For example, PA TSR was 2-fold-more toxic to CHO-TEM8-T4 cells than native PA but 23-fold less toxic to CHO-CMG2-C4 cells. The PA QSR, MSR and GSR variants were similar to PA TSR, being only slightly less selective. Based on these data, PA MSR, QSR and TSR were selected for further study.

TABLE 5

Table 5: PA variants having R659S and M662R substitutions along with substitution of each of the other 19 amino acids at position 654 were tested for toxicity to CHO cells. The 3-letter designation identifies the non-native substitutions at positions 654, 659, and 662. Values in the table are $EC_{50}$, the concentration of the PA protein that produces 50% killing when combined with 100 ng/ml of FP59. The analyses were performed three times, and the averages are listed.

| PA variant | | $EC_{50}$ (ng/ml) on CHO cells* | | Selectivity for TEM8 vs. CMG2[$] |
|---|---|---|---|---|
| designation | Substitution (in addition to R659S/M662R) | TEM8-T4 | CMG2-C4 | |
| PA (native) | | 0.40 | 0.16 | 0.4 |
| MSR | E654M | 0.60 | 6.83 | 11.4 |
| TSR | E654T | 0.35 | 3.00 | 8.5 |
| QSR | E654Q | 0.44 | 3.20 | 7.3 |
| GSR | E654G | 0.49 | 3.47 | 7.1 |
| YSR | E654Y | 0.63 | 4.33 | 6.8 |
| VSR | E654V | 0.71 | 3.93 | 5.5 |
| RSR | E654R | 15.67 | >83 | >5.3 |
| LSR | E654L | 3.53 | 17.3 | 4.9 |
| FSR | E654F | 0.62 | 2.97 | 4.8 |
| ISR | E654I | 2.00 | 9.33 | 4.7 |
| NSR | E654N | 0.43 | 1.73 | 4.1 |
| CSR | E654C | 6.40 | 17.0 | 2.7 |
| SSR | E654S | 0.35 | 0.91* | 2.6 |
| KSR | E654K | 40.2 | >83 | >2 |
| HSR | E654H | 0.21 | 0.38 | 1.8 |
| ASR | E654A | 0.36 | 0.60 | 1.7 |
| WSR | E654W | 0.47 | 0.63 | 1.3 |
| DSR | E654D | 8.00 | 5.00 | 0.6 |
| PSR | E654P | >83 | >83 | nc[#] |

[$]Ratio: ($EC_{50}$ for CMG2-C4)/($EC_{50}$ for TEM8-T4).
[#]nc is for not able to be calculated.
[#]In $EC_{50}$ values, standard deviations (SD) are indicated as follows:
No asterisk indicates that SD = <0.5 x the absolute value or cannot be calculated, and one asterisk indicates that SD = 0.5-1.0 x the absolute value.

Example 15

This example demonstrates the cytotoxicity of PA variants to receptor-deficient mouse embryonic fibroblasts (MEFs).

While the CHO cell lines expressing a single receptor were essential in determining the preference of PA variants for CMG2 and TEM8, it was sought to verify the behavior of the PA proteins on other cell types. Mice having each receptor deleted, and cells isolated from them, provide a well-defined genetic system for examining the receptor specificity of the PA variants (Liu et al. *Cell Host Microbe*, 8: 455-462 (2010); Liu et al., *Nature*, 501: 63-68 (2013); Liu et al., *Toxins (Basel)*, 5: 1-8 (2012)). Cytotoxicity tests of the PA variants having substitutions at I656 (from Table 3) on MEFs isolated from these mice clearly demonstrated the high specificity of the PA I656 variants for CMG2 (Expt. 1, Table 6). The wild-type (WT) MEF cells appear to express both receptors, whereas the CMG2−/− MEFs are highly resistant to PA I656Q, while remaining sensitive to native PA and other variants which can use the remaining TEM8 receptor. The MEF cells from mice deleted for both receptors were highly resistant to all the PA variants, consistent with prior evidence that there are no physiologically significant receptors other than CMG2 and TEM8 (Liu et al., *Nature*, 501: 63-68 (2013); Liu et al., *Toxins (Basel)*, 5: 1-8 (2012)).

In a parallel experiment (Table 6, Expt. #2), the MEF was used again, and it was observed that the PA triple substitution variants such as PA TSR exert their toxicity through the TEM8 receptor, since absence of the CMG2 receptor has little effect on their potency, while absence of the TEM8 receptor decreases potency >100-fold. Taken together, these data using MEF cells confirm the selectivity of the PA variants that was seen in Tables 3 and 5.

TABLE 6

Table 6: PA variants were tested for cytotoxicity to the indicated MEF cells. Values in the table are $EC_{50}$, the concentrations of the PA proteins that killed 50% of cells when combined with 400 ng/ml of FP59. The analyses were performed two additional times with results similar to those presented.

| PA variant | $EC_{50}$ (ng/ml) on MEFs | | | |
|---|---|---|---|---|
| | WT | $CMG2^{-/-}$ | $TEM8^{-/-}$ | $CMG2^{-/-}$/$TEM8^{-/-}$ |
| | Expt. #1 | | | |
| PA (native) | 0.8 | 4.8 | 0.9 | >1000 |
| PA I656Q | 0.9 | >1000 | 0.9 | >1000 |
| PA I656V | 1.0 | 7.0 | 1.1 | >1000 |
| PA I656W | >1000 | >1000 | >1000 | >1000 |
| | Expt. #2 | | | |
| PA (native) | 0.9 | 17 | 1.0 | |
| PA MSR | 9.5 | 19 | >1,000 | |
| PA QSR | 9.0 | 16 | 700 | |
| PA TSR | 3.5 | 7 | 130 | |

Example 16

This example demonstrates the affinity of PA variants for receptors as determined by Schild plot analyses.

It was expected that the differences in toxicity of the PA variants as described above result principally from differences in receptor-binding affinities. To examine this hypothesis, apparent affinities were measured by competitive Schild plot analyses. These analyses require that the protein ligand be a nontoxic variant of the protein of interest. Nontoxic variants of the PA I656Q, PA I656V, and PA TSR proteins were constructed by replacing their furin cleavage sites, $^{164}$RKKR$^{167}$ (SEQ ID NO: 4), with the uncleavable sequence PGG of the previously characterized PA-U7 protein (Liu et al., *J. Biol. Chem.*, 276: 17976-17984 (2001)). The resulting PA-U7 I656Q, PA-U7 I656V, and PA-U7 TSR were used as nontoxic receptor binding competitors. Reciprocal plots of the midpoints of the dose-response curves performed in varying amounts of the competitors yielded apparent dissociation constants ($K_d$) for the apparent affinity of the competitors to the PA receptors. These analyses showed that PA I656Q retained affinity for CMG2 receptor but greatly lost affinity for the TEM8 receptor (Table 7, Expt. #1). Although PA I656V retained affinity for CMG2, it had moderately decreased affinity for TEM8. Conversely, PA-U7 TSR showed a decrease in affinity to CMG2 (Table 7, Expt. #2), consistent with its preference for TEM8.

TABLE 7

Table 7: Analyses were performed as described in the Methods section. PA-U7, PA-U7 I656V, and PA-U7 I656Q, and PA-U7 TSR were used as competitors for PA in cytotoxicity assays with the two cell lines listed. Schild plot analyses determined the apparent affinities of the competitors for the receptors on the two cell lines.

| | Kd (nM) on cell lines | |
|---|---|---|
| Competitor | CHO CMG2-C4 | CHO TEM8-T4 |
| | Expt. #1 | |
| PA-U7 | 8 | 25 |
| PA-U7 I656V | 8 | 46 |
| PA-U7 I656Q | 8 | >240 |
| | Expt. #2 | |
| PA-U7 | 12 | 35 |
| PA-U7 TSR | 48 | 30 |

Example 17

This example demonstrates the toxicity of PA variants to CMG2 and TEM8 knockout mice.

To explore whether the differing receptor specificities of the PA variants described above applied in vivo, $CMG2^{-/-}$ and/or $TEM8^{-/-}$ mice and their littermate control mice were challenged using 20 μg PA variants plus 20 μg FP59 (FIGS. 17A-17D). All the WT and $TEM8^{-/-}$ mice were killed by native PA+FP59 within 24 h (FIG. 17A), whereas most of the $CMG2^{-/-}$ mice survived to 48 h but succumbed to the second dose given at 48 h within the following 24 h, consistent with CMG2 being the major toxin receptor mediating mouse lethality. All the $CMG2^{-/-}$ mice survived two doses of the CMG2-selective PA I656Q+FP59 (FIG. 17B), while all their littermate control mice and $TEM8^{-/-}$ mice died, mostly within 24 h after the toxin challenge, demonstrating that the high specificity of PA I656Q for CMG2 extends to the case of intact mice. The moderate increase in specificity of PA I656V to CMG2 was also confirmed, as 50% the $CMG2^{-/-}$ mice survived to 75 h after receiving two doses of PA I656V+FP59 (FIG. 17C), while all $CMG2^{-/-}$ mice had succumbed by this time after challenge with the native PA+FP59 (FIGS. 17A and 17C, compared).

Comparison of the potency of the putatively TEM8-specific PA TSR variant toward wild type and CMG2-null mice produced the results shown in FIG. 17D. The PA TSR variant was much less toxic toward wild type mice than native PA, consistent with the CMG2 receptor being the main determinant of toxin sensitivity. However, PA TSR was more potent toward the CMG2-null mice than toward wild type mice. In the CMG2-null mice, death must result from targeting the TEM8 receptor in certain (unidentified) tissues, and PA TSR appeared to do this more efficiently than native PA.

Example 18

This example demonstrates the tumoricidal activity of PA variants to human HeLa xenografts in mice.

To examine the effects of altering PA's receptor specificity on its tumor-targeting ability, two of the PA variants were tested against HeLa cell xenografts in mice, in comparison to the previously described PA-L1 variant. The PA variants used here contained the MMP-specific L1 sequence at the furin site so as to achieve tumor specificity, and the effector used was LF rather than FP59. Mice bearing solid intradermal tumor nodules constituting ≈0.05% of the total body mass were challenged by intraperitoneal injection of six doses of the toxins at 2- or 3-day intervals. At the doses used, mouse body weights did not differ between the groups (FIG.

18A). In addition, the mice showed no outward sign of illness or gross abnormalities. However, large differences were seen in the effect of the PA variants on tumor size. Both PA-L1 and PA-L1 I656Q had strong and similar anti-tumor activities, reducing tumor size by >80% compared to PBS-treated tumors (FIG. 18B). In contrast, the tumors showed less response to treatment with PA-L1 TSR, with only a 50% reduction of tumor size occurring (FIG. 18B). These data are consistent with other evidence that targeting of tumors is most effective when PA acts through CMG2 rather than TEM8.

Example 19

This example demonstrates a method of treating oral melanoma in cats by administering IC2-PA and LF.

In a phase 0 trial with a goal to establish preliminary safety and efficacy data, five cats were enrolled and treated with a microdose (15 μg PA-U2-R200A+15 μg PA-L1-I207R+10 μg LF, defined as less than 1/100th of an observed safe dose in mice) three times in a week by intratumoral injection. All of the cats tolerated the treatments well with no significant side effects. Two cats had an increase in grooming behavior and ability to eat. One cat had a 31% reduction in tumor volume after three injections of IC2-PA+LF, as measured by computerized tomography (CT) scan. Four cats had stable disease. Histology analyses showed the rate of tumor cell apoptosis was significantly increased in three cats.

Encouraged by the results of the phase 0 trial, a combined phase I/II dose dose-finding and efficacy trial was initiated. The first and second cohorts of this trial received six injections of a dose 5× or 25× greater than in the phase 0 trial, respectively. A reduction in tumor volume has been observed in three of the five cats with no adverse effects. The trial is currently ongoing.

Example 20

This example demonstrates a method of treating oral melanoma in dogs by administering IC2-PA and LF.

In this ongoing phase 1 trial, two dogs with oral melanoma were enrolled and treated with 375 μg PA-U2-R200A+375 μg PA-L1-I207R+250 μg LF, three times a week for two weeks by intratumoral injection, followed by surgical removal of the tumors. The two dogs tolerated the treatments well with no significant side effects. The dogs' body weight and tumor sizes were measured throughout the study. The results are shown in FIGS. 19A-19D. One dog had a 50% reduction in tumor volume (FIG. 19A) and the other experienced a modest reduction (FIG. 19C). The trial is currently ongoing.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A composition comprising a first *Bacillus anthracis* protective antigen (PA) comprising a first PA amino acid sequence and a second PA comprising a second PA amino acid sequence, wherein the second PA amino acid sequence is different from the first PA amino acid sequence,
   wherein amino acid residue I207 of the first PA amino acid sequence, as defined by reference to SEQ ID NO: 1, is substituted with arginine,
   wherein furin cleavage sequence RKKR (SEQ ID NO: 4) of the first PA amino acid sequence is replaced with a matrix metalloproteinase (MMP) sequence comprising SEQ ID NO: 6,
   wherein amino acid residue R200 of the second PA amino acid sequence, as defined by reference to SEQ ID NO: 1, is substituted with alanine, and
   wherein furin cleavage sequence RKKR (SEQ ID NO: 4) of the second PA amino acid sequence is replaced with a urokinase plasminogen activator (uPA) sequence comprising SEQ ID NO: 9.

2. The composition according to claim 1, wherein amino acid residue I656 of the first PA amino acid sequence, the second PA amino acid sequence, or both the first and second PA amino acid sequence, as defined by reference to SEQ ID NO: 1, is substituted.

3. The composition according to claim 2, wherein amino acid residue I656 of the first PA amino acid sequence, the second PA amino acid sequence, or both the first and second PA amino acid sequence, is substituted with glutamine, valine, alanine, cysteine, or glutamic acid.

4. The composition according to claim 3,
   wherein amino acid residue I656 of the first PA amino acid sequence is substituted with glutamine, and
   wherein amino acid residue I656 of the second PA amino acid sequence is substituted with glutamine.

5. The composition according to claim 1, further comprising one or more of (i) *Bacillus anthracis* lethal factor (LF) and (ii) *Bacillus anthracis* edema factor (EF).

* * * * *

SEQUENCE LISTING

```
<160> NUMBER OF SEQ ID NOS: 39

<210> SEQ ID NO 1
<211> LENGTH: 735
<212> TYPE: PRT
<213> ORGANISM: Bacillus anthracis

<400> SEQUENCE: 1

Glu Val Lys Gln Glu Asn Arg Leu Leu Asn Glu Ser Glu Ser Ser Ser
1               5                   10                  15

Gln Gly Leu Leu Gly Tyr Tyr Phe Ser Asp Leu Asn Phe Gln Ala Pro
            20                  25                  30
```

-continued

```
Met Val Val Thr Ser Ser Thr Thr Gly Asp Leu Ser Ile Pro Ser Ser
             35                  40                  45
Glu Leu Glu Asn Ile Pro Ser Glu Asn Gln Tyr Phe Gln Ser Ala Ile
 50                  55                  60
Trp Ser Gly Phe Ile Lys Val Lys Lys Ser Asp Glu Tyr Thr Phe Ala
 65                  70                  75                  80
Thr Ser Ala Asp Asn His Val Thr Met Trp Val Asp Asp Gln Glu Val
                 85                  90                  95
Ile Asn Lys Ala Ser Asn Ser Asn Lys Ile Arg Leu Glu Lys Gly Arg
                100                 105                 110
Leu Tyr Gln Ile Lys Ile Gln Tyr Gln Arg Glu Asn Pro Thr Glu Lys
            115                 120                 125
Gly Leu Asp Phe Lys Leu Tyr Trp Thr Asp Ser Gln Asn Lys Lys Glu
130                 135                 140
Val Ile Ser Ser Asp Asn Leu Gln Leu Pro Glu Leu Lys Gln Lys Ser
145                 150                 155                 160
Ser Asn Ser Arg Lys Arg Ser Thr Ser Ala Gly Pro Thr Val Pro
                165                 170                 175
Asp Arg Asp Asn Asp Gly Ile Pro Asp Ser Leu Glu Val Glu Gly Tyr
                180                 185                 190
Thr Val Asp Val Lys Asn Lys Arg Thr Phe Leu Ser Pro Trp Ile Ser
            195                 200                 205
Asn Ile His Glu Lys Lys Gly Leu Thr Lys Tyr Lys Ser Ser Pro Glu
            210                 215                 220
Lys Trp Ser Thr Ala Ser Asp Pro Tyr Ser Asp Phe Glu Lys Val Thr
225                 230                 235                 240
Gly Arg Ile Asp Lys Asn Val Ser Pro Glu Ala Arg His Pro Leu Val
                245                 250                 255
Ala Ala Tyr Pro Ile Val His Val Asp Met Glu Asn Ile Ile Leu Ser
                260                 265                 270
Lys Asn Glu Asp Gln Ser Thr Gln Asn Thr Asp Ser Gln Thr Arg Thr
            275                 280                 285
Ile Ser Lys Asn Thr Ser Thr Ser Arg Thr His Thr Ser Glu Val His
            290                 295                 300
Gly Asn Ala Glu Val His Ala Ser Phe Phe Asp Ile Gly Gly Ser Val
305                 310                 315                 320
Ser Ala Gly Phe Ser Asn Ser Asn Ser Ser Thr Val Ala Ile Asp His
                325                 330                 335
Ser Leu Ser Leu Ala Gly Glu Arg Thr Trp Ala Glu Thr Met Gly Leu
            340                 345                 350
Asn Thr Ala Asp Thr Ala Arg Leu Asn Ala Asn Ile Arg Tyr Val Asn
            355                 360                 365
Thr Gly Thr Ala Pro Ile Tyr Asn Val Leu Pro Thr Thr Ser Leu Val
            370                 375                 380
Leu Gly Lys Asn Gln Thr Leu Ala Thr Ile Lys Ala Lys Glu Asn Gln
385                 390                 395                 400
Leu Ser Gln Ile Leu Ala Pro Asn Asn Tyr Tyr Pro Ser Lys Asn Leu
                405                 410                 415
Ala Pro Ile Ala Leu Asn Ala Gln Asp Asp Phe Ser Ser Thr Pro Ile
                420                 425                 430
Thr Met Asn Tyr Asn Gln Phe Leu Glu Leu Glu Lys Thr Lys Gln Leu
            435                 440                 445
```

```
Arg Leu Asp Thr Asp Gln Val Tyr Gly Asn Ile Ala Thr Tyr Asn Phe
    450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
                485                 490                 495

Asp Leu Asn Leu Val Glu Arg Arg Ile Ala Ala Val Asn Pro Ser Asp
                500                 505                 510

Pro Leu Glu Thr Thr Lys Pro Asp Met Thr Leu Lys Glu Ala Leu Lys
            515                 520                 525

Ile Ala Phe Gly Phe Asn Glu Pro Asn Gly Asn Leu Gln Tyr Gln Gly
    530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
                565                 570                 575

Val Leu Asp Lys Ile Lys Leu Asn Ala Lys Met Asn Ile Leu Ile Arg
                580                 585                 590

Asp Lys Arg Phe His Tyr Asp Arg Asn Asn Ile Ala Val Gly Ala Asp
            595                 600                 605

Glu Ser Val Val Lys Glu Ala His Arg Glu Val Ile Asn Ser Ser Thr
    610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
                645                 650                 655

Asn Asp Arg Tyr Asp Met Leu Asn Ile Ser Ser Leu Arg Gln Asp Gly
                660                 665                 670

Lys Thr Phe Ile Asp Phe Lys Lys Tyr Asn Asp Lys Leu Pro Leu Tyr
            675                 680                 685

Ile Ser Asn Pro Asn Tyr Lys Val Asn Val Tyr Ala Val Thr Lys Glu
    690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
                725                 730                 735

<210> SEQ ID NO 2
<211> LENGTH: 764
<212> TYPE: PRT
<213> ORGANISM: Bacillus anthracis

<400> SEQUENCE: 2

Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val Lys
                20                  25                  30

Gln Glu Asn Arg Leu Leu Asn Glu Ser Glu Ser Ser Gln Gly Leu
            35                  40                  45

Leu Gly Tyr Tyr Phe Ser Asp Leu Asn Phe Gln Ala Pro Met Val Val
    50                  55                  60

Thr Ser Ser Thr Thr Gly Asp Leu Ser Ile Pro Ser Ser Glu Leu Glu
65                  70                  75                  80

Asn Ile Pro Ser Glu Asn Gln Tyr Phe Gln Ser Ala Ile Trp Ser Gly
                85                  90                  95
```

-continued

```
Phe Ile Lys Val Lys Lys Ser Asp Glu Tyr Thr Phe Ala Thr Ser Ala
            100                 105                 110

Asp Asn His Val Thr Met Trp Val Asp Gln Glu Val Ile Asn Lys
        115                 120                 125

Ala Ser Asn Ser Asn Lys Ile Arg Leu Glu Lys Gly Arg Leu Tyr Gln
        130                 135                 140

Ile Lys Ile Gln Tyr Gln Arg Glu Asn Pro Thr Glu Lys Gly Leu Asp
145                 150                 155                 160

Phe Lys Leu Tyr Trp Thr Asp Ser Gln Asn Lys Lys Glu Val Ile Ser
                165                 170                 175

Ser Asp Asn Leu Gln Leu Pro Glu Leu Lys Gln Lys Ser Ser Asn Ser
            180                 185                 190

Arg Lys Lys Arg Ser Thr Ser Ala Gly Pro Thr Val Pro Asp Arg Asp
        195                 200                 205

Asn Asp Gly Ile Pro Asp Ser Leu Glu Val Glu Gly Tyr Thr Val Asp
    210                 215                 220

Val Lys Asn Lys Arg Thr Phe Leu Ser Pro Trp Ile Ser Asn Ile His
225                 230                 235                 240

Glu Lys Lys Gly Leu Thr Lys Tyr Lys Ser Ser Pro Glu Lys Trp Ser
                245                 250                 255

Thr Ala Ser Asp Pro Tyr Ser Asp Phe Glu Lys Val Thr Gly Arg Ile
            260                 265                 270

Asp Lys Asn Val Ser Pro Glu Ala Arg His Pro Leu Val Ala Ala Tyr
        275                 280                 285

Pro Ile Val His Val Asp Met Glu Asn Ile Ile Leu Ser Lys Asn Glu
    290                 295                 300

Asp Gln Ser Thr Gln Asn Thr Asp Ser Gln Thr Arg Thr Ile Ser Lys
305                 310                 315                 320

Asn Thr Ser Thr Ser Arg Thr His Thr Ser Glu Val His Gly Asn Ala
                325                 330                 335

Glu Val His Ala Ser Phe Phe Asp Ile Gly Gly Ser Val Ser Ala Gly
            340                 345                 350

Phe Ser Asn Ser Asn Ser Ser Thr Val Ala Ile Asp His Ser Leu Ser
        355                 360                 365

Leu Ala Gly Glu Arg Thr Trp Ala Glu Thr Met Gly Leu Asn Thr Ala
    370                 375                 380

Asp Thr Ala Arg Leu Asn Ala Asn Ile Arg Tyr Val Asn Thr Gly Thr
385                 390                 395                 400

Ala Pro Ile Tyr Asn Val Leu Pro Thr Thr Ser Leu Val Leu Gly Lys
                405                 410                 415

Asn Gln Thr Leu Ala Thr Ile Lys Ala Lys Glu Asn Gln Leu Ser Gln
            420                 425                 430

Ile Leu Ala Pro Asn Asn Tyr Tyr Pro Ser Lys Asn Leu Ala Pro Ile
        435                 440                 445

Ala Leu Asn Ala Gln Asp Asp Phe Ser Ser Thr Pro Ile Thr Met Asn
    450                 455                 460

Tyr Asn Gln Phe Leu Glu Leu Glu Lys Thr Lys Gln Leu Arg Leu Asp
465                 470                 475                 480

Thr Asp Gln Val Tyr Gly Asn Ile Ala Thr Tyr Asn Phe Glu Asn Gly
                485                 490                 495

Arg Val Arg Val Asp Thr Gly Ser Asn Trp Ser Glu Val Leu Pro Gln
            500                 505                 510
```

```
Ile Gln Glu Thr Thr Ala Arg Ile Ile Phe Asn Gly Lys Asp Leu Asn
            515                 520                 525

Leu Val Glu Arg Arg Ile Ala Ala Val Asn Pro Ser Asp Pro Leu Glu
        530                 535                 540

Thr Thr Lys Pro Asp Met Thr Leu Lys Glu Ala Leu Lys Ile Ala Phe
545                 550                 555                 560

Gly Phe Asn Glu Pro Asn Gly Asn Leu Gln Tyr Gln Gly Lys Asp Ile
                565                 570                 575

Thr Glu Phe Asp Phe Asn Phe Asp Gln Gln Thr Ser Gln Asn Ile Lys
            580                 585                 590

Asn Gln Leu Ala Glu Leu Asn Ala Thr Asn Ile Tyr Thr Val Leu Asp
        595                 600                 605

Lys Ile Lys Leu Asn Ala Lys Met Asn Ile Leu Ile Arg Asp Lys Arg
610                 615                 620

Phe His Tyr Asp Arg Asn Asn Ile Ala Val Gly Ala Asp Glu Ser Val
625                 630                 635                 640

Val Lys Glu Ala His Arg Glu Val Ile Asn Ser Ser Thr Glu Gly Leu
                645                 650                 655

Leu Leu Asn Ile Asp Lys Asp Ile Arg Lys Ile Leu Ser Gly Tyr Ile
            660                 665                 670

Val Glu Ile Glu Asp Thr Glu Gly Leu Lys Glu Val Ile Asn Asp Arg
        675                 680                 685

Tyr Asp Met Leu Asn Ile Ser Ser Leu Arg Gln Asp Gly Lys Thr Phe
690                 695                 700

Ile Asp Phe Lys Lys Tyr Asn Asp Lys Leu Pro Leu Tyr Ile Ser Asn
705                 710                 715                 720

Pro Asn Tyr Lys Val Asn Val Tyr Ala Val Thr Lys Glu Asn Thr Ile
                725                 730                 735

Ile Asn Pro Ser Glu Asn Gly Asp Thr Ser Thr Asn Gly Ile Lys Lys
            740                 745                 750

Ile Leu Ile Phe Ser Lys Lys Gly Tyr Glu Ile Gly
        755                 760

<210> SEQ ID NO 3
<211> LENGTH: 29
<212> TYPE: PRT
<213> ORGANISM: Bacillus anthracis

<400> SEQUENCE: 3

Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala
            20                  25

<210> SEQ ID NO 4
<211> LENGTH: 4
<212> TYPE: PRT
<213> ORGANISM: Bacillus anthracis

<400> SEQUENCE: 4

Arg Lys Lys Arg
1

<210> SEQ ID NO 5
<211> LENGTH: 764
<212> TYPE: PRT
<213> ORGANISM: Bacillus anthracis
```

<400> SEQUENCE: 5

```
Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val Lys
            20                  25                  30

Gln Glu Asn Arg Leu Leu Asn Glu Ser Glu Ser Ser Gln Gly Leu
        35                  40                  45

Leu Gly Tyr Tyr Phe Ser Asp Leu Asn Phe Gln Ala Pro Met Val Val
    50                  55                  60

Thr Ser Thr Thr Gly Asp Leu Ser Ile Pro Ser Ser Glu Leu Glu
65                  70                  75                  80

Asn Ile Pro Ser Glu Asn Gln Tyr Phe Gln Ser Ala Ile Trp Ser Gly
                85                  90                  95

Phe Ile Lys Val Lys Lys Ser Asp Glu Tyr Thr Phe Ala Thr Ser Ala
                100                 105                 110

Asp Asn His Val Thr Met Trp Val Asp Asp Gln Glu Val Ile Asn Lys
            115                 120                 125

Ala Ser Asn Ser Asn Lys Ile Arg Leu Glu Lys Gly Arg Leu Tyr Gln
130                 135                 140

Ile Lys Ile Gln Tyr Gln Arg Glu Asn Pro Thr Glu Lys Gly Leu Asp
145                 150                 155                 160

Phe Lys Leu Tyr Trp Thr Asp Ser Gln Asn Lys Lys Glu Val Ile Ser
                165                 170                 175

Ser Asp Asn Leu Gln Leu Pro Glu Leu Lys Gln Lys Ser Ser Asn Ser
            180                 185                 190

Arg Lys Lys Arg Ser Thr Ser Ala Gly Pro Thr Val Pro Asp Arg Asp
        195                 200                 205

Asn Asp Gly Ile Pro Asp Ser Leu Glu Val Glu Gly Tyr Thr Val Asp
    210                 215                 220

Val Lys Asn Lys Arg Thr Phe Leu Ser Pro Trp Ile Ser Asn Ile His
225                 230                 235                 240

Glu Lys Lys Gly Leu Thr Lys Tyr Lys Ser Ser Pro Glu Lys Trp Ser
                245                 250                 255

Thr Ala Ser Asp Pro Tyr Ser Asp Phe Glu Lys Val Thr Gly Arg Ile
            260                 265                 270

Asp Lys Asn Val Ser Pro Glu Ala Arg His Pro Leu Val Ala Ala Tyr
        275                 280                 285

Pro Ile Val His Val Asp Met Glu Asn Ile Ile Leu Ser Lys Asn Glu
    290                 295                 300

Asp Gln Ser Thr Gln Asn Thr Asp Ser Gln Thr Arg Thr Ile Ser Lys
305                 310                 315                 320

Asn Thr Ser Thr Ser Arg Thr His Thr Ser Glu Val His Gly Asn Ala
                325                 330                 335

Glu Val His Ala Ser Phe Phe Asp Ile Gly Gly Ser Val Ser Ala Gly
            340                 345                 350

Phe Ser Asn Ser Asn Ser Ser Thr Val Ala Ile Asp His Ser Leu Ser
        355                 360                 365

Leu Ala Gly Glu Arg Thr Trp Ala Glu Thr Met Gly Leu Asn Thr Ala
    370                 375                 380

Asp Thr Ala Arg Leu Asn Ala Asn Ile Arg Tyr Val Asn Thr Gly Thr
385                 390                 395                 400

Ala Pro Ile Tyr Asn Val Leu Pro Thr Thr Ser Leu Val Leu Gly Lys
                405                 410                 415
```

```
Asn Gln Thr Leu Ala Thr Ile Lys Ala Lys Glu Asn Gln Leu Ser Gln
            420                 425                 430

Ile Leu Ala Pro Asn Asn Tyr Tyr Pro Ser Lys Asn Leu Ala Pro Ile
        435                 440                 445

Ala Leu Asn Ala Gln Asp Asp Phe Ser Ser Thr Pro Ile Thr Met Asn
450                 455                 460

Tyr Asn Gln Phe Leu Glu Leu Glu Lys Thr Lys Gln Leu Arg Leu Asp
465                 470                 475                 480

Thr Asp Gln Val Tyr Gly Asn Ile Ala Thr Tyr Asn Phe Glu Asn Gly
                485                 490                 495

Arg Val Arg Val Asp Thr Gly Ser Asn Trp Ser Glu Val Leu Pro Gln
            500                 505                 510

Ile Gln Glu Thr Thr Ala Arg Ile Ile Phe Asn Gly Lys Asp Leu Asn
        515                 520                 525

Leu Val Glu Arg Arg Ile Ala Ala Val Asn Pro Ser Asp Pro Leu Glu
    530                 535                 540

Thr Thr Lys Pro Asp Met Thr Leu Lys Glu Ala Leu Lys Ile Ala Phe
545                 550                 555                 560

Gly Phe Asn Glu Pro Asn Gly Asn Leu Gln Tyr Gln Gly Lys Asp Ile
                565                 570                 575

Thr Glu Phe Asp Phe Asn Phe Asp Gln Gln Thr Ser Gln Asn Ile Lys
            580                 585                 590

Asn Gln Leu Ala Glu Leu Asn Val Thr Asn Ile Tyr Thr Val Leu Asp
        595                 600                 605

Lys Ile Lys Leu Asn Ala Lys Met Asn Ile Leu Ile Arg Asp Lys Arg
    610                 615                 620

Phe His Tyr Asp Arg Asn Asn Ile Ala Val Gly Ala Asp Glu Ser Val
625                 630                 635                 640

Val Lys Glu Ala His Arg Glu Val Ile Asn Ser Ser Thr Glu Gly Leu
                645                 650                 655

Leu Leu Asn Ile Asp Lys Asp Ile Arg Lys Ile Leu Ser Gly Tyr Ile
            660                 665                 670

Val Glu Ile Glu Asp Thr Glu Gly Leu Lys Glu Val Ile Asn Asp Arg
        675                 680                 685

Tyr Asp Met Leu Asn Ile Ser Ser Leu Arg Gln Asp Gly Lys Thr Phe
    690                 695                 700

Ile Asp Phe Lys Lys Tyr Asn Asp Lys Leu Pro Leu Tyr Ile Ser Asn
705                 710                 715                 720

Pro Asn Tyr Lys Val Asn Val Tyr Ala Val Thr Lys Glu Asn Thr Ile
                725                 730                 735

Ile Asn Pro Ser Glu Asn Gly Asp Thr Ser Thr Asn Gly Ile Lys Lys
            740                 745                 750

Ile Leu Ile Phe Ser Lys Lys Gly Tyr Glu Ile Gly
        755                 760

<210> SEQ ID NO 6
<211> LENGTH: 8
<212> TYPE: PRT
<213> ORGANISM: Artificial sequence
<220> FEATURE:
<223> OTHER INFORMATION: synthetic

<400> SEQUENCE: 6

Gly Pro Leu Gly Met Leu Ser Gln
1               5
```

```
<210> SEQ ID NO 7
<211> LENGTH: 8
<212> TYPE: PRT
<213> ORGANISM: Artificial sequence
<220> FEATURE:
<223> OTHER INFORMATION: synthetic

<400> SEQUENCE: 7

Gly Pro Leu Gly Leu Trp Ala Gln
1               5

<210> SEQ ID NO 8
<211> LENGTH: 9
<212> TYPE: PRT
<213> ORGANISM: Artificial sequence
<220> FEATURE:
<223> OTHER INFORMATION: synthetic

<400> SEQUENCE: 8

Pro Cys Pro Gly Arg Val Val Gly Gly
1               5

<210> SEQ ID NO 9
<211> LENGTH: 7
<212> TYPE: PRT
<213> ORGANISM: Artificial sequence
<220> FEATURE:
<223> OTHER INFORMATION: synthetic

<400> SEQUENCE: 9

Pro Gly Ser Gly Arg Ser Ala
1               5

<210> SEQ ID NO 10
<211> LENGTH: 7
<212> TYPE: PRT
<213> ORGANISM: Artificial sequence
<220> FEATURE:
<223> OTHER INFORMATION: synthetic

<400> SEQUENCE: 10

Pro Gly Ser Gly Lys Ser Ala
1               5

<210> SEQ ID NO 11
<211> LENGTH: 7
<212> TYPE: PRT
<213> ORGANISM: Artificial sequence
<220> FEATURE:
<223> OTHER INFORMATION: synthetic

<400> SEQUENCE: 11

Pro Gln Arg Gly Arg Ser Ala
1               5

<210> SEQ ID NO 12
<211> LENGTH: 9
<212> TYPE: PRT
<213> ORGANISM: Artificial sequence
<220> FEATURE:
<223> OTHER INFORMATION: synthetic

<400> SEQUENCE: 12

Pro Cys Pro Gly Arg Val Val Gly Gly
1               5
```

```
<210> SEQ ID NO 13
<211> LENGTH: 6
<212> TYPE: PRT
<213> ORGANISM: Artificial Sequence
<220> FEATURE:
<223> OTHER INFORMATION: synthetic

<400> SEQUENCE: 13

Gly Ser Gly Arg Ser Ala
1               5

<210> SEQ ID NO 14
<211> LENGTH: 6
<212> TYPE: PRT
<213> ORGANISM: Artificial sequence
<220> FEATURE:
<223> OTHER INFORMATION: synthetic

<400> SEQUENCE: 14

Gly Ser Gly Lys Ser Ala
1               5

<210> SEQ ID NO 15
<211> LENGTH: 6
<212> TYPE: PRT
<213> ORGANISM: Artificial sequence
<220> FEATURE:
<223> OTHER INFORMATION: synthetic

<400> SEQUENCE: 15

Gln Arg Gly Arg Ser Ala
1               5

<210> SEQ ID NO 16
<211> LENGTH: 21
<212> TYPE: DNA
<213> ORGANISM: Artificial sequence
<220> FEATURE:
<223> OTHER INFORMATION: synthetic

<400> SEQUENCE: 16
gttagacgat aaaccagtcc t                                          21

<210> SEQ ID NO 17
<211> LENGTH: 31
<212> TYPE: DNA
<213> ORGANISM: Artificial sequence
<220> FEATURE:
<223> OTHER INFORMATION: synthetic

<400> SEQUENCE: 17
ctaccagatt taaatccttt ccattaaaaa t                               31

<210> SEQ ID NO 18
<211> LENGTH: 48
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (29)..(29)
<223> OTHER INFORMATION: n is g or c
```

<400> SEQUENCE: 18
caagtgctgg acctacggtt ccagacnnng acaatgatgg aatccccta         48

<210> SEQ ID NO 19
<211> LENGTH: 24
<212> TYPE: DNA
<213> ORGANISM: Artificial sequence
<220> FEATURE:
<223> OTHER INFORMATION: synthetic

<400> SEQUENCE: 19
ctggaaccgt aggtccagca cttg                                    24

<210> SEQ ID NO 20
<211> LENGTH: 58
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (40)..(40)
<223> OTHER INFORMATION: n is g or c

<400> SEQUENCE: 20
cgaggtagaa ggatatacgg ttgatgtcaa aaataaannn acctttcttt caccatgg   58

<210> SEQ ID NO 21
<211> LENGTH: 29
<212> TYPE: DNA
<213> ORGANISM: Artificial sequence
<220> FEATURE:
<223> OTHER INFORMATION: synthetic

<400> SEQUENCE: 21
tgacatcaac cgtatatcct tctacctcg                               29

<210> SEQ ID NO 22
<211> LENGTH: 58
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (34)..(34)
<223> OTHER INFORMATION: n is g or c

<400> SEQUENCE: 22
caaaaataaa aggacctttc tttcaacatg gnnntctaat attcatgaaa agaaaggg   58

<210> SEQ ID NO 23
<211> LENGTH: 30
<212> TYPE: DNA
<213> ORGANISM: Artificial sequence
<220> FEATURE:
<223> OTHER INFORMATION: synthetic

<400> SEQUENCE: 23
catggtgaaa gaaaggtcct tttattttg                               30

```
<210> SEQ ID NO 24
<211> LENGTH: 58
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (43)..(43)
<223> OTHER INFORMATION: n is g or c

<400> SEQUENCE: 24
caaaaataaa aggacctttc tttcaccatg gatatctaat nnncatgaaa agaaaggg          58

<210> SEQ ID NO 25
<211> LENGTH: 59
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (36)..(36)
<223> OTHER INFORMATION: n is g or c

<400> SEQUENCE: 25
ctttcaccat ggatatctaa tattcatgaa aagnnngggt taaccaaata taaatcatc         59

<210> SEQ ID NO 26
<211> LENGTH: 33
<212> TYPE: DNA
<213> ORGANISM: Artificial sequence
<220> FEATURE:
<223> OTHER INFORMATION: synthetic

<400> SEQUENCE: 26
cttttcatga atattagata tccatggtga aag                                     33

<210> SEQ ID NO 27
<211> LENGTH: 59
<212> TYPE: DNA
<213> ORGANISM: Artificial sequence
<220> FEATURE:
<223> OTHER INFORMATION: synthetic

<400> SEQUENCE: 27
aaaataaaag aacttttctt tcaccatggc gttctaatat tcatgaaaag aaaggatta         59

<210> SEQ ID NO 28
<211> LENGTH: 59
<212> TYPE: DNA
<213> ORGANISM: Artificial sequence
<220> FEATURE:
<223> OTHER INFORMATION: synthetic

<400> SEQUENCE: 28
taatcctttc ttttcatgaa tattagaacg ccatggtgaa agaaaagttc ttttatttt         59
```

```
<210> SEQ ID NO 29
<211> LENGTH: 2307
<212> TYPE: DNA
<213> ORGANISM: Artificial sequence
<220> FEATURE:
<223> OTHER INFORMATION: synthetic

<400> SEQUENCE: 29
atgaaaaaac gaaaagtgtt aataccatta atggcattgt ctacgatatt agtttcaagc      60
acaggtaatt tagaggtgat tcaggcagaa gttaaacagg agaaccggtt attaaatgaa     120
tcagaatcaa gttcccaggg gttactagga tactatttta gtgatttgaa ttttcaagca     180
cccatggtgg ttacctcttc tactacaggg gatttatcta ttcctagttc tgagttagaa     240
aatattccat cggaaaacca atattttcaa tctgctatt ggtcaggatt tatcaaagtt      300
aagaagagtg atgaatatac atttgctact tccgctgata tcatgtaac aatgtgggta      360
gatgaccaag aagtgattaa taaagcttct aattctaaca aaatcagatt agaaaaagga     420
agattatatc aaataaaaat tcaatatcaa cgagaaaatc ctactgaaaa aggattggat     480
ttcaagttgt actggaccga ttctcaaaat aaaaagaag tgatttctag tgataactta     540
caattgccag aattaaaaca aaaatcttcg aactcaggac cattaggaat gttgagtcaa     600
agtacaagtg ctggacctac ggttccagac cgtgacaatg atggaatccc tgattcatta     660
gaggtagaag gatatacggt tgatgtcaaa aataaaagaa cttttctttc accatgcgc      720
tctaatattc atgaaaagaa aggattaacc aaatataaat catctcctga aaatggagc      780
acggcttctg atccgtacag tgatttcgaa aaggttacag acggattga taagaatgta      840
tcaccagagg caagacaccc ccttgtggca gcttatccga ttgtacatgt agatatggag     900
aatattattc tctcaaaaaa tgaggatcaa tccacacaga atactgatag tcaaacgaga     960
acaataagta aaaatacttc tacaagtagg acacatacta gtgaagtaca tggaaatgca    1020
gaagtgcatg cgtcgttctt tgatattggt gggagtgtat ctgcaggatt tagtaattcg    1080
aattcaagta cggtcgcaat tgatcattca ctatctctag caggggaaag aacttgggct    1140
gaaacaatgg gtttaaatac cgctgataca gcaagattaa atgccaatat tagatatgta    1200
aatactggga cggctccaat ctacaacgtg ttaccaacga cttcgttagt gttaggaaaa    1260
aatcaaacac tcgcgacaat taaagctaag gaaaaccaat taagtcaaat acttgcacct    1320
aataattatt atccttctaa aaacttggcg ccaatcgcat taaatgcaca agacgatttc    1380
agttctactc caattacaat gaattacaat caatttcttg agttagaaaa aacgaaacaa    1440
ttaagattag atacggatca agtatatggg aatatagcaa catacaattt tgaaaatgga    1500
agagtgaggg tggatacagg ctcgaactgg agtgaagtgt taccgcaaat tcaagaaaca    1560
actgcacgta tcatttttaa tggaaaagat ttaaatctgg tagaaaggcg gatagcggcg    1620
gttaatccta gtgatccatt agaaacgact aaaccggata tgacattaaa agaagccctt    1680
aaaatagcat ttggatttaa cgaaccgaat ggaaacttac aatatcaagg aaagacata    1740
accgaatttg atttttaattt cgatcaacaa acatctcaaa atatcaagaa tcagttagcg    1800
gaattaaacg caactaacat atatactgta ttagataaaa tcaaattaaa tgcaaaaatg    1860
aatatttaa taagagataa acgttttcat tatgatagaa ataacatagc agttggggcg    1920
gatgagtcag tagttaagga ggctcataga gaagtaatta ttcgtcaac agagggatta    1980
ttgttaaata ttgataagga tataagaaaa atattatcag gttatattgt agaaattgaa    2040
gatactgaag ggcttaaaga agttataaat gacagatatg atatgttgaa tatttctagt    2100
```

```
ttacggcaag atggaaaaac atttatagat tttaaaaaat ataatgataa attaccgtta    2160
tatataagta atcccaatta taaggtaaat gtatatgctg ttactaaaga aaacactatt    2220
attaatccta gtgagaatgg ggatactagt accaacggga tcaagaaaat tttaatcttt    2280
tctaaaaaag gctatgagat aggataa                                        2307
```

<210> SEQ ID NO 30
<211> LENGTH: 768
<212> TYPE: PRT
<213> ORGANISM: Artificial sequence
<220> FEATURE:
<223> OTHER INFORMATION: synthetic

<400> SEQUENCE: 30

```
Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val Lys
            20                  25                  30

Gln Glu Asn Arg Leu Leu Asn Glu Ser Glu Ser Ser Gln Gly Leu
        35                  40                  45

Leu Gly Tyr Tyr Phe Ser Asp Leu Asn Phe Gln Ala Pro Met Val Val
    50                  55                  60

Thr Ser Ser Thr Thr Gly Asp Leu Ser Ile Pro Ser Ser Glu Leu Glu
65                  70                  75                  80

Asn Ile Pro Ser Glu Asn Gln Tyr Phe Gln Ser Ala Ile Trp Ser Gly
                85                  90                  95

Phe Ile Lys Val Lys Lys Ser Asp Glu Tyr Thr Phe Ala Thr Ser Ala
            100                 105                 110

Asp Asn His Val Thr Met Trp Val Asp Asp Gln Glu Val Ile Asn Lys
        115                 120                 125

Ala Ser Asn Ser Asn Lys Ile Arg Leu Glu Lys Gly Arg Leu Tyr Gln
    130                 135                 140

Ile Lys Ile Gln Tyr Gln Arg Glu Asn Pro Thr Glu Lys Gly Leu Asp
145                 150                 155                 160

Phe Lys Leu Tyr Trp Thr Asp Ser Gln Asn Lys Lys Glu Val Ile Ser
                165                 170                 175

Ser Asp Asn Leu Gln Leu Pro Glu Leu Lys Gln Lys Ser Ser Asn Ser
            180                 185                 190

Gly Pro Leu Gly Met Leu Ser Gln Ser Thr Ser Ala Gly Pro Thr Val
        195                 200                 205

Pro Asp Arg Asp Asn Asp Gly Ile Pro Asp Ser Leu Glu Val Glu Gly
    210                 215                 220

Tyr Thr Val Asp Val Lys Asn Lys Arg Thr Phe Leu Ser Pro Trp Arg
225                 230                 235                 240

Ser Asn Ile His Glu Lys Lys Gly Leu Thr Lys Tyr Lys Ser Ser Pro
                245                 250                 255

Glu Lys Trp Ser Thr Ala Ser Asp Pro Tyr Ser Asp Phe Glu Lys Val
            260                 265                 270

Thr Gly Arg Ile Asp Lys Asn Val Ser Pro Glu Ala Arg His Pro Leu
        275                 280                 285

Val Ala Ala Tyr Pro Ile Val His Val Asp Met Glu Asn Ile Ile Leu
    290                 295                 300

Ser Lys Asn Glu Asp Gln Ser Thr Gln Asn Thr Asp Ser Gln Thr Arg
305                 310                 315                 320
```

```
Thr Ile Ser Lys Asn Thr Ser Thr Ser Arg Thr His Thr Ser Glu Val
                325                 330                 335

His Gly Asn Ala Glu Val His Ala Ser Phe Phe Asp Ile Gly Gly Ser
            340                 345                 350

Val Ser Ala Gly Phe Ser Asn Ser Asn Ser Ser Thr Val Ala Ile Asp
        355                 360                 365

His Ser Leu Ser Leu Ala Gly Glu Arg Thr Trp Ala Glu Thr Met Gly
370                 375                 380

Leu Asn Thr Ala Asp Thr Ala Arg Leu Asn Ala Asn Ile Arg Tyr Val
385                 390                 395                 400

Asn Thr Gly Thr Ala Pro Ile Tyr Asn Val Leu Pro Thr Thr Ser Leu
                405                 410                 415

Val Leu Gly Lys Asn Gln Thr Leu Ala Thr Ile Lys Ala Lys Glu Asn
            420                 425                 430

Gln Leu Ser Gln Ile Leu Ala Pro Asn Asn Tyr Tyr Pro Ser Lys Asn
        435                 440                 445

Leu Ala Pro Ile Ala Leu Asn Ala Gln Asp Asp Phe Ser Ser Thr Pro
    450                 455                 460

Ile Thr Met Asn Tyr Asn Gln Phe Leu Glu Leu Glu Lys Thr Lys Gln
465                 470                 475                 480

Leu Arg Leu Asp Thr Asp Gln Val Tyr Gly Asn Ile Ala Thr Tyr Asn
                485                 490                 495

Phe Glu Asn Gly Arg Val Arg Val Asp Thr Gly Ser Asn Trp Ser Glu
            500                 505                 510

Val Leu Pro Gln Ile Gln Glu Thr Thr Ala Arg Ile Ile Phe Asn Gly
        515                 520                 525

Lys Asp Leu Asn Leu Val Glu Arg Arg Ile Ala Ala Val Asn Pro Ser
    530                 535                 540

Asp Pro Leu Glu Thr Thr Lys Pro Asp Met Thr Leu Lys Glu Ala Leu
545                 550                 555                 560

Lys Ile Ala Phe Gly Phe Asn Glu Pro Asn Gly Asn Leu Gln Tyr Gln
                565                 570                 575

Gly Lys Asp Ile Thr Glu Phe Asp Phe Asn Phe Asp Gln Gln Thr Ser
            580                 585                 590

Gln Asn Ile Lys Asn Gln Leu Ala Glu Leu Asn Ala Thr Asn Ile Tyr
        595                 600                 605

Thr Val Leu Asp Lys Ile Lys Leu Asn Ala Lys Met Asn Ile Leu Ile
    610                 615                 620

Arg Asp Lys Arg Phe His Tyr Asp Arg Asn Asn Ile Ala Val Gly Ala
625                 630                 635                 640

Asp Glu Ser Val Val Lys Glu Ala His Arg Glu Val Ile Asn Ser Ser
                645                 650                 655

Thr Glu Gly Leu Leu Leu Asn Ile Asp Lys Asp Ile Arg Lys Ile Leu
            660                 665                 670

Ser Gly Tyr Ile Val Glu Ile Glu Asp Thr Glu Gly Leu Lys Glu Val
        675                 680                 685

Ile Asn Asp Arg Tyr Asp Met Leu Asn Ile Ser Ser Leu Arg Gln Asp
    690                 695                 700

Gly Lys Thr Phe Ile Asp Phe Lys Lys Tyr Asn Asp Lys Leu Pro Leu
705                 710                 715                 720

Tyr Ile Ser Asn Pro Asn Tyr Lys Val Asn Val Tyr Ala Val Thr Lys
                725                 730                 735
```

Glu Asn Thr Ile Ile Asn Pro Ser Glu Asn Gly Asp Thr Ser Thr Asn
                    740                 745                 750

Gly Ile Lys Lys Ile Leu Ile Phe Ser Lys Lys Gly Tyr Glu Ile Gly
            755                 760                 765

<210> SEQ ID NO 31
<211> LENGTH: 2304
<212> TYPE: DNA
<213> ORGANISM: Artificial sequence
<220> FEATURE:
<223> OTHER INFORMATION: synthetic

<400> SEQUENCE: 31

| | |
|---|---|
| atgaaaaaac gaaaagtgtt aataccatta atggcattgt ctacgatatt agtttcaagc | 60 |
| acaggtaatt tagaggtgat tcaggcagaa gttaaacagg agaaccggtt attaaatgaa | 120 |
| tcagaatcaa gttcccaggg gttactagga tactatttta gtgatttgaa ttttcaagca | 180 |
| cccatggtgg ttacctcttc tactacaggg gatttatcta ttcctagttc tgagttagaa | 240 |
| aatattccat cggaaaacca atattttcaa tctgctattt ggtcaggatt tatcaaagtt | 300 |
| aagaagagtg atgaatatac atttgctact ccgctgata atcatgtaac aatgtgggta | 360 |
| gatgaccaag aagtgattaa taaagcttct aattctaaca aaatcagatt agaaaaagga | 420 |
| agattatatc aaataaaaat tcaatatcaa cgagaaaatc tactgaaaa aggattggat | 480 |
| ttcaagttgt actggaccga ttctcaaaat aaaaagaag tgatttctag tgataactta | 540 |
| caattgccag aattaaaaca aaaatcttcg aactcaccag gaagtggaag atcagcaagt | 600 |
| acaagtgctg gacctacggt tccagaccgt gacaatgatg aatccctga ttcattagag | 660 |
| gtagaaggat atacggttga tgtcaaaaat aaagcaactt ttctttcacc atggatttct | 720 |
| aatattcatg aaaagaaagg attaaccaaa tataaatcat ctcctgaaaa atggagcacg | 780 |
| gcttctgatc cgtacagtga tttcgaaaag gttacaggac ggattgataa gaatgtatca | 840 |
| ccagaggcaa gacacccct tgtggcagct tatccgattg tacatgtaga tatggagaat | 900 |
| attattctct caaaaaatga ggatcaatcc acacagaata ctgatagtca aacgagaaca | 960 |
| ataagtaaaa atacttctac aagtaggaca catactagtg aagtacatgg aaatgcagaa | 1020 |
| gtgcatgcgt cgttctttga tattggtggg agtgtatctg caggatttag taattcgaat | 1080 |
| tcaagtacgg tcgcaattga tcattcacta tctctagcag gggaaagaac ttgggctgaa | 1140 |
| acaatgggtt taaataccgc tgatacagca agattaaatg ccaatattag atatgtaaat | 1200 |
| actgggacgg ctccaatcta caacgtgtta ccaacgactt cgttagtgtt aggaaaaaat | 1260 |
| caaacactcg cgacaattaa agctaaggaa aaccaattaa gtcaaatact tgcacctaat | 1320 |
| aattattatc cttctaaaaa cttggcgcca atcgcattaa atgcacaaga cgatttcagt | 1380 |
| tctactccaa ttacaatgaa ttacaatcaa tttcttgagt tagaaaaac gaaacaatta | 1440 |
| agattagata cggatcaagt atatgggaat atagcaacat acaattttga aaatggaaga | 1500 |
| gtgagggtgg atacaggctc gaactggagt gaagtgttac cgcaaattca gaaacaact | 1560 |
| gcacgtatca ttttaatgg aaaagattta atctggtag aaggcggat agcggcggtt | 1620 |
| aatcctagtg atccattaga aacgactaaa ccggatatga cattaaaaga agcccttaaa | 1680 |
| atagcatttg gatttaacga accgaatgga aacttacaat atcaagggaa agacataacc | 1740 |
| gaatttgatt ttaatttcga tcaacaaaca tctcaaaata tcaagaatca gttagcggaa | 1800 |
| ttaaacgcaa ctaacatata tactgtatta gataaaatca aattaaatgc aaaaatgaat | 1860 |
| atttaataa gagataaacg ttttcattat gatagaaata acatagcagt tggggcggat | 1920 |

-continued

```
gagtcagtag ttaaggaggc tcatagagaa gtaattaatt cgtcaacaga gggattattg    1980
ttaaatattg ataaggatat aagaaaaata ttatcaggtt atattgtaga aattgaagat    2040
actgaagggc ttaagaagt tataaatgac agatatgata tgttgaatat ttctagttta    2100
cggcaagatg gaaaacatt tatagatttt aaaaaatata atgataaatt accgttatat    2160
ataagtaatc ccaattataa ggtaaatgta tatgctgtta ctaaagaaaa cactattatt    2220
aatcctagtg agaatgggga tactagtacc aacgggatca agaaaatttt aatcttttct    2280
aaaaaaggct atgagatagg ataa                                          2304
```

<210> SEQ ID NO 32
<211> LENGTH: 767
<212> TYPE: PRT
<213> ORGANISM: Artificial sequence
<220> FEATURE:
<223> OTHER INFORMATION: synthetic

<400> SEQUENCE: 32

```
Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val Lys
            20                  25                  30

Gln Glu Asn Arg Leu Leu Asn Glu Ser Glu Ser Ser Gln Gly Leu
        35                  40                  45

Leu Gly Tyr Tyr Phe Ser Asp Leu Asn Phe Gln Ala Pro Met Val Val
    50                  55                  60

Thr Ser Ser Thr Thr Gly Asp Leu Ser Ile Pro Ser Ser Glu Leu Glu
65                  70                  75                  80

Asn Ile Pro Ser Glu Asn Gln Tyr Phe Gln Ser Ala Ile Trp Ser Gly
                85                  90                  95

Phe Ile Lys Val Lys Lys Ser Asp Glu Tyr Thr Phe Ala Thr Ser Ala
            100                 105                 110

Asp Asn His Val Thr Met Trp Val Asp Asp Gln Glu Val Ile Asn Lys
        115                 120                 125

Ala Ser Asn Ser Asn Lys Ile Arg Leu Glu Lys Gly Arg Leu Tyr Gln
    130                 135                 140

Ile Lys Ile Gln Tyr Gln Arg Glu Asn Pro Thr Glu Lys Gly Leu Asp
145                 150                 155                 160

Phe Lys Leu Tyr Trp Thr Asp Ser Gln Asn Lys Lys Glu Val Ile Ser
                165                 170                 175

Ser Asp Asn Leu Gln Leu Pro Glu Leu Lys Gln Lys Ser Ser Asn Ser
            180                 185                 190

Pro Gly Ser Gly Arg Ser Ala Ser Thr Ser Ala Gly Pro Thr Val Pro
        195                 200                 205

Asp Arg Asp Asn Asp Gly Ile Pro Asp Ser Leu Glu Val Glu Gly Tyr
    210                 215                 220

Thr Val Asp Val Lys Asn Lys Ala Thr Phe Leu Ser Pro Trp Ile Ser
225                 230                 235                 240

Asn Ile His Glu Lys Lys Gly Leu Thr Lys Tyr Lys Ser Ser Pro Glu
                245                 250                 255

Lys Trp Ser Thr Ala Ser Asp Pro Tyr Ser Asp Phe Glu Lys Val Thr
            260                 265                 270

Gly Arg Ile Asp Lys Asn Val Ser Pro Glu Ala Arg His Pro Leu Val
        275                 280                 285
```

```
Ala Ala Tyr Pro Ile Val His Val Asp Met Glu Asn Ile Ile Leu Ser
290                 295                 300

Lys Asn Glu Asp Gln Ser Thr Gln Asn Thr Asp Ser Gln Thr Arg Thr
305                 310                 315                 320

Ile Ser Lys Asn Thr Ser Thr Ser Arg Thr His Thr Ser Glu Val His
                325                 330                 335

Gly Asn Ala Glu Val His Ala Ser Phe Phe Asp Ile Gly Gly Ser Val
                340                 345                 350

Ser Ala Gly Phe Ser Asn Ser Asn Ser Ser Thr Val Ala Ile Asp His
                355                 360                 365

Ser Leu Ser Leu Ala Gly Glu Arg Thr Trp Ala Glu Thr Met Gly Leu
370                 375                 380

Asn Thr Ala Asp Thr Ala Arg Leu Asn Ala Asn Ile Arg Tyr Val Asn
385                 390                 395                 400

Thr Gly Thr Ala Pro Ile Tyr Asn Val Leu Pro Thr Thr Ser Leu Val
                405                 410                 415

Leu Gly Lys Asn Gln Thr Leu Ala Thr Ile Lys Ala Lys Glu Asn Gln
                420                 425                 430

Leu Ser Gln Ile Leu Ala Pro Asn Asn Tyr Tyr Pro Ser Lys Asn Leu
                435                 440                 445

Ala Pro Ile Ala Leu Asn Ala Gln Asp Asp Phe Ser Ser Thr Pro Ile
                450                 455                 460

Thr Met Asn Tyr Asn Gln Phe Leu Glu Leu Glu Lys Thr Lys Gln Leu
465                 470                 475                 480

Arg Leu Asp Thr Asp Gln Val Tyr Gly Asn Ile Ala Thr Tyr Asn Phe
                485                 490                 495

Glu Asn Gly Arg Val Arg Val Asp Thr Gly Ser Asn Trp Ser Glu Val
                500                 505                 510

Leu Pro Gln Ile Gln Glu Thr Thr Ala Arg Ile Ile Phe Asn Gly Lys
                515                 520                 525

Asp Leu Asn Leu Val Glu Arg Arg Ile Ala Ala Val Asn Pro Ser Asp
                530                 535                 540

Pro Leu Glu Thr Thr Lys Pro Asp Met Thr Leu Lys Glu Ala Leu Lys
545                 550                 555                 560

Ile Ala Phe Gly Phe Asn Glu Pro Asn Gly Asn Leu Gln Tyr Gln Gly
                565                 570                 575

Lys Asp Ile Thr Glu Phe Asp Phe Asn Phe Asp Gln Gln Thr Ser Gln
                580                 585                 590

Asn Ile Lys Asn Gln Leu Ala Glu Leu Asn Ala Thr Asn Ile Tyr Thr
                595                 600                 605

Val Leu Asp Lys Ile Lys Leu Asn Ala Lys Met Asn Ile Leu Ile Arg
610                 615                 620

Asp Lys Arg Phe His Tyr Asp Arg Asn Asn Ile Ala Val Gly Ala Asp
625                 630                 635                 640

Glu Ser Val Val Lys Glu Ala His Arg Glu Val Ile Asn Ser Ser Thr
                645                 650                 655

Glu Gly Leu Leu Leu Asn Ile Asp Lys Asp Ile Arg Lys Ile Leu Ser
                660                 665                 670

Gly Tyr Ile Val Glu Ile Glu Asp Thr Glu Gly Leu Lys Glu Val Ile
                675                 680                 685

Asn Asp Arg Tyr Asp Met Leu Asn Ile Ser Ser Leu Arg Gln Asp Gly
690                 695                 700
```

```
Lys Thr Phe Ile Asp Phe Lys Lys Tyr Asn Asp Lys Leu Pro Leu Tyr
705                 710                 715                 720

Ile Ser Asn Pro Asn Tyr Lys Val Asn Val Tyr Ala Val Thr Lys Glu
            725                 730                 735

Asn Thr Ile Ile Asn Pro Ser Glu Asn Gly Asp Thr Ser Thr Asn Gly
            740                 745                 750

Ile Lys Lys Ile Leu Ile Phe Ser Lys Lys Gly Tyr Glu Ile Gly
            755                 760                 765

<210> SEQ ID NO 33
<211> LENGTH: 2295
<212> TYPE: DNA
<213> ORGANISM: Artificial sequence
<220> FEATURE:
<223> OTHER INFORMATION: synthetic

<400> SEQUENCE: 33
```

| | | | | | |
|---|---|---|---|---|---|
| atgaaaaaac | gaaaagtgtt | aataccatta | atggcattgt | ctacgatatt | agtttcaagc | 60 |
| acaggtaatt | tagaggtgat | tcaggcagaa | gttaaacagg | agaaccggtt | attaaatgaa | 120 |
| tcagaatcaa | gttcccaggg | gttactagga | tactatttta | gtgatttgaa | ttttcaagca | 180 |
| cccatggtgg | ttacctcttc | tactacaggg | gatttatcta | ttcctagttc | tgagttagaa | 240 |
| aatattccat | cggaaaacca | atattttcaa | tctgctattt | ggtcaggatt | tatcaaagtt | 300 |
| aagaagagtg | atgaatatac | atttgctact | tccgctgata | tcatgtaac | aatgtgggta | 360 |
| gatgaccaag | aagtgattaa | taaagcttct | aattctaaca | aaatcagatt | agaaaaagga | 420 |
| agattatatc | aaataaaaat | tcaatatcaa | cgagaaaatc | ctactgaaaa | aggattggat | 480 |
| ttcaagttgt | actggaccga | ttctcaaaat | aaaaaagaag | tgatttctag | tgataactta | 540 |
| caattgccag | aattaaaaca | aaaatcttcg | aactcaagaa | aaaagcgaag | tacaagtgct | 600 |
| ggacctacgg | ttccagaccg | tgacaatgat | ggaatccctg | attcattaga | ggtagaagga | 660 |
| tatacggttg | atgtcaaaaa | taaagaact | tttctttcac | catggattc | taatattcat | 720 |
| gaaaagaaag | gattaaccaa | atataaatca | tctcctgaaa | aatggagcac | ggcttctgat | 780 |
| ccgtacagtg | atttcgaaaa | ggttacagga | cggattgata | gaatgtatc | accagaggca | 840 |
| agacaccccc | ttgtggcagc | ttatccgatt | gtacatgtag | atatggagaa | tattattctc | 900 |
| tcaaaaaatg | aggatcaatc | cacacagaat | actgatagtc | aaacgagaac | aataagtaaa | 960 |
| aatacttcta | caagtaggac | acatactagt | gaagtacatg | gaaatgcaga | agtgcatgcg | 1020 |
| tcgttctttg | atattggtgg | gagtgtatct | gcaggattta | gtaattcgaa | ttcaagtacg | 1080 |
| gtcgcaattg | atcattcact | atctctagca | ggggaaagaa | cttgggctga | acaatgggt | 1140 |
| ttaaataccg | ctgatacagc | aagattaaat | gccaatatta | gatatgtaaa | tactgggacg | 1200 |
| gctccaatct | acaacgtgtt | accaacgact | tcgttagtgt | taggaaaaaa | tcaaacactc | 1260 |
| gcgacaatta | aagctaagga | aaaccaatta | agtcaaatac | ttgcacctaa | taattattat | 1320 |
| ccttctaaaa | acttggcgcc | aatcgcatta | aatgcacaag | acgatttcag | ttctactcca | 1380 |
| attacaatga | attacaatca | atttcttgag | ttagaaaaaa | cgaaacaatt | aagattagat | 1440 |
| acggatcaag | tatatgggaa | tatagcaaca | tacaattttg | aaaatggaag | agtgagggtg | 1500 |
| gatacaggct | cgaactggag | tgaagtgtta | ccgcaaattc | aagaaacaac | tgcacgtatc | 1560 |
| attttaatg | gaaaagattt | aaatctggta | gaaaggcgga | tagcggcggt | taatcctagt | 1620 |
| gatccattag | aaacgactaa | accggatatg | acattaaaag | aagcccttaa | aatagcattt | 1680 |

```
ggatttaacg aaccgaatgg aaacttacaa tatcaaggga aagacataac cgaatttgat   1740
tttaatttcg atcaacaaac atctcaaaat atcaagaatc agttagcgga attaaacgca   1800
actaacatat atactgtatt agataaaatc aaattaaatg caaaaatgaa tattttaata   1860
agagataaac gttttcatta tgatagaaat aacatagcag ttggggcgga tgagtcagta   1920
gttaaggagg ctcatagaga agtaattaat tcgtcaacag agggattatt gttaaatatt   1980
gataaggata taagaaaaat attatcaggt tatattgtag aaattgaaga tactgaaggg   2040
cttaaagaag ttataaatga cagatatgat atgttgaata tttctagttt acggcaagat   2100
ggaaaaacat ttatagattt taaaaaatat aatgataaat taccgttata tataagtaat   2160
cccaattata aggtaaatgt atatgctgtt actaaagaaa acactattat taatcctagt   2220
gagaatgggg atactagtac caacgggatc aagaaaattt taatctttc taaaaaaggc    2280 tatgagatag gataa                                                   2295

<210> SEQ ID NO 34
<211> LENGTH: 32
<212> TYPE: DNA
<213> ORGANISM: Artificial Sequence
<220> FEATURE:
<223> OTHER INFORMATION: synthetic

<400> SEQUENCE: 34
gcttgaattc atttcattat gatagaaata ac                                 32

<210> SEQ ID NO 35
<211> LENGTH: 32
<212> TYPE: DNA
<213> ORGANISM: Artificial Sequence
<220> FEATURE:
<223> OTHER INFORMATION: synthetic

<400> SEQUENCE: 35
aattcaagct ttcctatctc atagcctttt tt                                 32

<210> SEQ ID NO 36
<211> LENGTH: 20
<212> TYPE: DNA
<213> ORGANISM: Artificial Sequence
<220> FEATURE:
<223> OTHER INFORMATION: synthetic

<400> SEQUENCE: 36
taagtacgca atgggccacg                                               20

<210> SEQ ID NO 37
<211> LENGTH: 20
<212> TYPE: DNA
<213> ORGANISM: Artificial Sequence
<220> FEATURE:
<223> OTHER INFORMATION: synthetic

<400> SEQUENCE: 37
aactcagcgg cagtctcaac                                               20

<210> SEQ ID NO 38
<211> LENGTH: 75
<212> TYPE: DNA
<213> ORGANISM: Artificial Sequence
<220> FEATURE:
<223> OTHER INFORMATION: synthetic
```

```
<400> SEQUENCE: 38
tgaagatact gaaggcctta aagaagttat aaatgacaga tatgatatgt tgaatatctc      60
gagtttacgg caaga                                                       75

<210> SEQ ID NO 39
<211> LENGTH: 75
<212> TYPE: DNA
<213> ORGANISM: Artificial Sequence
<220> FEATURE:
<223> OTHER INFORMATION: synthetic

<400> SEQUENCE: 39
tcttgccgta aactcgagat attcaacata tcatatctgt catttataac ttctttaagg      60
ccttcagtat cttca                                                       75
```